(12) United States Patent
Murakata et al.

(10) Patent No.: US 7,759,371 B2
(45) Date of Patent: Jul. 20, 2010

(54) THIADIAZOLINE DERIVATIVE

(75) Inventors: Chikara Murakata, Shizuoka (JP); Kazuhiko Kato, Shizuoka (JP); Yoshihisa Ohta, Kanagawa (JP); Ryuichiro Nakai, Shizuoka (JP); Yoshinori Yamashita, Shizuoka (JP); Takeshi Takahashi, Shizuoka (JP)

(73) Assignees: Kyowa Hakko Kirin Co., Ltd., Tokyo (JP); FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/098,736

(22) Filed: Apr. 7, 2008

(65) Prior Publication Data

US 2008/0207706 A1 Aug. 28, 2008

Related U.S. Application Data

(62) Division of application No. 10/497,531, filed as application No. PCT/JP02/12961 on Dec. 11, 2002, now Pat. No. 7,425,636.

(30) Foreign Application Priority Data

Dec. 11, 2001 (JP) ............................... 2001-377456
Aug. 16, 2002 (JP) ............................... 2002-237399

(51) Int. Cl.
    *A61K 31/433* (2006.01)
(52) U.S. Cl. .................................... 514/363
(58) Field of Classification Search .......... 514/363
    See application file for complete search history.

(56) References Cited

U.S. PATENT DOCUMENTS

| 4,338,449 A | 7/1982 | Tao et al. |
| 4,346,225 A | 8/1982 | Tao et al. |
| 4,699,913 A | 10/1987 | Farooq et al. |
| 4,927,822 A | 5/1990 | Brown et al. |
| 5,643,911 A | 7/1997 | Yamada et al. |
| 5,814,647 A | 9/1998 | Urban et al. |
| 6,207,690 B1 | 3/2001 | Urban et al. |
| 6,235,762 B1 | 5/2001 | Takasugi et al. |
| 6,414,121 B1 | 7/2002 | Wood et al. |
| 6,545,004 B1 | 4/2003 | Finer et al. |
| 6,545,030 B1 | 4/2003 | Barrett et al. |
| 6,562,831 B1 | 5/2003 | Finer et al. |
| 6,630,479 B1 | 10/2003 | Finer et al. |
| 6,831,085 B1 | 12/2004 | Bergnes et al. |
| 6,992,082 B2 | 1/2006 | Finer et al. |
| 7,060,705 B2 | 6/2006 | Fraley et al. |
| 7,105,668 B1 | 9/2006 | Bergnes et al. |
| 7,119,089 B2 | 10/2006 | Finer et al. |
| 7,230,000 B1 | 6/2007 | Finer et al. |
| 2002/0143026 A1 | 10/2002 | Lombardo et al. |
| 2002/0165240 A1 | 11/2002 | Kimball et al. |
| 2003/0008888 A1 | 1/2003 | Kimball et al. |
| 2004/0023996 A1 | 2/2004 | Finer et al. |
| 2004/0087548 A1 | 5/2004 | Salvati et al. |
| 2004/0132719 A1 | 7/2004 | Finer et al. |
| 2004/0132830 A1 | 7/2004 | Finer et al. |
| 2004/0254203 A1 | 12/2004 | Finer et al. |
| 2004/0259826 A1 | 12/2004 | Fraley et al. |
| 2005/0119484 A1 | 6/2005 | Breslin et al. |
| 2005/0187232 A1 | 8/2005 | Finer et al. |
| 2005/0203110 A1 | 9/2005 | Coleman et al. |
| 2006/0014736 A1 | 1/2006 | Finer et al. |
| 2006/0074113 A1 | 4/2006 | Murakata et al. |
| 2006/0100161 A1 | 5/2006 | Hans et al. |
| 2006/0111424 A1 | 5/2006 | Salvati et al. |
| 2007/0112044 A1 | 5/2007 | Murakata et al. |
| 2007/0155804 A1 | 7/2007 | Murakata et al. |
| 2007/0213380 A1 | 9/2007 | Murakata et al. |
| 2007/0254902 A1 | 11/2007 | Finer et al. |
| 2007/0276017 A1 | 11/2007 | Murakata et al. |

FOREIGN PATENT DOCUMENTS

| DE | 243930 | 3/1987 |
| EP | 0207004 | 12/1986 |
| EP | 1 004 241 | 5/2000 |
| EP | 1 454 903 | 9/2004 |
| EP | 1 616 866 | 1/2006 |
| EP | 1 632 484 | 3/2006 |
| EP | 1 671 957 | 6/2006 |

(Continued)

OTHER PUBLICATIONS

U.S. Appl. No. 60/620,048 to Hans et al., filed Oct. 19, 2004.

(Continued)

*Primary Examiner*—Laura L. Stockton
(74) *Attorney, Agent, or Firm*—Greenblum & Bernstein, P.L.C.

(57) ABSTRACT

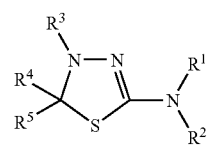

(I)

(wherein $R^1$ and $R^4$ are the same or different and each represents a hydrogen atom, substituted or unsubstituted lower alkyl, substituted or unsubstituted lower alkynyl, substituted or unsubstituted lower alkenyl, or the like; $R^5$ represents a substituted or unsubstituted heterocyclic group, substituted or unsubstituted aryl, or the like; $R^2$ represents $—C(=W)R^6$ or the like; $R^3$ represents a hydrogen atom, $—C(=W^4)R^{6A}$, or the like)

Antitumor agents which comprises a thiadiazoline derivative represented by the aforementioned general formula (I) or a pharmacologically acceptable salt thereof as an active ingredient are provided.

12 Claims, No Drawings

FOREIGN PATENT DOCUMENTS

| | | |
|---|---|---|
| EP | 1 867 640 | 12/2007 |
| EP | 1 870 404 | 12/2007 |
| JP | 62-053976 | 3/1987 |
| JP | 8-34734 | 2/1996 |
| JP | 2000-159756 | 6/2000 |
| JP | 2000-204077 | 7/2000 |
| JP | 2000-229959 | 8/2000 |
| WO | 0 217 519 | 4/1987 |
| WO | 93/22311 | 11/1993 |
| WO | 00/42029 | 7/2000 |
| WO | 01/30768 A1 | 5/2001 |
| WO | 01/56994 | 8/2001 |
| WO | 01/98278 | 12/2001 |
| WO | 02/056880 | 7/2002 |
| WO | 02/057244 | 7/2002 |
| WO | 02/067939 A1 | 9/2002 |
| WO | 02/079149 | 10/2002 |
| WO | 02/079169 | 10/2002 |
| WO | 03/039460 A2 | 5/2003 |
| WO | 03/051854 A1 | 6/2003 |
| WO | 03/079973 | 10/2003 |
| WO | 2004/039774 A2 | 5/2004 |
| WO | 2004/092147 A1 | 10/2004 |
| WO | 2004/111023 A1 | 12/2004 |
| WO | 2004/111024 A1 | 12/2004 |
| WO | 2005/035512 A1 | 4/2005 |
| WO | 2006/044825 A2 | 4/2006 |
| WO | 2006/101102 | 9/2006 |
| WO | 2006/101102 A1 | 9/2006 |
| WO | 2006/101103 | 9/2006 |
| WO | 2006/101103 A1 | 9/2006 |
| WO | 2006/137490 A1 | 9/2006 |
| WO | 2006/137490 | 12/2006 |

OTHER PUBLICATIONS

M.A. Khalil et al., Arch. Pharm. (Weinheim), vol. 326, 1993, pp. 489-492.
A.A. Farghaly et al., Arch. Pharm. Pharm. Med. Chem., vol. 333, No. 2-3, 2000, pp. 53-57.
El-S.M. El-Khawass et al., Alexandria Journal of Pharmaceutical Sciences, vol. 4, No. 1, 1990, pp. 77-79.
H.M. Mokhtar et al., Bull. Pharm. Sci., Assiut University, vol. 18, Part 2, Dec. 1995, pp. 59-67.
M.A. Khalil, Alexandria J. of Pharm. Sciences, vol. 3, No. 2, 1989, pp. 221-224.
L.L. Awad et al., Alexandria J. of Pharm. Sci., vol. 3, No. 2, 1989, pp. 119-121.
S.Y. Hassan et al., J. Saudi Chem. Soc., vol. 3, No. 2, 1999, pp. 171-176.
T.-B. Huang et al., Phosphorus, Sulfur and Silicon, vol. 122, 1997, pp. 307-312.
B. Schulze et al., Zeitschrift fuer Chemie, vol. 29, No. 5, 1989, pp. 166-167.
T. Hoque et al., J. Bangladesh Chem. Soc., vol. 5, 1992, pp. 127-132.
S. Kubota et al., J. Org. Chem., vol. 45, 1980, pp. 1473-1477.
E.V. Tao et al., J. Heterocyclic Chem., vol. 21, 1984, pp. 599-601.
S. Kubota et al., Heterocycles, vol. 4, 1976, pp. 1909-1912.
A. Wengel et al., Pestic. Sci., vol. 30, 1990, pp. 223-233.
E.E. Ycoba et al., Khim. Geterotsikl. Soedin., vol. 10, 1994, pp. 1337-1344.
S. Kubota et al., J. Chem. Soc., Chem. Commun., 1982, pp. 901-902.
Y. Nakayama et al., J. Org. Chem., vol. 49, 1984, pp. 1703-1707.
E.V. Tao et al., Heterocycles, vol. 29, 1989, pp. 133-140.
L. Somogyi, Tetrahedron, vol. 47, 1991, pp. 9305-9316.
L. Somogyi et al., Tetrahedron, vol. 48, 1992, pp. 9355-9362.
Khim. Geterotsiki. Soedin, vol. 12, 1992, pp. 1689-1697.
S. Andreae et al., Journal f. prakt. Chemie., vol. 328, 1986, Heft 2, pp. 205-214.
L. Somogyi, Liebigs Ann. Chem., 1994, pp. 623-627.
L. Somogyi, Liebigs Ann., 1995, pp. 721-724.
Z.M. Nofal et al., Arch. Pharm. Res., vol. 25, 2002, pp. 250-257.
S. Kabilan et al., Asian Journal of Chemistry, vol. 14, 2002, pp. 879-883.
M.A.M. Alho et al., Arkivoc 2000, vol. 1, pp. 627-640.
K.N. Zelenin et al., Chemistry of Heterocyclic Compounds, vol. 35, 1999, pp. 87-92.
I.V.U. Zavedenii, Khimiya I Khimicheskaya Takhnologiya, vol. 43, 2000, pp. 64-68.
N.S. Habib et al., Alex. J. Pharm. Sci., vol. 10, 1996, pp. 53-58.
F.A. Ashour et al., Bull. Fac. Pharm. Cairo Univ., vol. 31, 1993, pp. 381-386.
M.H. Khan et al., J. Pesticide Sci., vol. 19, 1994, pp. 305-308.
Dokl. Aka. Nauk SSSR, vol. 296, 1987, pp. 1133-1137.
Zhurnal Organicheskoi Khimii, 1986, pp. 663-664.
R.J. Kuban et al., Cryst. Res. Technol., vol. 22, 1987, pp. 799-802.
K.N. Thimmaiah et al., Inorganica Chimica Acta, vol. 107, 1985, pp. 1-4.
H. Graubaum et al., Z. Chem., vol. 26, 1986, pp. 99-100.
CAS Registry No. 443105-88-2, 443105-83-7, 443105-78-0, 443105-73-5, 443105-64-4, 443105-56-4, 443105-51-9, 443105-46-2, 443105-41-7, 443105-34-8, 442654-91-3, 438540-30-8, 433235-71-3, 432536-58-8, 432518-92-8, 419551-57-8, 405925-79-3, 400833-35-4, 356773-31-4, 356773-12-1, 355435-20-0, 352225-16-2, 332389-28-3,.332389-25-0, 89992-30-3, 356773-98-3, 356773-79-0, 356773-13-2, 350581-79-2, 346715-36-4, 332389-27-2, 330683-67-5, 330683-65-3, 313558-45-1, 313548-79-7, 313523-91-0, 313523-88-5, 307332-32-7, 307332-31-6, 307332-30-5, 307332-29-2, 307332-28-1, 307332-24-7, 307332-22-5, 300808-92-8, 300719-38-4, 298218-64-1, 296801-28-0, 292066-09-2, 332389-24-9, 332389-23-8, 198069-12-4, 149638-52-8, 149638-50-6, 149638-48-2, 149638-46-0, 149638-44-8,149638-42-6.
Yun Ding et al., "Syntheses and Anticancer Activity of Ribonucleoside Analogues Containing Thio-Substituted Fice Membered Heterocyclic Base", Bioorganic and Medicinal Chemistry Letters, vol. 7, No. 13, pp. 1607-1610 (1997).
Kubota, S., et al. "Novel Rearrangement of 3-acyl-5-acylamino-2,3-dihydro-1,3,4-thiadiazole 1-oxides into 1,3,4-oxadiazoles" Heterocycles, vol. 24, No. 1, 1986, pp. 21-24.
Schenone, S., et al. "3-Arylsulphonyl-5-arylamino-1,3,4-thiadiazol-2(3*H*)ones as Anti-inflammatory and Analgesic Agents", Bioorganic and Medicinal Chemistry, 9, 2001, pp. 2149-2153.
Bhalla, M., et al. "Benzopyran-2-one derivatives: anti-inflammatory, analgesic and antiproteolytic agents" European Journal of Medicinal Chemistry, 29, 1994, pp. 713-717.
Blangy, A., et al., Cell, vol. 83, 1995, pp. 1159-1169.
Kapoor, T. M., et al., The Journal of Cell Biology, vol. 150, 2000, pp. 975-988.
Kapoor, T. M., et al., Proceedings of the National Academy of Sciences USA, vol. 96, 1999, pp. 9106-9111.
Lockhart, A. et al., Biochemistry, vol. 35, 1996, pp. 2365-2373.
Turner, J., et al., The Journal of Biological Chemistry, vol. 276, 2001, pp. 25496-25502.
Maliga, Z. et al., Chemistry and Biology, vol. 9, 2002, pp. 989-996.
Su, A., et al., Proceedings of the National Academy of Sciences USA, vol. 99, No. 7, 2002, pp. 4465-4470.
Mayer, T. U., et al., Science, vol. 286, 1999, pp. 971-974.
Mandelkow, E, et al., Trends in Cell Biology, vol. 12, 2002, pp. 585-591.
B. G. Szczepankiewicz et al., J. Med. Chem., 2001, vol. 44, No. 25, pp. 4416-4430.
S. M. Hassan et al., J. Chem. Research Synopses, 2000, vol. 12, pp. 544-545 and pp. 1301-1315.
K. N. Zelenin et al., Zhurnal Organicheskoi Khimii, 1984, vol. 20, No. 1, pp. 152-162.
D.M. Evans et al., Journal of the Chemical Society, Perkin Transactions 1, 1986, vol. 8, pp. 1499-1505.
English language abstract of JP 2000-229559, published Aug. 22, 2000.
Zelenin et al, Chemical Abstracts, 1982, vol. 97, No. 19, p. 708, Abstract No. 162778w.
Agarwal et al. *Nature Reviews Cancer* 3:502-16, 2003.
Power et al. *J. Chem. Soc. Chem. Commun.* 8:873-74, 1998.
Daub et al., *Nature Reviews Drug Discovery* 3:1001-10, 2004.

Ross, R. *Nature* 362:801-09, 1993.
English Language Abstract of JP 8-34734. Feb. 1996.
English Language Abstract of JP 2000-159756, Jun. 2000.
Jikken Igaku (*Experimental Medicine*) 17(4):439-44, 1999.
Moses et al. *N. Engl. J. Med.* 349(14):1315-23, 2003.
Serruys et al. *N. Engl. J. Med.* 331(8):489-95, 1994.
Shin-Jikken-Kagaku-Koza, 14:1142-45 (Maruzen 1978).
Stone et al. *N. Engl. J. Med.* 350(3):221-31, 2004.
Temple et al. *J. Med. Chem.*, 25:1045-50, 1982.
Commonly assigned, copending U.S. Appl. No. 11/909,289 (Murakata et al.) entitled "Therapeutic Agent for Hematopoietic Tumor". Sep. 21, 2007.
Commonly assigned, copending U.S. Appl. No. 11/909,324 (Nakai et al.) entitled "Therapeutic Agent for Hematopoietic Tumor" Sep. 21, 2007.
Commonly assigned, copending U.S. Appl. No. 11/993,757 (Nakai et al.) entitled "Therapeutic Agent for Restenonsis". Dec. 21, 2007.
Yinglin et al. *Synthesis* 28:615-618, 1990.
Zelenin et al., CA 119:202821, 1993.
CA Registry No. 400873-00-9, indexed in Registry file on STN on Mar. 14, 2002.
CA Registry No. 400833-35-4, indexed in Registry file on STN on Mar. 14, 2002.
CA Registry No. 385382-44-5, indexed in Registry file on STN on Jan. 22, 2002.
CA Registry No. 382174-71-2, indexed in Registry file on STN on Jan. 11, 2002.
CA Registry No. 443105-88-2, indexed in Registry file on STN on Aug. 8, 2002.
CA Registry No. 443105-51-9, indexed in Registry file on STN on Aug. 8, 2002.
CA Registry No. 443105-41-7, indexed in Registry file on STN on Aug. 8, 2002.
CA Registry No. 443105-34-8, indexed in Registry file on STN on Aug. 8, 2002.
CA Registry No. 443105-23-5, indexed in Registry file on STN on Aug. 8, 2002.
CA Registry No. 416841-95-7, indexed in Registry file on STN on May 16, 2002.
CA Registry No. 416841-94-6, indexed in Registry file on STN on May 16, 2002.
CA Registry No. 405925-80-6, indexed in Registry file on STN on Apr. 18, 2002.
CA Registry No. 401945-66-2, indexed in Registry file on STN on Mar. 20, 2002.
CA Registry No. 401945-63-9, indexed in Registry file on STN on Mar. 20, 2002.
CA Registry No. 400873-06-5, indexed in Registry file on STN on Mar. 14, 2002.
CA Registry No. 332055-94-4, indexed in Registry file on STN on Apr. 23, 2001.
CA Registry No. 329689-25-0, indexed in Registry file on STN on Apr. 2, 2001.
CA Registry No. 329689-21-6, indexed in Registry file on STN on Apr. 2, 2001.
CA Registry No. 329689-19-2, indexed in Registry file on STN on Apr. 2, 2001.
CA Registry No. 312597-81-2, indexed in Registry file on STN on Jan. 3, 2001.
CA Registry No. 312597-80-1, indexed in Registry file on STN on Jan. 3, 2001.
CA Registry No. 312597-79-8, indexed in Registry file on STN on Jan. 3, 2001.
CA Registry No. 312597-76-5, indexed in Registry file on STN on Jan. 3, 2001.
CA Registry No. 309927-68-2, indexed in Registry file on STN on Dec. 20, 2000.
CA Registry No. 298218-65-2, indexed in Registry file on STN on Oct. 23, 2000.
CA Registry No. 296801-28-0, indexed in Registry file on STN on Oct. 18, 2000.
CA Registry No. 356773-74-5, indexed in Registry file on STN on Sep. 14, 2001.
CA Registry No. 356773-69-8, indexed in Registry file on STN on Sep. 14, 2001.
CA Registry No. 356773-42-7, indexed in Registry file on STN on Sep. 14, 2001.
CA Registry No. 356773-31-4, indexed in Registry file on STN on Sep. 14, 2001.
CA Registry No. 356773-11-0, indexed in Registry file on STN on Sep. 14, 2001.
CA Registry No. 355435-20-0, indexed in Registry file on STN on Sep. 10, 2001.
CA Registry No. 353466-59-8, indexed in Registry file on STN on Aug. 29, 2001.
CA Registry No. 352225-16-2, indexed in Registry file on STN on Aug. 21, 2001.
CA Registry No. 344872-11-3, indexed in Registry file on STN on Jul. 8, 2001.
CA Registry No. 337501-59-4, indexed in Registry file on STN on May 23, 2001.
CA Registry No. 337501-55-0, indexed in Registry file on STN on May 23, 2001.
CA Registry No. 337501-53-8, indexed in Registry file on STN on May 23, 2001.
CA Registry No. 337501-51-6, indexed in Registry file on STN on May 23, 2001.
CA Registry No. 332389-30-7, indexed in Registry file on STN on Apr. 25, 2001.
CA Registry No. 332389-28-3, indexed in Registry file on STN on Apr. 25, 2001.
CA Registry No. 332389-25-0, indexed in Registry file on STN on Apr. 25, 2001.
Grachev et al., Journal of Applied Spectroscopy (2000), 67(3), pp. 461-466.
Saha et al., CA 117:171340, 1992.
Golub et al., Science, vol. 286, Oct. 15, 1999, pp. 531-537.

THIADIAZOLINE DERIVATIVE

CROSS-REFERENCE TO RELATED APPLICATIONS

This application is a divisional of application Ser. No. 10/497,531, filed Mar. 28, 2005, now U.S. Pat. No. 7,425,636 which is a National Stage Application of International Application No. PCT/JP02/12961, filed Dec. 11, 2002, which was not published in English under PCT Article 21(2), entering the National Stage on Jun. 10, 2004, and which claims priority of Japanese Application Nos. 2001-377456, filed Dec. 11, 2001 and 2002-237399, filed Aug. 16, 2002. The entire disclosure of application Ser. No. 10/497,531 is considered as being part of this application, and the entire disclosure of application Ser. No. 10/497,531 is expressly incorporated by reference herein in its entirety.

TECHNICAL FIELD

The present invention relates to an antitumor agent comprising a thiadiazoline derivative or a pharmacologically acceptable salt thereof as an active ingredient, and a thiadiazoline derivative or a pharmacologically acceptable salt thereof which is useful for therapeutic treatment of a tumor.

BACKGROUND ART

In chemotherapies of cancers, a variety of anticancer agents including antimitotic agents such as taxane and vinca alkaloid, topoisomerase inhibitors, alkylating agents and the like have been used. These agents have side effects such as bone marrow toxicity and neuropathy, a problem of drug resistance and the like. Therefore, novel anticancer agents which have improvement in the above problems have so far been desired.

It is known that thiadiazoline derivatives have inhibitory activity against transcription factor STAT6 activation, antagonistic action of integrin, and the control of insect or acarid pests (Japanese Published Unexamined Patent Application No. 2000-229959, WO01/56994, U.S. Pat. No. 6,235,762). In addition, it is known that the derivatives have antibacterial activity, ACE inhibitory activity and the like [J. Bangladesh Chem. Soc., Vol. 5, p. 127 (1992), WO93/22311, Japanese Published Unexamined Patent Application No. 62-53976 (1987)].

DISCLOSURE OF THE INVENTION

An object of the present invention is to provide a thiadiazoline derivative or a pharmacologically acceptable salt thereof which is useful for therapeutic treatment of a human malignant tumor, for example, breast cancer, gastric cancer, ovarian cancer, colon cancer, lung cancer, brain tumor, laryngeal cancer, hematological cancer, urinary or genital tumor including bladder cancer and prostatic cancer, renal cancer, skin carcinoma, hepatic carcinoma, pancreatic cancer, a uterine cancer, or the like. Another object of the present invention is to provide an antitumor agent comprising a thiadiazoline derivative or a pharmacologically acceptable salt thereof as an active ingredient.

The present invention relates to the following (1) to (43).

(1) An antitumor agent which comprises a thiadiazoline derivative represented by the general formula (I) or a pharmacologically acceptable salt thereof as an active ingredient

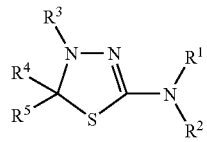

<wherein $R^1$ and $R^4$ are the same or different and each represents
a hydrogen atom, substituted or unsubstituted lower alkyl, substituted or unsubstituted lower alkynyl, substituted or unsubstituted lower alkenyl, substituted or unsubstituted cycloalkyl, a substituted or unsubstituted heterocyclic group, or substituted or unsubstituted aryl;

$R^2$ represents
a hydrogen atom, substituted or unsubstituted lower alkyl, substituted or unsubstituted lower alkynyl, substituted or unsubstituted lower alkenyl, substituted or unsubstituted cycloalkyl,
—C(=W)$R^6$ [wherein
W represents
an oxygen atom or a sulfur atom
$R^6$ represents
a hydrogen atom, substituted or unsubstituted lower alkyl, substituted or unsubstituted lower alkenyl, substituted or unsubstituted cycloalkyl, a substituted or unsubstituted aryl, a substituted or unsubstituted heterocyclic group,
—NR$^7$R$^8$ (wherein
$R^7$ and $R^8$ are the same or different and each represents
a hydrogen atom, substituted or unsubstituted lower alkyl, substituted or unsubstituted lower alkenyl, substituted or unsubstituted cycloalkyl, substituted or unsubstituted aryl, or a substituted or unsubstituted heterocyclic group, or
$R^7$ and $R^8$ are combined together with the adjacent nitrogen atom to form a substituted or unsubstituted heterocyclic group),
—OR$^9$ (wherein
$R^9$ represents
substituted or unsubstituted lower alkyl, substituted or unsubstituted lower alkenyl, substituted or unsubstituted cycloalkyl, or substituted or unsubstituted aryl) or
—SR$^{10}$ (wherein
$R^{10}$ represents
substituted or unsubstituted lower alkyl, substituted or unsubstituted lower alkenyl, or substituted or unsubstituted aryl)]
—NR$^{11}$R$^{12}$ {wherein
$R^{11}$ and $R^{12}$ are the same or different and each represents
a hydrogen atom, substituted or unsubstituted lower alkyl, substituted or unsubstituted lower alkenyl, substituted or unsubstituted cycloalkyl, or
—C(=O)R$^{13}$ [wherein
$R^{13}$ represents
substituted or unsubstituted lower alkyl, substituted or unsubstituted lower alkenyl, substituted or unsubstituted aryl, a substituted or unsubstituted heterocyclic group, —NR$^{7A}$R$^{8A}$ (wherein R$^{7A}$ and R$^{8A}$ have the same meanings as those of the aforementioned R$^7$ and R$^8$, respectively), or
—OR$^{9A}$ (wherein R$^{9A}$ has the same meaning as that of the aforementioned R$^9$)]} or
—SO$_2$R$^{14}$ (wherein
R$^{14}$ represents
substituted or unsubstituted lower alkyl, substituted or unsubstituted lower alkenyl, substituted or unsubstituted aryl, or a substituted or unsubstituted heterocyclic group), or R$^1$ and R$^2$ are combined together with the adjacent nitrogen atom to form a substituted or unsubstituted heterocyclic group, R$^5$ represents
substituted or unsubstituted lower alkyl, substituted or unsubstituted lower alkynyl, substituted or unsubstituted lower alkenyl, substituted or unsubstituted cycloalkyl, a substituted or unsubstituted heterocyclic group, or substituted or unsubstituted aryl, or R$^4$ and R$^5$ are combined together to represent
—(CR$^{28}$R$^{29}$)$_{m1}$-Q-(CR$^{28A}$R$^{29A}$)$_{m2}$— {wherein
Q represents
a single bond, substituted or unsubstituted phenylene, or cycloalkylene,
m1 and m2 are the same or different and each represents an integer of from 0 to 4, with the proviso that m1 and m2 are not 0 at the same time,
R$^{28}$, R$^{29}$, R$^{28A}$ and R$^{29A}$ are the same or different and each represents a hydrogen atom, substituted or unsubstituted lower alkyl,
—OR$^{30}$ [wherein
R$^{30}$ represents
a hydrogen atom, substituted or unsubstituted lower alkyl, substituted or unsubstituted lower alkenyl, —CONR$^{31}$R$^{32}$ (wherein
R$^{31}$ and R$^{32}$ are the same or different and each represents
a hydrogen atom, substituted or unsubstituted lower alkyl, a substituted or unsubstituted heterocyclic group, or substituted or unsubstituted aryl),
—SO$_2$NR$^{33}$R$^{34}$ (wherein
R$^{33}$ and R$^{34}$ are the same or different and each represents
a hydrogen atom, substituted or unsubstituted lower alkyl, a substituted or unsubstituted heterocyclic group, or substituted or unsubstituted aryl), or
—COR$^{35}$ (wherein
R$^{35}$ represents
a hydrogen atom, substituted or unsubstituted lower alkyl, a substituted or unsubstituted heterocyclic group, or substituted or unsubstituted aryl)],
—NR$^{36}$R$^{37}$ [wherein
R$^{36}$ and R$^{37}$ are the same or different and each represents
a hydrogen atom, substituted or unsubstituted lower alkyl, —COR$^{38}$ (wherein
R$^{38}$ represents
a hydrogen atom, substituted or unsubstituted lower alkyl, a substituted or unsubstituted heterocyclic group, substituted or unsubstituted aryl, substituted or unsubstituted lower alkoxy, substituted or unsubstituted aryloxy, amino, substituted or unsubstituted lower alkylamino, substituted or unsubstituted di(lower alkyl)amino, or substituted or unsubstituted arylamino), or
—SO$_2$R$^{39}$ (wherein
R$^{39}$ represents
substituted or unsubstituted lower alkyl, a substituted or unsubstituted heterocyclic group, or substituted or unsubstituted aryl)], or
—CO$_2$R$^{40}$ (wherein
R$^{40}$ represents
a hydrogen atom, substituted or unsubstituted lower alkyl, or substituted or unsubstituted aryl), and when m1 or m2 is an integer of 2 or more, each R$^{28}$, R$^{29}$, R$^{28A}$ and R$^{29A}$ may be the same or different, respectively, and any two of R$^{28}$, R$^{29}$, R$^{28A}$ and R$^{29A}$ which are bound to the adjacent two carbon atoms may be combined to form a bond}, and R$^3$ represents
a hydrogen atom or
—C(=W$^A$)R$^{6A}$ (wherein W$^A$ and R$^{6A}$ have the same meanings as those of the aforementioned W and R$^6$, respectively)>.

(2) The antitumor agent according to the aforementioned (1), wherein R$^4$ is substituted or unsubstituted lower alkyl, substituted or unsubstituted lower alkynyl, substituted or unsubstituted lower alkenyl, substituted or unsubstituted cycloalkyl, a substituted or unsubstituted heterocyclic group, or substituted or unsubstituted aryl, and R$^5$ is substituted or unsubstituted cycloalkyl, a substituted or unsubstituted heterocyclic group, or substituted or unsubstituted aryl, or R$^4$ and R$^5$ are combined to represent —(CR$^{28}$R$^{29}$)$_{m1}$-Q-(CR$^{28A}$R$^{29A}$)$_{m2}$—.

(3) The antitumor agent according to the aforementioned (1), wherein R$^5$ is substituted or unsubstituted lower alkyl, substituted or unsubstituted lower alkynyl, substituted or unsubstituted lower alkenyl, or substituted or unsubstituted cycloalkyl.

(4) The antitumor agent according to the aforementioned (1) or (2), wherein R$^5$ is substituted or unsubstituted aryl, or a substituted or unsubstituted heterocyclic group.

(5) The antitumor agent according to the aforementioned (1) or (2), wherein R$^5$ is substituted or unsubstituted phenyl, or substituted or unsubstituted thienyl.

(6) The antitumor agent according to any one of the aforementioned (1) to (6), wherein R$^4$ is substituted or unsubstituted lower alkyl.

(7) The antitumor agent according to the aforementioned (1), wherein R$^4$ and R$^5$ are combined to represent —(CR$^{28}$R$^{29}$)$_{m1}$-Q-(CR$^{28A}$R$^{29A}$)$_{m2}$—.

(8) The antitumor agent according to the aforementioned (1), wherein R$^4$ and R$^5$ are combined to represent —(CH$_2$)$_{m1}$-Q-(CH$_2$)$_{m2}$—.

(9) The antitumor agent according to the aforementioned (7) or (8), wherein Q is substituted or unsubstituted phenylene.

(10) The antitumor agent according to any one of the aforementioned (1) to (9), wherein R$^1$ is a hydrogen atom, or substituted or unsubstituted lower alkyl.

(11) The antitumor agent according to any one of the aforementioned (1) to (9), wherein R$^1$ is a hydrogen atom.

(12) The antitumor agent according to any one of the aforementioned (1) to (11), wherein R$^2$ is —C(=W)R$^6$.

(13) The antitumor agent according to the aforementioned (12), wherein R$^6$ is substituted or unsubstituted lower alkyl, substituted or unsubstituted lower alkynyl, substituted or unsubstituted lower alkenyl, or substituted or unsubstituted cycloalkyl.

(14) The antitumor agent according to the aforementioned (12) or (13), wherein W is an oxygen atom.

(15) The antitumor agent according to any one of the aforementioned (1) to (9), wherein $R^1$ and $R^2$ are combined to form a substituted or unsubstituted heterocyclic group together with the adjacent nitrogen atom.

(16) The antitumor agent according to any one of the aforementioned (1) to (15), wherein $R^3$ is —C(=$W^4$)$R^{6A}$.

(17) The antitumor agent according to the aforementioned (16), wherein $R^{6A}$ is substituted or unsubstituted lower alkyl, substituted or unsubstituted lower alkynyl, substituted or unsubstituted lower alkenyl, or substituted or unsubstituted cycloalkyl.

(18) The antitumor agent according to the aforementioned (16), wherein $R^{6A}$ is lower alkyl.

(19) The antitumor agent according to any one of the aforementioned (16) to (18), wherein $W^4$ is an oxygen atom.

(20) A thiadiazoline derivative represented by the general formula (IA) or a pharmacologically acceptable salt thereof:

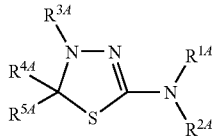

(IA)

{wherein $R^{1A}$, $R^{2A}$, $R^{3A}$, $R^{4A}$ and $R^{5A}$ have the same meanings as those of the aforementioned $R^1$, $R^2$, $R^3$, $R^4$ and $R^5$, respectively, with the proviso that when $R^{2A}$ and $R^{3A}$ are the same to be —CONHR$^{8B}$ (wherein $R^{8B}$ represents a substituted or unsubstituted lower alkyl, or substituted or unsubstituted aryl), and
  (i) $R^{4A}$ is a hydrogen atom, or
  (ii) one of $R^{4A}$ and $R^{5A}$ is substituted or unsubstituted lower alkyl, then the other of $R^{4A}$ and $R^{5A}$ only represents substituted or unsubstituted cycloalkyl, substituted or unsubstituted lower alkenyl, or substituted or unsubstituted lower alkynyl

[provided that
  (a) when $R^{1A}$, $R^{2A}$ and $R^{3A}$ are hydrogen atoms, and one of $R^{4A}$ and $R^{5A}$ is methyl,
    the other of $R^{4A}$ and $R^{5A}$ is not any of phenyl, 4-nitrophenyl, 4-aminophenyl, 4-bromophenyl, 3-nitrophenyl and 4-methoxy-3-nitrophenyl,
  (b) when $R^{1A}$ and $R^{2A}$ are hydrogen atoms, $R^{3A}$ is acetyl,
    (i) and one of $R^{4A}$ and $R^{5A}$ is methyl,
      the other of $R^{4A}$ and $R^{5A}$ is not any of methyl, ethyl, phenyl, 4-methoxyphenyl, 2-naphthylsulfonylmethyl, 4-bromophenylsulfonylmethyl and 4-chlorophenylsulfonylmethyl, and
    (ii) and $R^{4A}$ is a hydrogen atom,
      $R^{5A}$ is not any of phenyl, 4-nitrophenyl, 4-chlorophenyl, 4-methoxyphenyl, 4-dimethylaminophenyl and pyridyl,
  (c) when $R^{1A}$ is a hydrogen atom, $R^{2A}$ and $R^{3A}$ are acetyl,
    (i) and one of $R^{4A}$ and $R^{5A}$ is methyl,
      the other of $R^{4A}$ and $R^{5A}$ is not any of methyl, ethyl, propyl, butyl, hexyl, heptyl, phenyl, benzyl, acetylmethyl, tert-butoxycarbonylmethyl, ethoxycarbonylmethyl, 4-bromophenylsulfonylmethyl, 4-bromophenylsulfonylethyl, 4-chlorophenylsulfonylmethyl, 3,4-dichlorophenylsulfonylmethyl, 3,4-dichlorophenylsulfonylethyl, 3,4-dimethylphenylsulfonylmethyl, phenylsulfonylmethyl, 4-methylphenylsulfonylmethyl, 4-methylphenylsulfonylethyl, 4-(acetylamino)phenylsulfonylethyl, 4-bromophenylsulfonylethyl, 2-(4-methylphenylsulfonyl)-2-phenylethyl, 2-(4-methylphenylthio)-2-phenylethyl, 2-naphthylsulfonylethyl, 2-naphthylsulfonylmethyl, phenethyl, 3-benzoyloxyphenyl, 2-oxo-2H-1-benzopyran-3-yl, 2-furyl, 5-nitro-2-furyl, 5-methyl-2-furyl, 2-thienyl, 5-chloro-2-thienyl, 3-acetoxyphenyl, 3-nitrophenyl, 4-nitrophenyl, 4-fluorophenyl, 3-acetylaminophenyl, 4-methoxyphenyl, 3-methoxyphenyl, 4-ethylphenyl, 4-methylphenyl, 4-bromophenyl, 4-nonyloxyphenyl, 4-phenylphenyl, 3,4-dimethoxyphenyl, 1,3-benzodioxol-5-yl, 4-(benzimidazol-2-ylamino)phenyl, 4-(1-methylbenzimidazol-2-ylamino)phenyl, 3-pyridyl, 2-naphthyl, 2-acetylamino-4-acetyl-1,3,4-thiadiazolin-5-yl and 4-acetylaminophenylsulfonylmethyl,
    (ii) and one of $R^{4A}$ and $R^{5A}$ is phenyl,
      the other of $R^{4A}$ and $R^{5A}$ is not any of phenyl, 4-methoxyphenyl, 3,4-dimethoxyphenyl, 4-nitrophenyl, ethoxycarbonylmethyl, isobutyl, sec-butyl, n-butyl and acetylaminomethyl,
    (iii) and one of $R^{4A}$ and $R^{5A}$ is 2-acetoxyphenyl,
      the other of $R^{4A}$ and $R^{5A}$ is not 2-phenylethenyl,
    (iv) and $R^{4A}$ is a hydrogen atom or 4-methoxyphenyl,
      $R^{5A}$ is not 4-methoxyphenyl,
    (v) and $R^{4A}$ is a hydrogen atom,
      $R^{5A}$ is not any of phenyl, 4-nitrophenyl, 4-chlorophenyl, 4-dimethylaminophenyl and pyridyl,
    (vi) and $R^{4A}$ and $R^{5A}$ are combined to represent —(CH$_2$)$_{m1}$-Q-(CH$_2$)$_{m2}$— (wherein m1, m2 and Q have the same meanings as those of the aforementioned, respectively),
      —(CH$_2$)$_{m1}$-Q-(CH$_2$)$_{m2}$— wherein Q is a single bond and the sum of m1 and m2 is 5, is excluded
    (vii) and one of $R^{4A}$ and $R^{5A}$ is 1,2,3-triacetoxypropyl, the other of $R^{4A}$ and $R^{5A}$ is not 3,4-dihydro-3-oxo-2-quinoxalinyl, and
    (viii) and one of $R^{4A}$ and $R^{5A}$ is ethyl, the other of $R^{4A}$ and $R^{5A}$ is not ethyl,
  (d) when $R^{1A}$ and $R^{4A}$ are hydrogen atoms, and
    (i) $R^{2A}$ and $R^{3A}$ are the same to be propionyl or benzoyl or
    (ii) $R^{2A}$ is propionyl and $R^{3A}$ is acetyl,
      $R^{5A}$ is not phenyl,
  (e) when $R^{1A}$ and $R^{3A}$ are hydrogen atoms,
    $R^{2A}$ is acetyl, and
    one of $R^{4A}$ and $R^{5A}$ is methyl,
      the other of $R^{4A}$ and $R^{5A}$ is not either of phenyl and 3,4-dichlorophenylsulfonylethyl,
  (f) when $R^{1A}$ is phenyl, $R^{2A}$ and $R^{3A}$ are acetyl,
    (i) and one of $R^{4A}$ and $R^{5A}$ is methyl, the other of $R^{4A}$ and $R^{5A}$ is not either of 4-acetoxy-6-methyl-2-oxo-2H-pyran-3-yl and 2-oxo-2H-1-benzopyran-3-yl, and
    (ii) and $R^{4A}$ is phenyl,
      $R^{5A}$ is not phenyl,
  (g) when $R^{1A}$ is methyl, $R^{2A}$ and $R^{3A}$ are acetyl,
    (i) and $R^{4A}$ is a hydrogen atom,
      $R^{5A}$ is not phenyl,
    (ii) and one of $R^{4A}$ and $R^{5A}$ is methyl,
      the other of $R^{4A}$ and $R^{5A}$ is not either of ethoxycarbonylethyl and ethoxycarbonylpropyl,
  (h) when $R^{1A}$, $R^{2A}$ and $R^{4A}$ are methyl, and $R^{5A}$ is pyridyl, $R^{3A}$ is not —$COR^C$ (wherein $R^C$ represents methyl, chloromethyl, methoxy, ethoxycarbonylmethyl or ethoxycarbonylethenyl), (j) when one of $R^{1A}$ and $R^{2A}$ is a hydrogen atom,
the other of $R^{1A}$ and $R^{2A}$ is ethyl, and
$R^{3A}$ is a hydrogen atom or acetyl,
$R^{4A}$ and $R^{5A}$ are not methyl at the same time, (k) when $R^{1A}$ is 4-chlorophenyl,
$R^{2A}$ is a hydrogen atom, and
one of $R^{4A}$ and $R^{5A}$ is methyl,
the other of $R^{4A}$ and $R^{5A}$ is not (1-methylbenzimidazol-2-ylamino)phenyl, and
$R^{3A}$ is not acetyl, (m) when $R^{1A}$ is phenyl, 4-chlorophenyl, 4-methylphenyl or 4-methoxyphenyl,
$R^{2A}$ is a hydrogen atom, and
$R^{4A}$ and $R^{5A}$ are methyl,
$R^{3A}$ is not any of acetyl, 4-chlorophenoxyacetyl, 2-chlorophenoxyacetyl, 3-methylphenoxyacetyl and phenylaminocarbonyl, (n) when $R^{2A}$ and $R^{3A}$ are acetyl,
one of $R^{4A}$ and $R^{5A}$ is methyl,
(i) and the other of $R^{4A}$ and $R^{5A}$ is 1H-benzotriazol-1-ylmethyl,
$R^{1A}$ is not any of cyclohexyl, benzyl, phenyl, 2-methylphenyl and 4-methoxyphenyl,
(ii) and the other of $R^{4A}$ and $R^{5A}$ is 2-methylbenzimidazol-1-ylmethyl or 2-ethylbenzimidazol-1-ylmethyl,
$R^{1A}$ is not any of cyclohexyl, phenyl and 4-bromophenyl, (o) when $R^{1A}$ is a hydrogen atom,
$R^{2A}$ is acetyl, and
$R^{4A}$ and $R^{5A}$ are methyl,
$R^{3A}$ is not benzoyl, (p) when one of $R^{1A}$ and $R^{2A}$ is hydrogen atom,
the other of $R^{1A}$ and $R^{2A}$ is methyl, and
$R^{4A}$ and $R^{5A}$ are both methyl or both ethyl,
$R^{3A}$ is not any of acetyl, benzoyl, pivaloyl, 3-nitrobenzoyl, 2-fluorobenzoyl, 4-fluorobenzoyl, 2-trifluoromethylbenzoyl and 3-trifluoromethylbenzoyl, and (q) when $R^{1A}$ is methyl,
$R^{2A}$ is methylaminocarbonyl, and
$R^{4A}$ and $R^{5A}$ are both methyl or both ethyl,
$R^{3A}$ is not any of acetyl, benzoyl, pivaloyl, 2-fluorobenzoyl, 4-fluorobenzoyl, 2-trifluoromethylbenzoyl, 3-trifluoromethylbenzoyl and 4-trifluoromethylbenzoyl]}.

(21) The thiadiazoline derivative according to the aforementioned (20), wherein $R^{4A}$ is substituted or unsubstituted lower alkyl, substituted or unsubstituted lower alkynyl, or substituted or unsubstituted lower alkenyl, $R^{5A}$ is substituted or unsubstituted cycloalkyl, a substituted or unsubstituted heterocyclic group, or substituted or unsubstituted aryl, or $R^{4A}$ and $R^{5A}$ are combined to represent —$(CR^{28}R^{29})_{m1}$-Q-$(CR^{28A}R^{29A})_{m2}$— (wherein $R^{28}$, $R^{29}$, $R^{28A}$, $R^{29A}$, m1, m2 and Q have the same meanings as those of the aforementioned, respectively), or the pharmacologically acceptable salt thereof.

(22) The antitumor agent according to the aforementioned (20), wherein $R^{5A}$ is substituted or unsubstituted lower alkyl, substituted or unsubstituted lower alkynyl, substituted or unsubstituted lower alkenyl, or substituted or unsubstituted cycloalkyl.

(23) The thiadiazoline derivative according to the aforementioned (20) or (21), wherein $R^{5A}$ is substituted or unsubstituted aryl, or a substituted or unsubstituted heterocyclic group, or the pharmacologically acceptable salt thereof.

(24) The thiadiazoline derivative according to the aforementioned (20) or (21), wherein $R^{5A}$ is substituted or unsubstituted phenyl or substituted or unsubstituted thienyl, or the pharmacologically acceptable salt thereof.

(25) The thiadiazoline derivative according to any one of the aforementioned (20) to (24), wherein $R^{4A}$ is substituted or unsubstituted lower alkyl, or the pharmacologically acceptable salt thereof.

(26) The thiadiazoline derivative according to any one of the aforementioned (20) to (24), wherein $R^{4A}$ is substituted lower alkyl, or the pharmacologically acceptable salt thereof.

(27) The thiadiazoline derivative according to the aforementioned (20), wherein $R^{4A}$ and $R^{5A}$ combine together to represent —$(CR^{28}R^{29})_{m1}$-Q-$(CR^{28A}R^{29A})_{m2}$— (wherein $R^{28}$, $R^{29}$, $R^{28A}$, $R^{29A}$, m1, m2, and Q have the same meanings as those of the aforementioned, respectively), or the pharmacologically acceptable salt thereof.

(28) The thiadiazoline derivative according to the aforementioned (20), wherein $R^{4A}$ and $R^{5A}$ are combined to represent —$(CH_2)_{m1}$-Q-$(CH_2)_{m2}$— (wherein m1, m2 and Q have the same meanings as those of the aforementioned, respectively), or the pharmacologically acceptable salt thereof.

(29) The thiadiazoline derivative according to the aforementioned (27) or (28), wherein Q is substituted or unsubstituted phenylene, or the pharmacologically acceptable salt thereof.

(30) The thiadiazoline derivative according to any one of the aforementioned (20) to (29), wherein $R^{1A}$ is a hydrogen atom, or substituted or unsubstituted lower alkyl, or the pharmacologically acceptable salt thereof.

(31) The thiadiazoline derivative according to any one of the aforementioned (20) to (29), wherein $R^{1A}$ is a hydrogen atom, or the pharmacologically acceptable salt thereof.

(32) The thiadiazoline derivative according to any one of the aforementioned (20) to (31), wherein $R^{2A}$ is —$C(=W)R^6$ (wherein W and $R^6$ have the same meanings as those of the aforementioned, respectively), or the pharmacologically acceptable salt thereof.

(33) The thiadiazoline derivative according to the aforementioned (32), wherein $R^6$ is substituted or unsubstituted lower alkyl, substituted or unsubstituted lower alkynyl, substituted or unsubstituted lower alkenyl, or substituted or unsubstituted cycloalkyl, or the pharmacologically acceptable salt thereof.

(34) The thiadiazoline derivative according to the aforementioned (32) or (33), wherein W is an oxygen atom, or the pharmacologically acceptable salt thereof.

(35) The thiadiazoline derivative according to any one of the aforementioned (20) to (29), wherein $R^{1A}$ and $R^{2A}$ are combined together with the adjacent nitrogen atom to form a substituted or unsubstituted heterocyclic group, or the pharmacologically acceptable salt thereof.

(36) The thiadiazoline derivative according to any one of the aforementioned (20) to (35), wherein $R^{3A}$ is —$C(=W^A)R^{6A}$ (wherein $W^A$ and $R^{6A}$ have the same meanings as those of the aforementioned, respectively), or the pharmacologically acceptable salt thereof.

(37) The thiadiazoline derivative according to the aforementioned (36), wherein $R^{6A}$ is substituted or unsubstituted lower alkyl, substituted or unsubstituted lower alkynyl, substituted or unsubstituted lower alkenyl, or substituted or unsubstituted cycloalkyl, or the pharmacologically acceptable salt thereof.

(38) The thiadiazoline derivative according to the aforementioned (36), wherein $R^{6A}$ is lower alkyl, or the pharmacologically acceptable salt thereof.

(39) The thiadiazoline derivative according to any one of the aforementioned (36) to (38), wherein $W^A$ is an oxygen atom, or the pharmacologically acceptable salt thereof.

(40) A pharmaceutical composition which comprises the thiadiazoline derivative according to any one of the aforementioned (20) to (39) or a pharmacologically acceptable salt thereof as an active ingredient.

(41) An antitumor agent which comprises the thiadiazoline derivative according to any one of the aforementioned (20) to (39) or a pharmacologically acceptable salt thereof as an active ingredient.

(42) Use of the thiadiazoline derivative according to any one of the aforementioned (20) to (39) or a pharmacologically acceptable salt thereof for the manufacture of an antitumor agent.

(43) A method for the treatment of malignant tumor comprising administering an effective amount of the thiadiazoline derivative according to any one of the aforementioned (20) to (39) or a pharmacologically acceptable salt thereof.

Hereinafter, compounds represented by the general formulae (I) and (IA) are referred to as Compound (I) and Compound (IA), respectively. The compounds having the other formula numbers are referred to in the same manner.

In the definition of each group of Compound (I) and Compound (IA), (i) examples of the lower alkyl moiety in the lower alkyl, the lower alkoxy, the lower alkylamino and the di(lower alkyl)amino include straight or branched chain alkyl having 1 to 10 carbon atoms, for example, methyl, ethyl, propyl, isopropyl, butyl, isobutyl, sec-butyl, tert-butyl, pentyl, isopentyl, neopentyl, hexyl, heptyl, octyl, nonyl, decyl and the like.

The two lower alkyl moieties in the di(lower alkyl)amino may be the same or different.

(ii) Examples of the cycloalkyl include cycloalkyl having 3 to 8 carbon atoms, for example, cyclopropyl, cyclobutyl, cyclopentyl, cyclohexyl, cycloheptyl, cyclooctyl and the like.

Examples of the cycloalkylene include cycloalkylene having 3 to 8 carbon atoms, for example, cyclopropylene, cyclobutylene, cyclopentylene, cyclohexylene, cycloheptylene, cyclooctylene and the like.

(iii) Examples of the lower alkenyl include straight or branched chain alkenyl having 2 to 8 carbon atoms, for example, vinyl, allyl, butenyl, pentenyl, hexenyl, heptenyl, octenyl and the like.

(iv) Examples of the lower alkynyl include straight or branched chain alkynyl having 2 to 8 carbon atoms, for example, ethynyl, propynyl, butynyl, pentynyl, hexynyl, heptynyl, octynyl and the like.

(v) Examples of the aryl moiety in the aryl, the aryloxy and the arylamino include phenyl, naphthyl and the like.

(vi) Examples of the heterocyclic group include an aliphatic heterocyclic group, an aromatic heterocyclic group and the like. Examples of the aliphatic heterocyclic group include a 5- or 6-membered monocyclic aliphatic heterocyclic group containing at least one atom selected from a nitrogen atom, an oxygen atom and a sulfur atom, and a bicyclic or tricyclic condensed aliphatic heterocyclic group comprising 3- to 8-membered rings and containing at least one atom selected from a nitrogen atom, an oxygen atom and a sulfur atom, and the like, for example, pyrrolidinyl, imidazolidinyl, piperidinyl, piperazinyl, morpholinyl, thiomorpholinyl, piperidino, morpholino, oxazolinyl, dioxolanyl, tetrahydropyranyl and the like. Examples of the aromatic heterocyclic group include a 5- or 6-membered monocyclic aromatic heterocyclic group containing at least one atom selected from a nitrogen atom, an oxygen atom and a sulfur atom, and a bicyclic or tricyclic condensed aromatic heterocyclic group comprising 3- to 8-membered rings and containing at least one atom selected from a nitrogen atom, an oxygen atom and a sulfur atom, and the like, for example, furyl, thienyl, benzothienyl, pyrrolyl, pyridyl, pyrazinyl, imidazolyl, pyrazolyl, triazolyl, thiazolyl, isothiazolyl, thiadiazolyl, oxazolyl, oxadiazolyl, pyrimidinyl, indolyl, isoindolyl, benzothiazolyl, benzimidazolyl, benzotriazolyl, quinolyl, isoquinolyl, quinazolinyl, pyranyl and the like.

(vii) Examples of the heterocyclic group formed together with the adjacent nitrogen atom include an aliphatic heterocyclic group containing at least one nitrogen atom, and the like. Said aliphatic heterocyclic group containing at least one nitrogen atom may contain an oxygen atom, a sulfur atom or another nitrogen atom, and examples thereof include, for example, pyrrolidinyl, morpholino, thiomorpholino, pyrazolidinyl, piperidino, piperazinyl, homopiperazinyl, aziridinyl, azetidinyl, azolidinyl, perhydroazepinyl, perhydroazocinyl, succinimidyl, pyrrolidonyl, glutarimidyl, piperidonyl and the like.

(viii) The substituents in the substituted lower alkyl, the substituted lower alkoxy, the substituted lower alkenyl, the substituted lower alkynyl, the substituted cycloalkyl, the substituted lower alkylamino, and the substituted di(lower alkyl)amino may be the same or different and include for example, 1 to 3 substituent(s), such as halogen, oxo, hydroxy, nitro, azide, cycloalkyl, aryl, a heterocyclic group, substituted aryl (the substituent in said substituted aryl has the same meaning as that of the after-mentioned substituent (xii) in the substituted aryl), a substituted heterocyclic group (the substituent in said substituted heterocyclic group has the same meaning as that of the after-mentioned substituent (xiii) in the substituted heterocyclic group), —$CONR^{16}R^{16}$<wherein $R^{15}$ and $R^{16}$ are the same or different and each represents
a hydrogen atom, hydroxy, cycloalkyl, lower alkyl,
lower alkenyl, aryl, a heterocyclic group,
substituted aryl (the substituent in said substituted aryl has the same meaning as that of the after-mentioned substituent (xii) in the substituted aryl),
a substituted heterocyclic group (the substituent in said substituted heterocyclic group has the same meaning as that of the after-mentioned substituent (xiii) in the substituted heterocyclic group) or
substituted lower alkyl {in said substituted lower alkyl, the substituents are the same or different and 1 to 3 substituent(s), such as
hydroxy, lower alkoxy, oxo, carboxy, lower alkoxycarbonyl, an aryl, a heterocyclic group,
—$CONR^{15A}R^{16A}$ [wherein
$R^{15A}$ and $R^{16A}$ are the same or different and each represents
a hydrogen atom, hydroxy, lower alkyl, or
substituted lower alkyl (in said substituted lower alkyl, the substituents (a) are the same or different and 1 to 3 substituent(s), such as hydroxy, lower alkoxy, oxo, carboxy, lower alkoxycarbonyl, aryl, a heterocyclic group, amino, lower alkylamino, di(lower alkyl)amino and the like), or
$R^{15A}$ and $R^{16A}$ are combined to form a heterocyclic group
together with the adjacent nitrogen atom],
—$NR^{41}R^{42}$ [wherein
$R^{41}$ and $R^{42}$ are the same or different and each represents
a hydrogen atom, lower alkyl,
lower alkanoyl, aroyl, aryl,
a heterocyclic group, substituted lower alkyl (the substituent in said substituted lower alkyl has the same meaning as that of the aforementioned substituent (a) in the substituted lower alkyl), a substituted lower alkanoyl (in said substituted lower alkanoyl, the substituents (b) are the same or different and 1 to 3 substituent(s), such as hydroxy, lower alkoxy, oxo, carboxy, lower alkoxycarbonyl, amino, lower alkylamino, di(lower alkyl)amino and the like), substituted aroyl (the substituent in said substituted aroyl has the same meaning as that of the aforementioned substituent (b) in the substituted lower alkanoyl), substituted aryl (the substituent in said substituted aryl has the same meaning as that of the after-mentioned substituent (xii) in the substituted aryl) or a substituted heterocyclic group (the substituent in said substituted heterocyclic group has the same meaning as that of the after-mentioned substituent (xiii) in the substituted heterocyclic group), or $R^{41}$ and $R^{42}$ are combined to form a heterocyclic group or a substituted heterocyclic group together with the adjacent nitrogen atom (the substituent in said substituted heterocyclic group formed together with the adjacent nitrogen atom has the same meaning as that of the after-mentioned substituent (xiii) in the substituted heterocyclic group formed together with the adjacent nitrogen atom)]}, or $R^{15}$ and $R^{16}$ are combined to form a heterocyclic group or a substituted heterocyclic group together with the adjacent nitrogen atom (the substituent in said substituted heterocyclic group formed together with the adjacent nitrogen atom has the same meaning as that of the after-mentioned substituent (xiii) in the substituted heterocyclic group formed together with the adjacent nitrogen atom)>, —$CO_2R^{26}$ {wherein $R^{26}$ represents a hydrogen atom, lower alkyl, cycloalkyl, lower alkenyl, lower alkynyl, aryl, substituted aryl (the substituent in said substituted aryl has the same meaning as that of the after-mentioned substituent (xii) in the substituted aryl), or substituted lower alkyl [in said substituted lower alkyl, the substituents (c) are the same or different and 1 to 3 substituent(s), such as hydroxy, halogen, lower alkoxy, oxo, carboxy, lower alkoxycarbonyl, aryl, a heterocyclic group, —$CONR^{15B}R^{16B}$ (wherein $R^{15B}$ and $R^{16B}$ have the same meanings as those of the aforementioned $R^{15}$ and $R^{16}$, respectively), —$NR^{41A}R^{42A}$ (wherein $R^{41A}$ and $R^{42A}$ have the same meanings as those of the aforementioned $R^{41}$ and $R^{42}$, respectively), and the like]}, —$COR^{26A}$ (wherein $R^{26A}$ has the same meaning as that of the aforementioned $R^{26}$), —$NR^{17}R^{18}$<wherein $R^{17}$ and $R^{18}$ are the same or different and each represents a hydrogen atom, lower alkyl, lower alkenyl, aroyl, aryl, a heterocyclic group, cycloalkyl, aralkyloxycarbonyl, substituted lower alkyl {in said substituted lower alkyl, the substituents (d) are the same or different and 1 to 3 substituent(s), such as hydroxy, lower alkoxy, oxo, carboxy, lower alkoxycarbonyl, aryl, a heterocyclic group, substituted aryl (the substituent in said substituted aryl has the same meaning as that of the after-mentioned substituent (xii) in the substituted aryl), a substituted heterocyclic group (the substituent in said substituted heterocyclic group has the same meaning as that of the after-mentioned substituent (xiii) in the substituted heterocyclic group), —$O(CH_2CH_2O)_nR^{19}$ (wherein n represents an integer of from 1 to 15, and $R^{19}$ represents lower alkyl), —$CONR^{15C}R^{16C}$ (wherein $R^{15C}$ and $R^{16C}$ have the same meanings as those of the aforementioned $R^{15}$ and $R^{16}$, respectively), —$SO_2R^{24}$[wherein $R^{24}$ represents lower alkyl, aryl or substituted aryl (the substituent in said substituted aryl has the same meaning as that of the after-mentioned substituent (xii) in the substituted aryl)], —$NR^{41B}R^{42B}$ (wherein $R^{41B}$ and $R^{42B}$ have the same meanings as those of the aforementioned $R^{41}$ and $R^{42}$, respectively), and the like}, substituted aryl (the substituent in said substituted aryl has the same meaning as that of the after-mentioned substituent (xii) in the substituted aryl), a substituted heterocyclic group (the substituent in said substituted heterocyclic group has the same meaning as that of the after-mentioned substituent (xiii) in the substituted heterocyclic group), —$COR^{26B}$ {wherein $R^{26B}$ represents lower alkyl, lower alkenyl, lower alkynyl, aryl, substituted lower alkyl (the substituent in said substituted lower alkyl has the same meaning as that of the aforementioned substituent (c) in the substituted lower alkyl), substituted aryl (the substituent in said substituted aryl has the same meaning as that of the after-mentioned substituent (xii) in the substituted aryl), —$NR^{26C}R^{26D}$ (wherein $R^{26C}$ and $R^{26D}$ are the same or different, and each has the same meaning as that of the aforementioned $R^{26}$) or —$OR^{27}$[wherein $R^{27}$ represents lower alkyl, aryl, substituted lower alkyl (the substituent in said substituted lower alkyl has the same meaning as that of the aforementioned substituent (c) in the substituted lower alkyl) or substituted aryl (the substituent in said substituted aryl has the same meaning as that of the after-mentioned substituent (xii) in the substituted aryl)]}, or —$SO_2R^{26E}$ (wherein $R^{26E}$ has the same meaning as that of the aforementioned $R^{26}$), or $R^{17}$ and $R^{18}$ are combined to form a heterocyclic group or a substituted heterocyclic group together with the adjacent nitrogen atom (the substituent in said substituted heterocyclic group formed together with the adjacent nitrogen atom has the same meaning as that of the after-mentioned substituent (xiii) in the substituted heterocyclic group formed together with the adjacent nitrogen atom)>, —N+$R^{20}R^{21}R^{22}$X— (wherein
$R^{20}$ and $R^{21}$ are the same or different and each represents lower alkyl, or $R^{20}$ and $R^{21}$ are combined to form a heterocyclic group together with the adjacent nitrogen atom,
$R^{22}$ represents lower alkyl, and
X represents each atom of chlorine, bromine or iodine), —$OR^{23}$ {wherein
$R^{23}$ represents
lower alkyl, cycloalkyl, aryl, a heterocyclic group,
substituted aryl (the substituent in said substituted aryl has the same meaning as that of the after-mentioned substituent (xii) in the substituted aryl),
a substituted heterocyclic group (the substituent in said substituted heterocyclic group has the same meaning as that of the after-mentioned substituent (xiii) in the substituted heterocyclic group),
substituted lower alkyl [in said substituted lower alkyl, the substituents (e) are the same or different and 1 to 3 substituent(s), such as
hydroxy, halogen, lower alkoxy, oxo, carboxy,
lower alkoxycarbonyl, aryl, a heterocyclic group,
substituted aryl (the substituent in said substituted aryl has the same meaning as that of the after-mentioned substituent (xii) in the substituted aryl),
a substituted heterocyclic group (the substituent in said substituted heterocyclic group has the same meaning as that of the after-mentioned substituent (xiii) in the substituted heterocyclic group),
—O(CH$_2$CH$_2$O)$_{nA}$$R^{19A}$ (wherein nA and $R^{19A}$ have the same meanings as those of the aforementioned n and $R^{19}$, respectively),
—CONR$^{15D}R^{16D}$ (wherein $R^{15D}$ and $R^{16D}$ have the same meanings as those of $R^{15}$ and $R^{16}$, respectively),
—NR$^{41C}R^{42C}$ (wherein $R^{41C}$ and $R^{42C}$ have the same meanings as those of the aforementioned $R^{41}$ and $R^{42}$, respectively) and the like],
—COR$^{26F}$ (wherein $R^{26F}$ has the same meaning as that of the aforementioned $R^{26}$) or
—CONR$^{15E}R^{16E}$ (wherein $R^{15E}$ and $R^{16E}$ have the same meanings as those of the aforementioned $R^{15}$ and $R^{16}$, respectively)}, —SR$^{23A}$ (wherein $R^{23A}$ has the same meaning as that of the aforementioned $R^{23}$), —SO$_2$R$^{25}$ [wherein
$R^{25}$ represents
lower alkyl, cycloalkyl, aryl,
substituted lower alkyl (the substituent in said substituted lower alkyl has the same meaning as that of the aforementioned substituent (c) in the substituted lower alkyl),
a substituted aryl (the substituent in the substituted aryl has the same meaning as that of the after-mentioned substituent (xii) in the substituted aryl), or
—NR$^{15F}R^{16F}$ (wherein $R^{15F}$ and $R^{16F}$ have the same meanings as those of the aforementioned $R^{15}$ and $R^{16}$, respectively)], —OSO$_2$R$^{25A}$ (wherein $R^{26A}$ has the same meaning as that of the aforementioned $R^{25}$), and the like.

Herein, the lower alkyl moiety in the lower alkyl, the lower alkoxy, the lower alkoxycarbonyl, the lower alkylamino and the di(lower alkyl)amino, the aryl moiety in the aryl and the aroyl, the cycloalkyl, the lower alkenyl, the lower alkynyl, the heterocyclic group, and the heterocyclic group formed together with the adjacent nitrogen atom have the same meanings as those of the aforementioned lower alkyl (i), aryl (v), cycloalkyl (ii), lower alkenyl (iii), lower alkynyl (iv), hetero-cyclic group (vi) and a heterocyclic group formed together with the adjacent nitrogen atom (vii), respectively. Also, the lower alkyl moiety in the lower alkanoyl mentioned here has the same meaning as that of the aforementioned lower alkyl (i), the halogen (ix) represents each atom of fluorine, chlorine, bromine and iodine, and examples of the aralkyl moiety (xi) in the aralkyloxycarbonyl include aralkyl having 7 to 15 carbon atoms, for example, benzyl, phenethyl, benzhydryl, naphthylmethyl and the like.

(xii) The substituents in the substituted aryl, the substituted aryloxy, the substituted arylamino and the substituted phenylene may be the same or different and 1 to 3 substituent(s), such as
halogen, lower alkyl, nitro, oxo, hydroxy, lower alkoxy, amino, lower alkylamino, di(lower alkyl)amino, lower alkylaminocarbonyloxy, di(lower alkyl)aminocarbonyloxy, lower alkanoyl, lower alkanoylamino, lower alkanoyloxy, aryl, arylsulfonyl, heterocyclic amino, aroyl, carboxy, lower alkoxycarbonyl, cyano, methylenedioxy,
substituted lower alkyl (in said substituted lower alkyl, the substituents (f) are the same or different and 1 to 3 substituent(s), such as halogen, oxo, carboxy, lower alkoxycarbonyl, amino, lower alkylamino, di(lower alkyl)amino, hydroxy, lower alkoxy and the like),
substituted arylsulfonyl (the substituent in said substituted arylsulfonyl has the same meaning as that of the aforementioned substituent (f)),
substituted heterocyclic amino (the substituent in said substituted heterocyclic amino has the same meaning as that of the aforementioned substituent (f)) and the like.

the lower alkyl moiety in the lower alkyl, the lower alkylamino, the di(lower alkyl)amino, the lower alkylaminocarbonyloxy, the di(lower alkyl)aminocarbonyloxy (the two lower alkyl moieties in said di(lower alkyl)aminocarbonyloxy may be the same or different), the lower alkoxycarbonyl and the lower alkoxy, the heterocyclic moiety in the heterocyclic amino, the aryl moiety in the aryl, the arylsulfonyl and the aroyl, and the halogen have the same meanings as those of the aforementioned lower alkyl (i), heterocyclic group (vi), aryl (v) and halogen (ix), respectively. Also, examples of the lower alkanoyl moiety (x) in the lower alkanoyl, the lower alkanoylamino and the lower alkanoyloxy which are noted here include a straight or branched chain alkanoyl having 2 to 9 carbon atoms, for example, acetyl, propionyl, butyryl, isobutyryl, valeryl, isovaleryl, pivaloyl, hexanoyl, heptanoyl, octanoyl, nonanoyl and the like.

(xiii) Examples of the substituent in the substituted heterocyclic group and the substituted heterocyclic group formed together with the adjacent nitrogen atom include oxo and the like as well as the aforementioned groups mentioned in the definition of the substituent (xii) in the substituted aryl.

Example of the pharmacologically acceptable salt of Compound (I) and Compound (IA) include pharmacologically acceptable acid addition salts, metal salts, ammonium salts, organic amine addition salts, amino acid addition salts and the like. Examples of the acid addition salt include an inorganic salt such as a hydrochloride, a sulfate and a phosphate, an organic acid salt such as an acetate, a maleate, a fumarate, a tartrate, a citrate, a lactate, an aspartate, a glutamate, succinate and the like. Examples of the metal salt include an alkali metal salt such as a sodium salt and a potassium salt, an alkaline-earth metal salt such as a magnesium salt and a calcium salt, an aluminium salt, a zinc salt and the like. Examples of the ammonium salt include a salt of ammonium, tetramethylammonium and the like. Examples of the organic amine addition salt include an addition salt with morpholine, piperidine or the like. Examples of the amino acid addition salt include an addition salt with lysine, glycine, phenylalanine and the like.

Next, the methods of preparing the Compound (I) and the Compound (IA) are described as follows.

In the preparing methods as shown below, when the defined group changes under the conditions of the method carried out, or the method is inappropriate for carrying out, the desired compound can be obtained by using the protection and deprotection of the groups which are ordinarily used in the synthetic organic chemistry [e.g., Protective Groups in Organic Synthesis, T. W. Greene, John Wiley & Sons Inc. (1981)] and the like. In addition, the order of the steps for introducing a substituent and the like may be changed, if necessary.

Compound (I) can be prepared according to the following reaction steps.

Compound (IA) can also be prepared in the similar manner as in the preparing methods of Compound (I) as shown below.

Preparing Method 1

Among Compound (I), Compound (Ia) wherein $R^2$ is a hydrogen atom, substituted or unsubstituted lower alkyl, substituted or unsubstituted lower alkynyl, substituted or unsubstituted lower alkenyl, or substituted or unsubstituted cycloalkyl, or $R^1$ and $R^2$ are combined to form a substituted or unsubstituted heterocyclic group together with the adjacent nitrogen atom, and $R^3$ is —C(=O)$R^{6A}$ can be obtained from Compound (II) and Compound (III), via Compound (IV), in accordance with known methods [e.g., J. Heterocyclic Chem., Vol. 21, p. 599 (1984) and the like]:

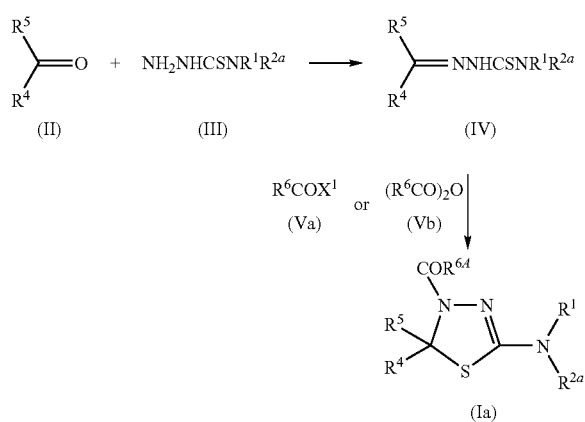

(wherein $R^1$, $R^4$, $R^5$, $R^6$ and $R^{6A}$ have the same meanings as those mentioned above, respectively, $X^1$ has the same meaning as that of the aforementioned X, and $R^{2a}$ represents a hydrogen atom, substituted or unsubstituted lower alkyl, substituted or unsubstituted lower alkynyl, substituted or unsubstituted lower alkenyl, or substituted or unsubstituted cycloalkyl among the definition of the aforementioned $R^2$, or $R^1$ and $R^{2a}$ are combined to form a substituted or unsubstituted heterocyclic group together with the adjacent nitrogen atom.)

Preparing Method 2

Among Compound (I), Compound (Ib) wherein $R^2$ and $R^3$ are the same to be —C(=O)$R^{6B}$ (wherein $R^{6B}$ has the same meaning as that of the aforementioned $R^6$) can be obtained from Compound (IVa) among Compound (IV) prepared by the preparing method 1 wherein $R^{2a}$ is a hydrogen atom, and Compound (Va) or Compound (Vb) in accordance with known methods [e.g., J. Bangladesh Chem. Soc., Vol. 5, p. 127 (1992), J. Org. Chem., Vol. 45, p. 1473 (1980), Patent of East Germany No. 243930, and the like]:

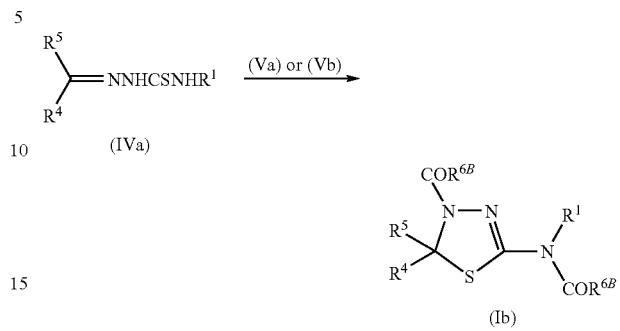

(wherein $R^1$, $R^4$, $R^5$ and $R^{6B}$ have the same meanings as those mentioned above, respectively.)

Preparing Method 3

Among Compound (Ia), Compound (Ic) wherein $R^2$ is a hydrogen atom and $R^3$ is —C(=O)$R^{6A}$ can be obtained by the following step from Compound (Ib) prepared by the Preparing method 2:

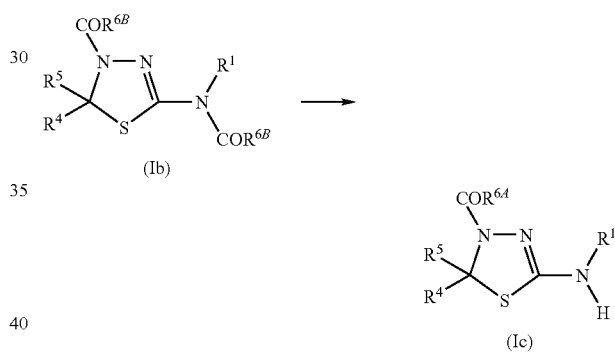

(wherein $R^1$, $R^4$, $R^5$, $R^{6A}$ and $R^{6B}$ have the same meanings as those mentioned above, respectively.)

Compound (Ic) can be obtained by treatment of Compound (Ib) in an inert solvent, for example, N,N-dimethylformamide and the like, in the presence of an appropriate base such as sodium hydride and the like, at a temperature between 0° C. and 80° C. for 10 minutes to 10 hours. The base is preferably used in an amount of 1 to 5 equivalents to Compound (Ib).

Alternatively, Compound (Ic) can also be obtained by the following method.

Compound (Ic) can be obtained by treatment of Compound (Ib) in an inert solvent, for example, aqueous or anhydrous ethanol, acetonitrile, chloroform and the like, in the presence of an appropriate base such as hydrazine monohydrate, aqueous sodium hydroxide and the like, at a temperature between 0° C. and 50° C. for 1 to 10 hours. The base is preferably used in an amount of 2 to 10 equivalents to Compound (Ib).

Compound (Ic) can also be obtained by the following method.

Compound (Ic) can be obtained by treatment of Compound (Ib) in a solvent such as methanol, tert-butanol and the like, in the presence of a reducing agent such as sodium borohydride and the like, and if necessary, in the presence of cerium chloride heptahydrate and the like, at a temperature between −10° C. and 100° C. for 0.1 to 15 hours. The reducing agent is preferably used in an amount of 1 to 200 equivalents to Compound (Ib).

Preparing Method 4

Among Compound (I), Compound (Ie) wherein $R^2$ is —C(=O)$R^6$ and $R^3$ is —C(=O)$R^{6A}$ can be obtained by the following step from Compound (Ic) obtained by the Preparing method 1 or 3.

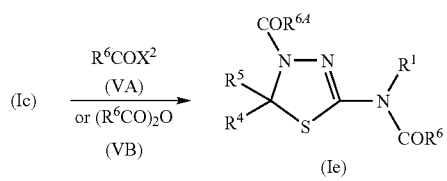

(wherein $R^1$, $R^4$, $R^5$, $R^6$ and $R^{6A}$ have the same meanings as those mentioned above, respectively, and $X^2$ has the same meaning as that of the aforementioned X.)

Compound (Ie) can be obtained by allowing Compound (Ic) to react with Compound (VA) or Compound (VB) in an inert solvent, for example, acetone, ethyl acetate, acetonitrile, N,N-dimethylformamide, dichloromethane and the like, in the presence of an appropriate base such as pyridine, 4-(dimethylamino)pyridine (DMAP), sodium hydride and the like, at a temperature between 0° C. and 120° C. for 2 to 12 hours. The base and Compound (VA) or Compound (VB) are preferably used, respectively, in an amount of 1 to 3 equivalents to Compound (Ic).

Preparing Method 5

Among Compound (I), Compound (If) wherein $R^2$ is —SO$_2$$R^{14}$ and $R^3$ is —C(=O)$R^{6A}$ can be obtained from Compound (Ic) prepared by the Preparing method 1 or 3 in accordance with the method described in for example, Shin-Jikken-Kagaku-Koza (New Experiment Chemistry Lecture) Vol. 14, p. 1803 (Maruzen, 1978):

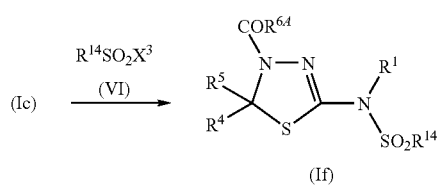

(wherein $R^1$, $R^4$, $R^5$, $R^{6A}$ and $R^{14}$ have the same meanings as those mentioned above, respectively, and $X^3$ has the same meaning as that of the aforementioned X.)

Preparing Method 6

Among Compound (I), Compound (Ig) wherein $R^2$ is —NR$^{11}$R$^{12}$ and $R^3$ is —C(=O)$R^{6A}$ can be obtained from Compound (VII) prepared in accordance with the method described in Indian J. Chem., Section B, Vol. 31(B), p. 547 (1992) in accordance with the methods described in for example, Indian J. Chem., Section B, Vol. 31B(8), p. 547 (1992); Phosphorus Sulfur & Silicon & the Related Elements, Vol. 122, p. 307 (1997) and the like:

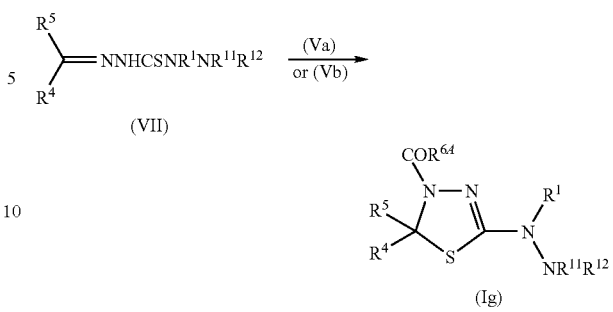

(wherein $R^1$, $R^4$, $R^5$, $R^{6A}$, $R^{11}$ and $R^{12}$ have the same meanings as those mentioned above, respectively.)

Preparing Method 7

Among Compound (Ie), Compound (Ie-b) wherein $R^1$ is substituted or unsubstituted lower alkyl, substituted or unsubstituted lower alkynyl, substituted or unsubstituted lower alkenyl, or substituted or unsubstituted cycloalkyl can be obtained by the following step from Compound (Ie-a) among Compound (Ie) wherein $R^1$ is a hydrogen atom prepared by the Preparing method 4:

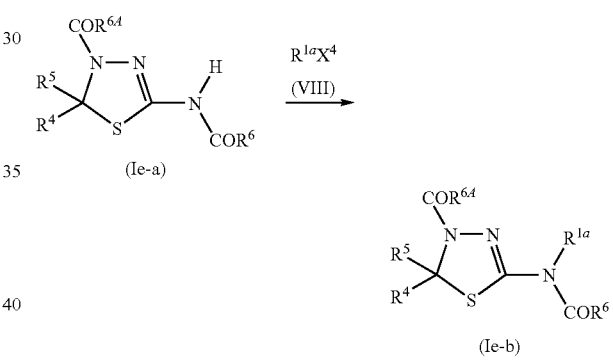

(wherein $R^4$, $R^5$, $R^6$ and $R^{6A}$ have the same meanings as those mentioned above, respectively, $X^4$ has the same meaning as that of the aforementioned X, and $R^{1a}$ represents substituted or unsubstituted lower alkyl, a substituted or unsubstituted lower alkynyl, substituted or unsubstituted lower alkenyl, or substituted or unsubstituted cycloalkyl among the definition of the aforementioned $R^1$.)

Compound (Ie-b) can be obtained by allowing Compound (Ie-a) to react with Compound (VIII) in an inert solvent, for example, N,N-dimethylformamide and the like, in the presence of an appropriate base such as sodium hydroxide, at a temperature between 0° C. and room temperature for 1 to 24 hours. The base and Compound (VIII) are preferably used in amounts of 2 to 5 equivalents and 2 to 3 equivalents, respectively, to Compound (Ie-a).

Preparing Method 8

Among Compound (I), Compound (Ih) wherein $R^3$ is a hydrogen atom can be obtained by the methods described in for example, Phosphorus, Sulfur and Silicone and the Related Elements, Vol. 122, p. 307 (1997) and Chem. Ber., Vol. 123, p. 691 (1990) and the like, or the methods similar to the aforementioned methods.

Preparing Method 9

Among Compound (I), Compound (Ij) wherein $R^2$ and/or $R^3$ is —C(=S)$R^6$ and/or —C(=S)$R^{6A}$, respectively, can be obtained by thiocarbonylation of Compound (Ik) wherein the corresponding $R^2$ and/or $R^3$ is —C(=O)$R^6$ and/or —C(=O) $R^{6A}$, respectively, among Compound (Ia) to Compound (Ih) obtained by the aforementioned the Preparing methods 1 to 7.

For example, Compound (Ij) can be obtained by treatment of Compound (Ik) in a solvent such as toluene and tetrahydrofuran, with an appropriate thiocarbonylating agent such as 2,4-bis(4-methoxyphenyl)-1,3-dithia-2,4-diphophethane-2,4-disulfide (Lawesson's reagent), phosphorus pentasulfide and the like, at a temperature between room temperature and the boiling point of the solvent for 1 to 24 hours. The thiocarbonylating agent is preferably used in an amount of 2 to 10 equivalents to Compound (Ik).

Preparing Method 10

Among Compound (I), Compound (Im) wherein $R^3$ is —C(=O)$R^{6A}$ and $R^1$ and $R^{2f}$ are combined to form a substituted or unsubstituted heterocyclic group together with the adjacent nitrogen atom can be obtained by the following step from Compound (In) wherein $R^1$ and $R^{2a}$ are hydrogen atoms among Compound (Ia) prepared by the Preparing method 1, or from Compound (In) wherein $R^1$ is a hydrogen atom among Compound (Ic) prepared by the Preparing method 3:

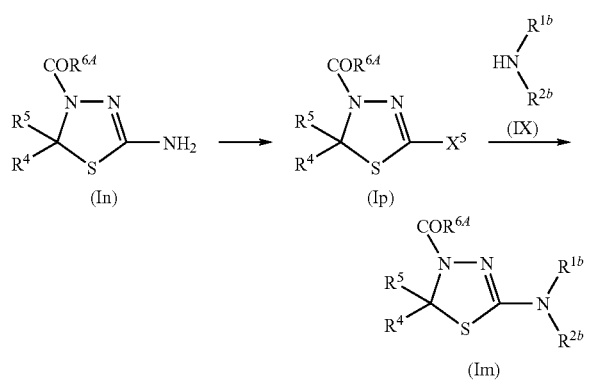

(wherein $R^4$, $R^5$ and $R^{6A}$ have the same meanings as those mentioned above, respectively, $X^5$ has the same meaning as that of the aforementioned X, $R^{1b}$ and $R^{2b}$ represent a substituted or unsubstituted heterocyclic group formed together with the adjacent nitrogen atom, said heterocyclic group formed together with the adjacent nitrogen atom has the same meaning as that of the aforementioned heterocyclic group (vii) formed together with the adjacent nitrogen atom, and the substituent in said substituted heterocyclic group formed together with the adjacent nitrogen atom has the same meaning as that of the aforementioned substituent (xiii) in the heterocyclic group.)

Compound (Ip) can be obtained from Compound (In) by the methods described in for example, Chem. Commun., Vol. 8, p. 873 (1998) and the like, or the methods similar to the aforementioned methods.

Compound (Im) can be obtained by allowing Compound (Ip) to react with Compound (IX) in an inert solvent, for example, dichloromethane and the like, at a temperature between 0° C. and 60° C. for 10 minutes to 24 hours. Compound (IX) is preferably used in an amount of 2 to 50 equivalents to Compound (Ip).

Alternatively, Compound (Im) can also be obtained from Compound (Ie-c) wherein $R^1$ is a hydrogen atom and $R^6$ is an alkyl group substituted with carboxyl group among Compound (Ie) prepared by the Preparing method 4 by the method described in for example, Synthesis-Stuttgart, Vol. 5, p. 420 (1991) or the methods similar to the aforementioned method.

Moreover, Compound (Im) can also be obtained from Compound (Ie-d) wherein $R^1$ is a hydrogen atom and $R^6$ is an alkyl group substituted with halogen among Compound (Ie) by the method described in for example, Shin-Jikken-Kagaku-Koza (New Experiment Chemistry Lecture) Vol. 14, p. 1174 (Maruzen, 1978) and the like, or the methods similar to the aforementioned methods.

Furthermore, among Compound (I), Compound (Ij-a) wherein $R^3$ is —C(=S)$R^{6A}$ and $R^1$ and $R^2$ are combined to form a substituted or unsubstituted heterocyclic group together with the adjacent nitrogen atom can be obtained from Compound (Im) in the similar manner as the aforementioned the Preparing method 9.

In Compound (I), conversion of the functional group contained in $R^1$, $R^2$, $R^3$, $R^4$ or $R^5$ can also be carried out by the aforementioned steps, or also by the other known methods [e.g., Comprehensive Organic Transformations, R. C. Larock (1989) and the like].

Compound (I) having the desired functional group at the desired position can be obtained by carrying out the aforementioned methods in appropriate combination.

The intermediates and the objective compounds in the aforementioned preparation methods can be purified and isolated by conducting a purification method ordinarily used in the synthetic organic chemistry such as filtration, extraction, washing, drying, concentration, recrystallization, various chromatography such as high performance liquid chromatography, thin layer chromatography, silica gel chromatography and the like. The intermediates can also be subjected to the next reaction without particular purification.

Some compounds among Compounds (I) may exist as position isomers, geometrical isomers, optical isomers, tautomers and the like. All possible isomers including the aforementioned isomers and mixtures thereof can be used for the antitumor agent of the present invention.

To obtain a salt of Compound (I), when Compound (I) obtained as a salt form, it may be purified as it is. When Compound (I) obtained as a free form, it may be dissolved or suspended in an appropriate solvent, and added with an appropriate acid or base to form a salt and then be isolated.

In addition, Compound (I) or a pharmacologically acceptable salt thereof may exist in the form of adducts with water or variety of solvents, which also can be used for the antitumor agent of the present invention.

Specific examples of Compound (IA) obtained by the present invention are shown in Tables 1 to 10. However, the compounds of the present invention are not limited to these examples.

The compounds shown in Tables 1 to 10 are used for the antitumor agent of the present invention, and other than the compounds, specific examples of compounds used in the present invention are shown in Tables 11 to 13. However, the compound used in the present invention is not limited to these examples.

TABLE 1

(IA-i)

| Example No. | Compound No. | R¹ᴬ | R²ᴬ | R⁴ᴬ |
|---|---|---|---|---|
| 2 | 2 | —H | —COCH$_3$ | —CH$_2$CH$_3$ |
| 4 | 4 | —H | —COCH$_3$ | —CH(CH$_3$)$_2$ |
| 5 | 5 | —H | —COCH$_3$ | cyclopropyl |
| 7 | 7 | —CH$_3$ | —COCH$_3$ | —CH$_3$ |
| 8 | 8 | —CH$_2$CH$_3$ | —CH$_2$CH$_3$ | —CH$_3$ |
| 8 | 9 | —CH$_2$CH$_3$ | —COCH$_3$ | —CH$_3$ |
| 9 | 10 | —(CH$_2$)$_2$CH$_3$ | —(CH$_2$)$_2$CH$_3$ | —CH$_3$ |
| 9 | 11 | —(CH$_2$)$_2$CH$_3$ | —COCH$_3$ | —CH$_3$ |
| 129 | 136 | —H | —CO$_2$C(CH$_3$)$_3$ | —CH$_3$ |
| 130 | 137 | —H | —CON(CH$_3$)$_2$ | —CH$_3$ |
| 131 | 138 | (R¹ᴬ–R²ᴬ bridge: —(CH$_2$)$_6$—) | | —CH$_3$ |
| 132 | 139 | (R¹ᴬ–R²ᴬ bridge: —CH$_2$CH(CH$_3$)(CH$_2$)$_3$—) | | —CH$_3$ |
| 133 | 140 | —H | —CO(CH$_2$)$_4$CH$_3$ | —CH$_2$NHSO$_2$CH$_3$ |
| 134 | 141 | —H | —COCH=CHCH$_3$ | —CH$_2$NHSO$_2$CH$_3$ |
| 135 | 142 | —H | —CO-cyclopropyl | —CH$_2$NHSO$_2$CH$_3$ |
| 136 | 143 | —H | —COC(CH$_3$)$_2$OCOCH$_3$ | —CH$_2$NHSO$_2$CH$_3$ |
| 137 | 144 | —H | —COC(CH$_3$)$_2$OH | —CH$_2$NHSO$_2$CH$_3$ |
| 138 | 145 | —H | —COCH$_2$OCH$_3$ | —CH$_2$NHSO$_2$CH$_3$ |
| 139 | 146 | —H | —COCH$_2$Cl | —CH$_2$NHSO$_2$CH$_3$ |
| 140 | 147 | —H | —COCH$_2$N(CH$_3$)$_2$ | —CH$_2$NHSO$_2$CH$_3$ |
| 141 | 148 | —H | —CO(CH$_2$)$_3$CO$_2$CH$_3$ | —CH$_2$NHSO$_2$CH$_3$ |
| 142 | 149 | —H | —CO(CH$_2$)$_3$CO$_2$H | —CH$_2$NHSO$_2$CH$_3$ |
| 143 | 150 | (R¹ᴬ–R²ᴬ bridge: —CO(CH$_2$)$_3$CO—) | | —CH$_2$NHSO$_2$CH$_3$ |
| 144 | 151 | —H | —CO(CH$_2$)$_3$Br | —CH$_2$NHSO$_2$CH$_3$ |
| 145 | 152 | (R¹ᴬ–R²ᴬ bridge: —CO(CH$_2$)$_3$—) | | —CH$_2$NHSO$_2$CH$_3$ |
| 146 | 153 | —H | —CO(CH$_2$)$_4$Br | —CH$_2$NHSO$_2$CH$_3$ |
| 147 | 154 | (R¹ᴬ–R²ᴬ bridge: —CO(CH$_2$)$_4$—) | | —CH$_2$NHSO$_2$CH$_3$ |
| 148 | 155 | —H | —CO(CH$_2$)$_5$Br | —CH$_2$NHSO$_2$CH$_3$ |
| 149 | 156 | (R¹ᴬ–R²ᴬ bridge: —CO(CH$_2$)$_5$—) | | —CH$_2$NHSO$_2$CH$_3$ |

TABLE 2

(IA-ii)

[Structure: 5-phenyl-5-methyl-2,5-dihydro-1,3,4-thiadiazole with N-R³ᴬ, and 2-position has N(R¹ᴬ)(R²ᴬ)]

| Example No. | Compound No. | $R^{1A}$ | $R^{2A}$ | $R^{3A}$ |
|---|---|---|---|---|
| 10 | 12 | —CH₂Ph | —CH₂Ph | —COCH₃ |
| 10 | 13 | —CH₂Ph | —COCH₃ | —COCH₃ |
| 12 | 15 | —CH₃ | —H | —COCH₃ |
| 13 | 16 | —CH₃ | —CH₃ | —COCH₃ |
| 14 | 17 | —CH₃ | —H | —COCH₂CH₃ |
| 15 | 18 | —CH₃ | —COCH₃ | —COCH₂CH₃ |
| 16 | 19 | —CH₃ | —COCH₂CH₃ | —COCH₂CH₃ |
| 17 | 20 | —CH₃ | —CO(CH₂)₂CH₃ | —CO(CH₂)₂CH₃ |
| 18 | 21 | —CH₃ | —COCH(CH₃)₂ | —COCH(CH₃)₂ |
| 76 | 79 | —CH₂CH=CH₂ | —COCH₃ | —COCH₃ |
| 77 | 80 | —CH₂CH=CH₂ | —H | —COCH(CH₃)₂ |
| 77 | 81 | —CH₂CH=CH₂ | —COCH₃ | —COCH(CH₃)₂ |
| 78 | 82 | —H | —COC(CH₃)₃ | —COC(CH₃)₃ |
| 79 | 83 | —CH₃ | —H | —COCH(CH₃)₂ |
| 79 | 84 | —CH₃ | —COCH₃ | —COCH(CH₃)₂ |
| 80 | 85 | —H | —COCH(CH₃)₂ | —COCH(CH₃)₂ |
| 81 | 86 | —H | —H | —COCH(CH₃)₂ |
| 81 | 87 | —H | —COCH₃ | —COCH(CH₃)₂ |
| 82 | 88 | —H | —COCH(CH₃)₂ | —COCH₃ |
| 83 | 89 | —H | —C(O)-cyclopentyl | —COCH₃ |
| 84 | 90 | —H | —H | —COCH₂CH(CH₃)₂ |
| 84 | 91 | —H | —COCH(CH₃)₂ | —COCH₂CH(CH₃)₂ |
| 85 | 92 | —H | —COCH₃ | —COC(CH₃)₃ |
| 86 | 93 | —H | —COC(CH₃)₃ | —COCH₃ |

*Ph: phenyl

TABLE 3

(IA-iii)

[Structure: 1,3,4-thiadiazoline with N-COCH₃, R⁴ᴬ and R⁵ᴬ at 5-position, and N(R¹ᴬ)(COCH₃) at 2-position]

| Example No. | Compound No. | $R^{1A}$ | $R^{4A}$ | $R^{5A}$ |
|---|---|---|---|---|
| 22 | 25 | —H | —CH₃ | —CH=CHPh |
| 23 | 26 | —H | —(CH₂)₃CH₃ | —(CH₂)₃CH₃ |
| 24 | 27 | —H | \multicolumn{2}{c}{—(CH₂)₃-(2-phenylene)—} | |
| 25 | 28 | —H | \multicolumn{2}{c}{—(CH₂)₂-(2-phenylene)-CH₂—} | |

TABLE 3-continued
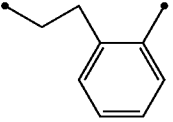
(IA-iii)
| Example No. | Compound No. | R$^{1A}$ | R$^{4A}$ | R$^{5A}$ |
|---|---|---|---|---|
| 26 | 29 | —H | | 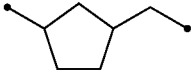 |
| 28 | 31 | —H | | 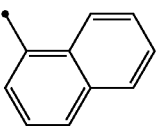 |
| 29 | 32 | —H | —CH$_3$ | 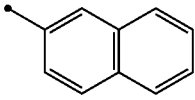 |
| 30 | 33 | —H | —CH$_3$ | 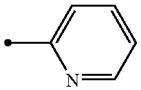 |
| 31 | 34 | —H | —CH$_3$ | 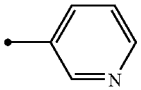 |
| 32 | 35 | —H | —CH$_3$ | 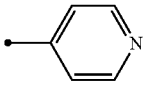 |
| 33 | 36 | —H | —CH$_3$ | 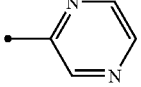 |
| 34 | 37 | —H | —CH$_3$ | 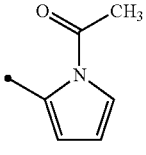 |
| 35 | 38 | —H | —CH$_3$ | 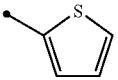 |
| 38 | 41 | —CH$_2$CH$_3$ | —CH$_3$ | 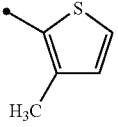 |
| 39 | 42 | —H | —CH$_3$ |  |

TABLE 3-continued (IA-iii)

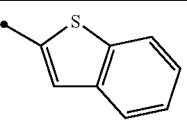

| Example No. | Compound No. | R¹ᴬ | R⁴ᴬ | R⁵ᴬ |
|---|---|---|---|---|
| 40 | 43 | —H | —CH₃ | 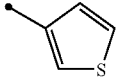 (benzothiophen-2-yl) |
| 41 | 44 | —H | —CH₃ | (thiophen-3-yl) |
| 42 | 45 | —H | —CH₃ | (thiazol-2-yl) |
| 125 | 132 | —H | —CH₃ | (5-bromothiophen-2-yl) |
| 126 | 133 | —H | —CH₃ | (3-bromothiophen-2-yl) |
| 127 | 134 | —H | —CH₃ | (3-chlorothiophen-2-yl) |

*Ph: phenyl

TABLE 4

(IA-iv)

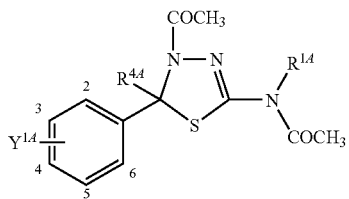

TABLE 4-continued (IA-iv)

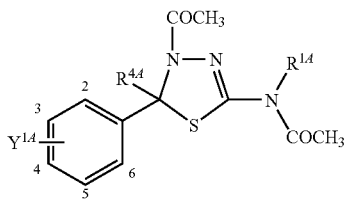

| Example No. | Compound No. | R¹ᴬ | R⁴ᴬ | Y¹ᴬ (Substituting position) |
|---|---|---|---|---|
| 43 | 46 | —H | —CH₃ | —CH₃ (2) |
| 44 | 47 | —H | —CH₃ | —CH₃ (3) |
| 45 | 48 | —H | —CH₃ | —CH₃ (4) |
| 46 | 49 | —H | —CH₂CH₃ | —CH₂CH₃ (2) |
| 47 | 50 | —H | —CH₃ | —OCH₃ (2) |
| 48 | 51 | —H | —CH₃ | —OCH₃ (3) |
| 50 | 53 | —H | —CH₃ | —F (2) |
| 51 | 54 | —H | —CH₃ | —F (3) |
| 52 | 55 | —H | —CH₃ | —F (4) |
| 53 | 56 | —H | —CH₃ | —Cl (2) |
| 54 | 57 | —CH₂CH₃ | —CH₃ | —Cl (2) |
| 55 | 58 | —H | —CH₃ | —Cl (3) |
| 56 | 59 | —H | —CH₃ | —Cl (4) |
| 57 | 60 | —H | —CH₃ | —Br (2) |
| 58 | 61 | —H | —CH₃ | —OCOCH₃ (2) |
| 60 | 63 | —H | —H | —OCOOH₃ (3) |
| 61 | 64 | —H | —CH₃ | —OCOCH₃ (4) |
| 62 | 65 | —H | —CH₃ | —NO₂ (2) |
| 65 | 68 | —H | —CH₃ | —OH (2) |
| 66 | 69 | —H | —CH₃ | —OH (3) |

TABLE 4-continued (IA-iv)

| Example No. | Compound No. | $R^{1A}$ | $R^{4A}$ | $Y^{1A}$ (Substituting position) |
|---|---|---|---|---|
| 67 | 70 | —H | —CH₃ | —OH (4) |
| 68 | 71 | —H | —CH₃ | —CN (3) |
| 69 | 72 | —H | —CH₃ | —CN (4) |
| 70 | 73 | —H | —CH₃ | —CF₃ (3) |
| 71 | 74 | —H | —CH₃ | —COOH (2) |
| 118 | 125 | —CH₂CH₃ | —CH₃ | —OCOCH₃ (3) |
| 119 | 126 | —CH₂CH₃ | —CH₃ | —OH (3) |
| 120 | 121 | —H | —CH₃ | —OCONHCH₂CH₃ (3) |

TABLE 5

(IA-v)

| Example No. | Compound No. | $Y^{1A}$ (Substituting position) | $Y^{2A}$ (Substituting position) |
|---|---|---|---|
| 72 | 75 | —OCH₃ (2) | —OCH₃ (6) |
| 73 | 76 | —OH (3) | —OH (5) |
| 74 | 77 | —OH (3) | —OH (4) |
| 75 | 78 | —CH₃ (2) | —CH₃ (4) |

TABLE 6

(IA-vi)

| Example No. | Compound No. | $R^{1A}$ | $R^{4A}$ | $R^{5A}$ |
|---|---|---|---|---|
| 87 | 94 | —H | —CH₂CH₃ | —Ph |
| 88 | 95 | —H | —CH₂NHSO₂CH₃ | —Ph |
| 89 | 96 | —CH₃ | —CH₂NHSO₂CH₃ | —Ph |
| 90 | 97 | —H | —CH₂NHSO₂CH₂CH₃ | —Ph |
| 91 | 98 | —H | —CH₂OCH₃ | —Ph |
| 92 | 99 | —H | —(CH₂)₂NHSO₂CH₃ | —Ph |
| 94 | 101 | —H | —CH₂NHCOCF₃ | —Ph |
| 97 | 104 | —H | —(CH₂)₂N(CH₃)₂ | —Ph |
| 98 | 105 | —H | —(CH₂)₂COOCH₃ | —Ph |
| 99 | 106 | —H | —(CH₂)₂COOH | —Ph |
| 100 | 107 | —H | —(CH₂)₂CONH₂ | —Ph |
| 101 | 108 | —H | —(CH₂)₂CONHOH | —Ph |
| 102 | 109 | —H | —(CH₂)₂CONHCH₃ | —Ph |
| 103 | 110 | —H | —(CH₂)₂CON(CH₃)₂ | —Ph |
| 104 | 111 | —H | —(CH₂)₂CONH(CH₂)₂OH | —Ph |
| 105 | 112 | —H | —(CH₂)₂CONH(CH₂)₃CH₃ | —Ph |
| 106 | 113 | —H | ![propanamide-N-cyclohexyl] | —Ph |
| 107 | 114 | —H | —(CH₂)₃COOCH₃ | —Ph |
| 108 | 115 | —H | —(CH₂)₃COOH | —Ph |
| 109 | 116 | —H | —(CH₂)₃CONHCH₃ | —Ph |
| 110 | 117 | —H | —(CH₂)₃CONH₂ | —Ph |
| 123 | 130 | —H | —CH₃ | 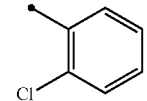 |

TABLE 6-continued
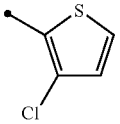
(IA-vi)
| Example No. | Compound No. | $R^{1A}$ | $R^{4A}$ | $R^{5A}$ |
|---|---|---|---|---|
| 128 | 135 | —H | —CH$_3$ | 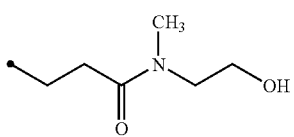 |
| 154 | 161 | —H | 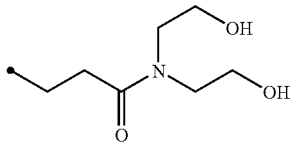 | —Ph |
| 155 | 162 | —H | 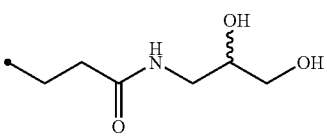 | —Ph |
| 156 | 163 | —H | 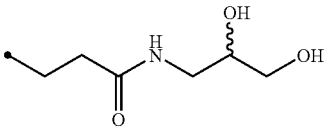 | —Ph |
| 156 | 164 | —H | 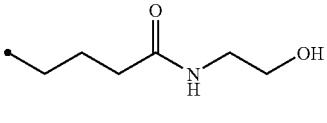 | —Ph |
| 157 | 165 | —H | (structure: —CH$_2$CH$_2$CH$_2$C(=O)NHCH$_2$CH$_2$OH) | —Ph |
| 158 | 166 | —H | —(CH$_2$)$_3$OH | —Ph |
| 159 | 167 | —H | —(CH$_2$)$_3$OSO$_3$NH$_2$ | —Ph |
*Ph: phenyl,
Compound 164: an isomer of Compound 163
TABLE 7
(IA-vii)
| Example No. | Compound No. | $R^{1A}$ | $R^{4A}$ | $R^{5A}$ |
|---|---|---|---|---|
| 93 | 100 | —H | —(CH$_2$)$_2$NHSO$_2$CH$_3$ | —Ph |
| 95 | 102 | —COCH(CH$_3$)$_2$ | —CH$_2$NHSO$_2$CH$_3$ | —Ph |
| 96 | 103 | —H | —CH$_2$NHSO$_2$CH$_3$ | —Ph |

TABLE 7-continued (IA-vii)

[Structure: 1,3,4-thiadiazoline with N-COCH(CH$_3$)$_2$ on ring N, R$^{4A}$ and R$^{5A}$ on C, and N(R$^{1A}$)COCH(CH$_3$)$_2$ substituent]

| Example No. | Compound No. | R$^{1A}$ | R$^{4A}$ | R$^{5A}$ |
|---|---|---|---|---|
| 121 | 128 | —H | —CH$_3$ | 3-(OC(O)CH(CH$_3$)$_2$)phenyl |
| 122 | 129 | —H | —CH$_3$ | 3-hydroxyphenyl |
| 124 | 131 | —H | —CH$_3$ | 2-chlorophenyl |

*Ph: phenyl

TABLE 8

(IA-viii)

[Structure: 1,3,4-thiadiazoline bearing R$^{3A}$ on ring N, R$^{4A}$ and phenyl on C, and NH—R$^{2A}$ substituent]

| Example No. | Compound No. | R$^{2A}$ | R$^{3A}$ | R$^{4A}$ |
|---|---|---|---|---|
| 111 | 118 | —H | —COOH$_3$ | —CH$_2$NHSO$_2$CH$_3$ |
| 112 | 119 | —COC(CH$_3$)$_3$ | —COCH$_3$ | —CH$_2$NHSO$_2$CH$_3$ |
| 113 | 120 | —H | —COC(CH$_3$)$_3$ | —CH$_2$NHSO$_2$CH$_3$ |
| 114 | 121 | —CO(CH$_2$)$_5$Br | —COC(CH$_3$)$_3$ | —CH$_2$NHSO$_2$CH$_3$ |
| 115 | 122 | —CO(CH$_2$)$_5$N$_3$ | —COC(CH$_3$)$_3$ | —CH$_2$NHSO$_2$CH$_3$ |
| 116 | 123 | —CO(CH$_2$)$_5$NH$_2$ | —COC(CH$_3$)$_3$ | —CH$_2$NHSO$_2$CH$_3$ |
| 117 | 124 | —CO(CH$_2$)$_5$NHCOCH$_3$ | —COC(CH$_3$)$_3$ | —CH$_2$NHSO$_2$CH$_3$ |
| 150 | 157 | —H | —COC(CH$_3$)$_3$ | —(CH$_2$)$_2$NHSO$_2$CH$_3$ |
| 151 | 158 | —CO(CH$_2$)$_3$Br | —COC(CH$_3$)$_3$ | —(CH$_2$)$_2$NHSO$_2$CH$_3$ |
| 153 | 160 | —COC(CH$_3$)$_3$ | —CSCH$_3$ | —CH$_2$NHSO$_2$CH$_3$ |
| 160 | 168 | —COC(CH$_3$)$_3$ | —COCH$_3$ | —CH$_2$NHSO$_2$CH$_2$Cl |
| 160 | 169 | —COCH$_3$ | —COCH$_3$ | —CH$_2$NHSO$_2$CH$_2$Cl |
| 161 | 170 | —COC(CH$_3$)$_3$ | —COCH$_3$ | —CH$_2$NHSO$_2$CH=CH$_2$ |
| 161 | 171 | —COC(CH$_3$)$_3$ | —COC(CH$_3$)$_3$ | —CH$_2$NHSO$_2$CH=CH$_2$ |
| 162 | 172 | —COC(CH$_3$)$_3$ | —COCH$_3$ | —CH$_2$NHSO$_2$(CH$_2$)$_2$-(4-morpholinyl) |
| 163 | 173 | —COC(CH$_3$)$_3$ | —COCH$_3$ | —CH$_2$NHSO$_2$(CH$_2$)$_2$NHCH$_2$CH$_3$ |
| 164 | 174 | —COC(CH$_3$)$_3$ | —COCH$_3$ | —CH$_2$NHSO$_2$(CH$_2$)$_2$N(CH$_3$)$_2$ |
| 165 | 175 | —COC(CH$_3$)$_3$ | —COCH$_3$ | —CH$_2$NHSO$_2$(CH$_2$)$_2$NH(CH$_2$)$_2$OH |
| 166 | 176 | —COC(CH$_3$)$_3$ | —COC(CH$_3$)$_3$ | —CH$_2$NHSO$_2$(CH$_2$)$_2$NHCH$_2$CH$_3$ |
| 167 | 177 | —COC(CH$_3$)$_3$ | —COC(CH$_3$)$_3$ | —CH$_2$NHSO$_2$(CH$_2$)$_2$N(CH$_3$)$_2$ |
| 168 | 178 | —H | —COCH$_3$ | —(CH$_2$)$_2$CO$_2$CH$_3$ |
| 169 | 179 | —COC(CH$_3$)$_3$ | —COCH$_3$ | —(CH$_2$)$_2$CO$_2$CH$_3$ |

TABLE 8-continued (IA-viii)

| Example No. | Compound No. | R$^{2A}$ | R$^{3A}$ | R$^{4A}$ |
|---|---|---|---|---|
| 170 | 180 | —H | —COCH(CH$_3$)$_2$ | —(CH$_2$)$_2$NHSO$_2$CH$_3$ |
| 171 | 181 | —COC(CH$_3$)$_3$ | —COCH(CH$_3$)$_2$ | —(CH$_2$)$_2$NHSO$_2$CH$_3$ |
| 174 | 184 | ![](CH$_2$CH$_2$CH$_2$CH$_2$OCH$_3$ with C=O) | —COCH(CH$_3$)$_2$ | —(CH$_2$)$_2$NHSO$_2$CH$_3$ |
| 175 | 185 | —COCH$_2$CH$_3$ | —COCH$_2$CH$_3$ | —(CH$_2$)$_2$NHSO$_2$CH$_3$ |
| 176 | 186 | —H | —COCH$_2$CH$_3$ | —(CH$_2$)$_2$NHSO$_2$CH$_3$ |
| 177 | 187 | —COC(CH$_3$)$_3$ | —COCH$_2$CH$_3$ | —(CH$_2$)$_2$NHSO$_2$CH$_3$ |
| 180 | 190 | —H | —COC(CH$_3$)$_3$ | —(CH$_2$)$_2$COOCH$_3$ |
| 181 | 191 | ![](CH$_2$CH$_2$CH$_2$Br with C=O) | —COC(CH$_3$)$_3$ | —(CH$_2$)$_2$COOCH$_3$ |

TABLE 9

(IA-xii)

| Example No. | Compound No. | R$^{1A}$ | R$^{2A}$ | R$^{3A}$ | R$^{4A}$ |
|---|---|---|---|---|---|
| 152 | 159 | ![](C4 linker with C=O) | | —COC(CH$_3$)$_3$ | —(CH$_2$)$_2$NHSO$_2$CH$_3$ |
| 172 | 182 | ![](C5 linker with C=O) | | —COCH(CH$_3$)$_2$ | —(CH$_2$)$_2$NHSO$_2$CH$_3$ |
| 173 | 183 | ![](C4 linker with C=O) | | —COCH(CH$_3$)$_2$ | —(CH$_2$)$_2$NHSO$_2$CH$_3$ |
| 178 | 188 | ![](C4 linker with C=O) | | —COCH$_2$CH$_3$ | —(CH$_2$)$_2$NHSO$_2$CH$_3$ |
| 179 | 189 | ![](C5 linker with C=O) | | —COCH$_2$CH$_3$ | —(CH$_2$)$_2$NHSO$_2$CH$_3$ |
| 182 | 192 | ![](C4 linker with C=O) | | —COC(CH$_3$)$_3$ | —(CH$_2$)$_2$COOCH$_3$ |

TABLE 9-continued (IA-xii)

| Example No. | Compound No. | R$^{1A}$ | R$^{2A}$ | R$^{3A}$ | R$^{4A}$ |
|---|---|---|---|---|---|
| 183 | 193 | —COC(CH₂CH₂CH₃)=O (pivaloyl-like) | | —COC(CH₃)₃ | —(CH₂)₂COOH |
| 184 | 194 | —COC(CH₂CH₂CH₂CH₃)=O | | —COC(CH₃)₃ | —(CH₂)₂CONH(CH₂)₂OH |

TABLE 10

(IA-xiii)

| Example No. | Compound No. | R$^{2A}$ | R$^{28}$ | Y$^{3A}$ |
|---|---|---|---|---|
| 185 | 195 | —COC(CH₃)₃ | —OCOCH₃ | —H |
| 186 | 196 | —COC(CH₃)₃ | —OH | —H |
| 187 | 197 | —H | —H | —OCOCH₃ |
| 188 | 198 | —COC(CH₃)₃ | —H | —OCOCH₃ |
| 189 | 199 | —COC(CH₃)₃ | —H | —OH |

TABLE 11

(I-ix)

| Example No. | Compound No. | R² | R⁴ |
|---|---|---|---|
| 1 | 1 | —COCH₃ | —CH₃ |
| 3 | 3 | —COCH₃ | —(CH₂)₃CH₃ |
| 6 | 6 | —COOH | —Ph |
| 11 | 14 | —H | —CH₃ |

*Ph: phenyl

TABLE 12

(I-x)

| Example No. | Compound No. | R¹ | R⁴ | R⁵ |
|---|---|---|---|---|
| 19 | 22 | —H | —CH₃ | —CH₃ |
| 20 | 23 | —H | —CH₃ | —(CH₂)₃CH₃ |
| 21 | 24 | —H | —CH₃ | —(CH₂)₂Ph |
| 27 | 30 | —H |  | —(CH₂)₅CH₃ (hexyl) |
| 36 | 39 | —H | —CH₃ | 2-furyl |
| 37 | 40 | —H | —CH₃ | 2-thienyl |

*Ph: phenyl

TABLE 13

(I-xi)

| Example No. | Compound No. | R¹ | R⁴ | Y¹ (Substituting position) |
|---|---|---|---|---|
| 49 | 52 | —H | —CH₃ | —OCH₃ (4) |
| 59 | 62 | —H | —CH₃ | —OCOCH₃ (3) |
| 63 | 66 | —H | —CH₃ | —NO₂ (3) |
| 64 | 67 | —H | —CH₃ | —NO₂ (4) |

Next, the pharmacological activity of typical Compounds (I) will be explained by the following test example.

TEST EXAMPLE 1

Antiproliferative Activity in HCT 116 Human Colon Cancer Cells

HCT 116 cells (ATCC No.: CCL-247) were placed on a 96-well microtiter plate (Nunc, 167008) at a density of $1\times10^3$ cells/well. The plate was incubated in a 5% $CO_2$ incubator at 37° C. for 24 hours, and then to the plate was added test compounds diluted stepwise to 100 mL/well in total, and the plate was further incubated in a 5% $CO_2$ incubator at 37° C. for 72 hours. To the culture medium, the XTT (sodium 3'-[1-(phenylaminocarbonyl)-3,4-tetrazolium]-bis(4-methoxy-6-nitro)benzenesulfonic acid hydrate) labeling mixture (Roche Diagnostics, 1465015) was dispensed in 50 mL/well portions, then the plate was incubated in a 5% $CO_2$ incubator at 37° C. for 1 hour, and the absorbance was measured at 490 nm and 655 nm with a microplate spectrophotometer (Bio-Rad, Model 550). The inhibitory activity against cell proliferation was shown as a concentration of 50% proliferation inhibition, $GI_{50}$.

$GI_{50}$ calculation method: The value (difference in absorbance) was calculated by subtracting the absorbance at 655 nm from the absorbance at 490 nm of each well. The difference in absorbance obtained from the cells untreated with a test compound was defined as 100%, and compared with the difference in absorbance obtained from the cells treated with the solution of the compound in the known concentration, and thereby the concentration of the compound of 50% inhibition against cell proliferation was calculated to obtain $GI_{50}$.

The results of the typical compounds obtained in Test example 1 are shown in Table 14. Compounds 138, 152, 165, 170, 173, and 199 showed the $GI_{50}$ value less than 10 μmol/L.

TABLE 14

| Compound No. | $GI_{50}$ (μmol/L) |
|---|---|
| 1 | 1.0 |
| 7 | 0.48 |
| 18 | 0.62 |
| 41 | 0.60 |
| 46 | 0.57 |
| 57 | 0.53 |
| 69 | 0.23 |
| 82 | 0.18 |
| 99 | 0.063 |
| 104 | 0.074 |
| 107 | 0.061 |
| 134 | 0.40 |

Compound (I) or Compound (IA), or a pharmacologically acceptable salt thereof, per se, can be administered, however, is generally desired to be provided as a form of various pharmaceutical preparations. Also, the pharmaceutical preparations are used for animals or human.

The pharmaceutical preparations according to the present invention can comprise as an active ingredient Compound (I) or Compound (IA), or a pharmacologically acceptable salt thereof, solely or as a mixture with any other effective ingredient for the treatment. The pharmaceutical preparations are manufactured by mixing the active ingredient with one or more of pharmacologically acceptable carriers using any method well known in the technical field of pharmaceutical science.

As for administration routes, it is preferred to chose the most effective route for the treatment such as oral administration or parenteral administration, for example, intravenous administration and the like.

Examples of formulations for administration include tablets, injections and the like.

Examples of the pharmaceutical carrier used include lactose, mannitol, glucose, hydroxypropyl cellulose, starch, magnesium stearate, sorbitan fatty acid ester, glyceric acid ester, polyvinyl alcohol, distilled water for injection, physiological saline, propylene glycol, polyethylene glycol, ethanol and the like. The pharmaceutical preparation according to the present invention may comprise other various additives such as excipients, lubricants, binders, disintegrator, isotonicities and emulsifiers.

Compound (I) or Compound (IA), or a pharmacologically acceptable salt thereof is generally administered systemically or locally in the form of an oral or parenteral preparation when used for the aforementioned purpose. The dose and the frequency of administration may vary depending on the administration form, the age and body weight of a patient, nature and severity of the condition to be treated, and the like. Generally, 0.1 to 1,000 mg/kg, preferably 0.5 to 500 mg/kg per single administration for an adult may be administered orally or parenterally, once a day or a few times a day, or may be continuously administered intravenously for 1 to 24 hours a day. However, the dose and the frequency of administration may vary depending on the aforementioned various conditions and the like.

BEST MODE FOR CARRYING OUT THE INVENTION

The present invention will be explained in detail with reference to the following examples.

The spectra of proton nuclear magnetic resonance ($^1$H NMR) used in Examples were measured at 270 or 300 MHz, and exchangeable hydrogen may not always be clearly observed depending on the compound and the measurement conditions. For the descriptions of the multiplicity of signals, those generally applied are used, and the symbol "br" represents an apparent broad signal.

Example 1

Compound 1

Step 1: Acetophenone (4.00 g, 33.3 mmol) and thiosemicarbazide (3.15 g, 34.6 mmol) were dissolved in methanol (30 mL). To the solution was added hydrochloric acid (0.1 mL) and the mixture was vigorously stirred at room temperature for 15 hours. To the reaction mixture was added water (30 mL), and the deposited crystals were collected by filtration. The collected crystals were washed with water and diisopropyl ether, and then dried to obtain acetophenone=thiosemicarbazone (5.64 g, 88%).

$^1$H NMR (270 MHz, DMSO-$d_6$) δ (ppm): 2.30 (s, 3H), 7.37-7.40 (m, 3H), 7.91-7.94 (m, 3H), 8.27 (br s, 1H), 10.21 (br s, 1H)

Step 2: Acetophenone=thiosemicarbazone (300 mg, 0.889 mmol) obtained above was dissolved in acetic anhydride (1.0 mL, 11 mmol). After being refluxing under heating, the solution was cooled to room temperature with vigorous stirring. To the reaction mixture was added diisopropyl ether (3 mL), and the deposited crystals were collected by filtration. After the collected crystals were suspended in diisopropyl ether and stirred for 3 hours, the crystals were collected by filtration and dried to obtain Compound 1 (195 mg, 72%).

$^1$H NMR (270 MHz, CDCl$_3$) δ (ppm): 2.01 (s, 3H), 2.19 (s, 3H), 2.28 (s, 3H), 7.24-7.36 (br s, 5H), 11.63 (br s, 1H)

Example 2

Compound 2

Step 1: In a manner similar to that in Step 1 of Example 1, propiophenone=thiosemicarbazone (759 mg, 88%) was obtained from propiophenone (541 mg, 3.92 mmol) and thiosemicarbazide (382 mg, 4.18 mmol).

$^1$H NMR (270 MHz, DMSO-d$_6$) δ (ppm): 1.01 (t, J=7.4 Hz, 3H), 2.85 (br q, J=7.4 Hz, 2H), 7.39 (m, 3H), 7.89 (m, 3H), 8.24 (br s, 1H), 10.30 (br s, 1H)

Step 2: In a manner similar to that in Step 2 of Example 1, Compound 2 (601 mg, 76%) was obtained from propiophenone=thiosemicarbazone (559 mg, 2.70 mmol) obtained above.

$^1$H NMR (270 MHz, DMSO-d$_6$) δ (ppm): 1.02 (t, J=7.1 Hz, 3H), 2.00 (s, 3H), 2.21 (s, 3H), 2.38 (dt, J=7.1, 7.3 Hz, 1H), 2.85 (dt, J=7.1, 7.3 Hz, 1H), 7.23-7.38 (m, 5H), 11.59 (br s, 1H)

Example 3

Compound 3

Step 1: In a manner similar to that in Step 1 of Example 1, n-butyl(phenyl)methanone=thiosemicarbazone (589 mg, 63%) was obtained from n-butyl(phenyl)methanone (649 mg, 4.00 mmol) and thiosemicarbazide (367 mg, 4.03 mmol).

$^1$H NMR (270 MHz, DMSO-d$_6$) δ (ppm): 0.99 (t, J=7.3 Hz, 3H), 1.38-1.49 (m, 4H), 2.96-2.99 (m, 2H), 7.37-7.39 (m, 3H), 7.87-7.91 (m, 3H), 8.26 (br s, 1H), 10.36 (br s, 1H)

Step 2: In a manner similar to that in Step 2 of Example 1, Compound 3 (168 mg, 62%) was obtained from n-butyl(phenyl)methanone=thiosemicarbazone (200 mg, 0.850 mmol) obtained above.

$^1$H NMR (270 MHz, CDCl$_3$) δ (ppm): 0.96 (t, J=7.3 Hz, 3H), 1.25-1.34 (m, 1H), 1.36-1.54 (m, 2H), 1.68-1.80 (m, 1H), 2.18 (s, 3H), 2.20-2.26 (m, 1H), 2.26 (s, 3H), 2.99-3.10 (m, 1H), 7.22-7.40 (m, 5H), 8.22 (br s, 1H)

Example 4

Compound 4

Step 1: In a manner similar to that in Step 1 of Example 1, isopropyl(phenyl)methanone=thiosemicarbazone (613 mg, 68%) was obtained from isopropyl(phenyl)methanone (608 mg, 4.10 mmol) and thiosemicarbazide (364 mg, 3.99 mmol).

$^1$H NMR (270 MHz, DMSO-d$_6$) δ (ppm): 1.07 (d, J=6.9 Hz, 6H), 2.82 (m, 1H), 7.28 (br d, J=6.3 Hz, 2H), 7.51-7.60 (m, 3H), 7.78 (br s, 1H), 8.23 (br s, 1H), 8.43 (br s, 1H)

Step 2: In a manner similar to that in Step 2 of Example 1, Compound 4 (217 mg, 52%) was obtained from isopropyl (phenyl)methanone=thiosemicarbazone (300 mg, 1.36 mmol) obtained above.

$^1$H NMR (270 MHz, CDCl$_3$) δ (ppm): 1.04 (d, J=6.9 Hz, 3H), 1.13 (d, J=6.9 Hz, 3H), 2.09 (s, 3H), 2.19 (s, 3H), 3.86 (m, 1H), 7.25-7.36 (m, 3H), 7.75 (br d, J=7.3 Hz, 2H), 8.08 (br s, 1H)

Example 5

Compound 5

In a manner similar to that in Step 1 and 2 of Example 1, Compound 5 (130 mg, 10%) was obtained from cyclopropyl (phenyl)methanone (649 mg, 4.00 mmol) and thiosemicarbazide (367 mg, 4.03 mmol).

$^1$H NMR (270 MHz, CDCl$_3$) δ (ppm): 0.60-0.98 (m, 4H), 1.84 (s, 3H), 2.34 (s, 3H), 2.45 (m, 1H), 7.20-7.35 (m, 3H), 7.54 (br d, J=8.7 Hz, 2H), 9.40 (br s, 1H)

Example 6

Compound 6

In a manner similar to that in Step 1 and 2 of Example 1, Compound 6 (150 mg, 29%) was obtained from benzophenone (0.20 g, 2.19 mmol) and thiosemicarbazide (400 mg, 2.20 mmol).

$^1$H NMR (270 MHz, CDCl$_3$) δ (ppm): 1.89 (s, 3H), 2.32 (s, 3H), 7.25-7.52 (m, 10H), 9.13 (br s, 1H)

Example 7

Compound 7

Step 1: In a manner similar to that in Step 1 of Example 1, acetophenone=4-methylthiosemicarbazone (1.51 g, 77%) was obtained from 4-methylthiosemicarbazide (1.00 g, 9.51 mmol) and acetophenone (1.33 mL, 11.4 mmol).

Step 2: In a manner similar to that in Step 2 of Example 1, Compound 7 (1.03 g, 47%) was obtained from acetophenone=4-methylthiosemicarbazone (1.00 g, 9.51 mmol) obtained above.

$^1$H NMR (270 MHz, DMSO-d$_6$) δ (ppm): 2.21 (s, 3H), 2.23 (s, 3H), 2.26 (s, 3H), 3.41 (s, 3H), 7.28-7.36 (m, 5H)

Example 8

Compounds 8 and 9

To a solution of 60% sodium hydride (110 mg, 2.70 mmol) in N,N-dimethylformamide (10.0 mL) was added Compound 1 (50.0 mg, 1.80 mmol) prepared in Example 1, and the mixture was stirred at room temperature for 30 minutes. To the reaction mixture was added ethyl iodide (0.22 mL, 2.70 mmol) and the reaction mixture was further stirred at room temperature for 12 hours. To the reaction mixture was added 5% aqueous ammonium chloride and the mixture was extracted with ethyl acetate. The organic layer was washed with saturated aqueous sodium chloride and then dried over anhydrous sodium sulfate, and the solvent was evaporated under reduced pressure. The residue was purified by silica gel column chromatography (ethyl acetate/n-hexane=1/1) to obtain Compound 8 (120 mg, 22%) and Compound 9 (330 mg, 60%).

Compound 8

$^1$H NMR (270 MHz, CDCl$_3$) δ (ppm): 1.19 (t, J=7.0 Hz, 6H), 2.23 (s, 3H), 2.41 (s, 3H), 3.26 (q, J=7.0 Hz, 4H), 7.21-7.45 (m, 5H)

Compound 9

$^1$H NMR (270 MHz, CDCl$_3$) δ (ppm): 1.36 (t, J=7.2 Hz, 3H), 2.24 (s, 6H), 2.37 (s, 3H), 3.91 (q, J=7.2 Hz, 2H), 7.22-7.41 (m, 5H)

Example 9

Compounds 10 and 11

In a manner similar to that in Example 8, Compound 10 (0.15 g, 26%) and compound 11 (0.27 g, 48%) were obtained from Compound 1 (0.50 g, 1.80 mmol) prepared in Example 1 and n-propyl iodide (0.26 mL, 2.70 mmol).

Compound 10

$^1$H NMR (270 MHz, CDCl$_3$) δ (ppm): 0.89 (t, J=7.6 Hz, 6H), 1.61 (br q, J=7.6 Hz, 4H), 2.27 (s, 3H), 2.40 (s, 3H), 3.14 (br t, J=7.3 Hz, 4H), 7.21-7.47 (m, 5H)

Compound 11

$^1$H NMR (270 MHz, CDCl$_3$) δ (ppm): 1.00 (t, J=7.3 Hz, 3H), 1.74-1.82 (m, 2H), 2.28 (s, 6H), 2.36 (s, 3H), 3.75-3.86 (m, 2H), 7.21-7.44 (m, 5H)

Example 10

Compounds 12 and 13

In a manner similar to that in Example 8, Compound 12 (120 mg, 16%) and Compound 13 (0.22 g, 33%) were obtained from Compound 1 (500 mg, 1.80 mmol) prepared in Example 1 and benzyl bromide (0.32 mL, 2.70 mmol).

Compound 12

$^1$H NMR (270 MHz, CDCl$_3$) δ (ppm): 2.24 (s, 3H), 2.46 (s, 3H), 4.43 (s, 4H), 7.14-7.49 (m, 15H)

Compound 13

$^1$H NMR (270 MHz, CDCl$_3$) δ (ppm): 2.16 (s, 3H), 2.26 (s, 3H), 2.36 (s, 3H), 5.11 (br s, 2H), 7.22-7.38 (m, 10H)

Example 11

Compound 14

To acetophenone=thiosemicarbazone (10.0 g, 51.8 mmol) prepared in Step 1 of Example 1 was added acetic anhydride (4.90 mL, 51.9 mmol) and pyridine (8.40 mL, 104 mmol), and the mixture was stirred at room temperature for 12 hours. After the reaction mixture was concentrated under reduced pressure, ethyl acetate and 2 mol/L aqueous sodium hydroxide was added, and the mixture was subjected to separation. The organic layer was washed with saturated aqueous ammonium chloride and saturated aqueous sodium chloride, and dried over anhydrous sodium sulfate, and then the solvent was evaporated under reduced pressure. The residue was purified by silica gel column chromatography (ethyl acetate/n-hexane=1/1) to obtain Compound 14 (9.22 g, 76%).

$^1$H NMR (270 MHz, DMSO-d$_6$) δ (ppm): 2.12 (s, 3H), 2.31 (s, 3H), 6.49 (br s, 2H), 7.21-7.41 (m, 5H)

Example 12

Compound 15

Compound 7 (550 mg, 1.89 mmol) prepared in Example 7 was dissolved in N,N-dimethylformamide (10.0 mL). To the solution was added 60% sodium hydride (0.23 g, 5.75 mmol) and the mixture was stirred at room temperature for 30 minutes. To the reaction mixture was added water and the mixture was extracted with ethyl acetate. The organic layer was washed with saturated aqueous ammonium chloride and then dried over anhydrous sodium sulfate, and the solvent was evaporated under reduced pressure. The residue was purified by silica gel column chromatography (ethyl acetate/n-hexane=1/1) to obtain Compound 15 (0.31 g, 66%).

$^1$H NMR (270 MHz, CDCl$_3$) δ (ppm): 2.17 (s, 3H), 2.41 (s, 3H), 2.91 (br d, J=5.0 Hz, 3H), 3.92 (br s, 1H), 7.25-7.47 (m, 5H)

Example 13

Compound 16

To a solution of 60% sodium hydride (50.0 mg, 1.20 mmol) in N,N-dimethylformamide (2.0 mL) was added Compound 14 (100 mg, 0.41 mmol) prepared in Example 11, and the mixture was stirred at room temperature for 30 minutes. To the reaction mixture was added methyl iodide (0.08 mL, 1.24 mmol), and the mixture was further stirred at room temperature for 12 hours. To the reaction mixture was added 5% aqueous ammonium chloride and the mixture was extracted with ethyl acetate. The organic layer was washed with saturated aqueous sodium chloride and then dried over anhydrous sodium sulfate, and the solvent was evaporated under reduced pressure. The residue was purified by silica gel column chromatography (ethyl acetate/n-hexane 1/1) to obtain Compound 16 (70.0 mg, 67%).

$^1$H NMR (270 MHz, CDCl$_3$) δ (ppm): 2.26 (s, 3H), 2.41 (s, 3H), 2.91 (s, 6H), 7.23-7.48 (m, 5H)

Example 14

Compound 17

In a manner similar to that in Example 12, Compound 17 (580 mg, 71%) was obtained from Compound 19 (1.00 g, 3.13 mmol) obtained in the after-mentioned Example 16.

$^1$H NMR (270 MHz, CDCl$_3$) δ (ppm): 1.13 (t, J=7.2 Hz, 3H), 2.39 (s, 3H), 2.61 (q, J=7.2 Hz, 2H), 2.88 (d, J=6.3 Hz, 3H), 4.02 (br d, J=6.3 Hz, 1H), 7.22-7.38 (m, 5H)

Example 15

Compound 18

Compound 17 (100 mg, 0.38 mmol) prepared in Example 14 was dissolved in acetone (2.0 mL). To the solution was added acetyl chloride (0.15 mL, 2.11 mmol) and pyridine (0.15 mL, 1.85 mmol), and the mixture was stirred at room temperature for 2 hours. To the reaction mixture was added ethyl acetate and 2 mol/L aqueous sodium hydroxide, and the solution was subjected to separation. The organic layer was washed with saturated aqueous ammonium chloride and saturated aqueous sodium chloride, and dried over anhydrous sodium sulfate, and then the solvent was evaporated under reduced pressure. The residue was purified by silica gel column chromatography (ethyl acetate/n-hexane=1/2) to obtain Compound 18 (0.07 g, 59%).

¹H NMR (270 MHz, CDCl₃) δ (ppm): 1.12 (t, J=7.6 Hz, 3H), 2.27 (s, 3H), 2.35 (s, 3H), 2.65 (q, J=7.6 Hz, 2H), 3.45 (s, 3H), 7.23-7.42 (m, 5H)

Example 16

Compound 19

To acetophenone=4-methylthiosemicarbazone (2.00 g, 9.66 mmol) prepared in Step 1 of Example 7 was added propionic anhydride (8.67 mL, 67.6 mmol), and the mixture was heated and stirred at 100° C. for 3 hours. To the reaction mixture was added ethyl acetate and 2 mol/L aqueous sodium hydroxide. After the mixture was stirred at room temperature for 30 minutes, the mixture was subjected to separation. The organic layer was washed with saturated aqueous ammonium chloride and saturated aqueous sodium chloride, and dried over anhydrous sodium sulfate, and then the solvent was evaporated under reduced pressure. The residue was purified by silica gel column chromatography (ethyl acetate/n-hexane=1/2) to obtain Compound 19 (1.39 g, 45%).

¹H NMR (270 MHz, CDCl₃) δ (ppm): 1.12 (t, J=7.3 Hz, 3H), 1.17 (t, J=7.5 Hz, 3H), 2.36 (s, 3H), 2.54 (q, J=7.3 Hz, 2H), 2.66 (q, J=7.5 Hz, 2H), 3.45 (s, 3H), 7.21-7.42 (m, 5H)

Example 17

Compound 20

In a manner similar to that in Example 16, Compound 20 (1.55 g, 46%) was obtained from acetophenone=4-methylthiosemicarbazone (2.00 g, 9.66 mmol) prepared in Step 1 of Example 7 and butyric anhydride (11.1 mL, 67.8 mmol).

¹H NMR (270 MHz, CDCl₃) d(ppm): 0.95 (t, J=7.3 Hz, 3H), 0.98 (t, J=7.4 Hz, 3H), 1.15-1.78 (m, 4H), 2.35 (s, 3H), 2.49 (t, J=7.3 Hz, 2H), 2.61 (t, J=7.4 Hz, 2H), 3.45 (s, 3H), 7.21-7.42 (m, 5H)

Example 18

Compound 21

In a manner similar to that in Example 16, Compound 21 (1.43 g, 43%) was obtained from acetophenone=4-methylthiosemicarbazone (2.00 g, 9.66 mmol) prepared in Step 1 of Example 7 and isobutyric anhydride (11.2 mL, 67.5 mmol).

¹H NMR (270 MHz, CDCl₃) δ (ppm): 1.05-1.25 (m, 12H), 2.34 (s, 3H), 2.99 (q, J=7.3 Hz, 1H), 3.25 (q, J=7.5 Hz, 1H), 3.50 (s, 3H), 7.21-7.45 (m, 5H)

Example 19

Compound 22

Step 1: In a manner similar to that in Step 1 of Example 1, acetone=thiosemicarbazone (215 mg, 41%) was obtained from acetone (4.8 g, 40 mmol) and thiosemicarbazide (364 mg, 3.99 mmol).

¹H NMR (270 MHz, DMSO-d₆) δ (ppm): 1.89 (s, 3H), 1.91 (s, 3H), 7.51 (br s, 1H), 7.98 (br s, 1H), 9.90 (br s, 1H)

Step 2: In a manner similar to that in Step 2 of Example 1, Compound 22 (151 mg, 61%) was obtained from acetone=thiosemicarbazone (150 mg, 1.14 mmol) prepared above.

¹H NMR (270 MHz, CDCl₃) δ (ppm): 1.98 (s, 6H), 2.19 (s, 3H), 2.20 (s, 3H), 9.06 (br s, 1H)

Example 20

Compound 23

Step 1: In a manner similar to that in Step 1 of Example 1, 2-hexanone=thiosemicarbazone (671 mg, 97%) was obtained from 2-hexanone (401 mg, 4.00 mmol) and thiosemicarbazide (364 mg, 3.99 mmol).

¹H NMR (270 MHz, DMSO-d₆) δ (ppm): 0.88 (t, J=6.9 Hz, 3H), 1.23-1.31 (m, 2H), 1.41-1.50 (m, 2H), 1.88 (s, 3H), 2.17-2.23 (m, 2H), 7.44 (br s, 1H), 8.02 (br s, 1H), 9.88 (br s, 1H)

Step 2: In a manner similar to that in Step 2 of Example 1, Compound 23 (255 mg, 57%) was obtained from 2-hexanone=thiosemicarbazone (300 mg, 1.73 mmol) prepared above.

¹H NMR (270 MHz, CDCl₃) δ (ppm): 0.90 (t, J=6.9 Hz, 3H), 1.23-1.38 (m, 3H), 1.52-1.56 (m, 1H), 1.84-2.18 (m, 1H), 1.97 (s, 3H), 2.18 (s, 3H), 2.19 (s, 3H), 2.44-2.55 (m, 1H), 8.68 (br s, 1H)

Example 21

Compound 24

Step 1: In a manner similar to that in Step 1 of Example 1, benzylacetone=thiosemicarbazone (788 mg, 89%) was obtained from benzylacetone (593 mg, 4.00 mmol) and thiosemicarbazide (367 mg, 4.03 mmol).

¹H NMR (270 MHz, DMSO-d₆) δ (ppm): 1.92 (s, 3H), 2.52 (m, 2H), 2.84 (m, 2H), 7.14-7.30 (m, 5H), 7.43 (br s, 1H), 8.03 (br s, 1H), 9.94 (br s, 1H)

Step 2: In a manner similar to that in Step 2 of Example 1, Compound 24 (382 mg, 92%) was obtained from benzylacetone=thiosemicarbazone (300 mg, 1.36 mmol) prepared above.

¹H NMR (270 MHz, CDCl₃) δ (ppm): 2.00 (s, 3H), 2.17 (s, 3H), 2.13 (dd, J=2.3, 10.2 Hz, 1H), 2.19 (s, 3H), 2.59 (dd, J=2.2, 10.2 Hz, 1H), 2.87 (br d, J=12.2 Hz, 1H), 2.95 (br s, J=11.8 Hz, 1H), 7.14-7.29 (m, 5H), 8.39 (br s, 1H)

Example 22

Compound 25

Step 1: In a manner similar to that in Step 1 of Example 1, benzylideneacetone=thiosemicarbazone (730 mg, 80%) was obtained 1 from benzylideneacetone (610 mg, 4.17 mmol) and thiosemicarbazide (371 mg, 4.07 mmol).

¹H NMR (300 MHz, CDCl₃) δ (ppm): 2.13 (s, 3H), 6.89 (d, J=16.8 Hz, 1H), 7.10 (d, J=16.8 Hz, 1H), 7.27-7.41 (m, 3H), 7.43-7.56 (m, 2H), 7.78 (br s, 1H), 8.26 (br s, 1H), 10.27 (br s, 1H)

Step 2: In a manner similar to that in Step 2 of Example 1, Compound 25 (195 mg, 72%) was obtained from benzylideneacetone=thiosemicarbazone (300 mg, 0.889 mmol) prepared above.

¹H NMR (300 MHz, DMSO-d₆) δ (ppm): 2.13 (s, 3H), 2.15 (s, 3H), 2.23 (s, 3H), 6.62 (d, J=12.2 Hz, 1H), 6.65 (d, J=12.2 Hz, 1H), 7.20-7.39 (m, 5H), 8.57 (br s, 1H)

Example 23

Compound 26

Step 1: In a manner similar to that in Step 1 of Example 1, 5-Nonanone=thiosemicarbazone (553 mg, 64%) was obtained from 5-nonanone (569 mg, 4.00 mmol) and thiosemicarbazide (364 mg, 3.99 mmol).

$^1$H NMR (270 MHz, DMSO-d$_6$) δ (ppm): 0.87 (t, J=6.9 Hz, 6H), 1.20-1.53 (m, 8H), 2.17-2.22 (m, 2H), 2.31-2.37 (m, 2H), 7.40 (br s, 1H), 8.00 (br s, 1H), 10.03 (br s, 1H)

Step 2: In a manner similar to that in Step 2 of Example 1, Compound 26 (245 mg, 59%) was obtained from 5-nonanone=thiosemicarbazone (300 mg, 1.39 mmol) prepared above.

$^1$H NMR (270 MHz, CDCl$_3$) δ (ppm): 0.90 (t, J=6.9 Hz, 6H), 1.18-1.37 (m, 6H), 1.55-1.63 (m, 2H), 1.77-1.88 (m, 2H), 2.18 (s, 3H), 2.19 (s, 3H), 2.45-2.56 (m, 2H), 8.90 (br s, 1H)

Example 24

Compound 27

Step 1: In a manner similar to that in Step 1 of Example 1, a-tetralone=thiosemicarbazone (797 mg, 88%) was obtained from a-tetralone (604 mg, 4.13 mmol) and thiosemicarbazide (368 mg, 4.04 mmol).

$^1$H NMR (270 MHz, DMSO-d$_6$) δ (ppm): 1.78-1.82 (m, 2H), 2.65-2.75 (m, 4H), 7.15-7.27 (m, 3H), 7.97 (br s, 1H), 8.20-8.40 (m, 2H), 10.10 (br s, 1H)

Step 2: In a manner similar to that in Step 2 of Example 1, Compound 27 (324 mg, 78%) was obtained from a-tetralone=thiosemicarbazone (300 mg, 1.37 mmol) prepared above.

$^1$H NMR (270 MHz, CDCl$_3$) δ (ppm): 1.89 (s, 3H), 2.09-2.22 (m, 2H), 2.28 (s, 3H), 2.36-2.41 (m, 1H), 2.80-2.86 (m, 2H), 2.97-3.08 (m, 1H), 7.01 (br d, J=8.6 Hz, 1H), 7.08-7.18 (m, 2H), 7.40 (br d, J=7.3 Hz, 1H), 9.24 (br s, 1H)

Example 25

Compound 28

Step 1: In a manner similar to that in Step 1 of Example 1, β-tetralone=thiosemicarbazone (684 mg, 75%) was obtained from B-tetralone (607 mg, 4.15 mmol) and thiosemicarbazide (379 mg, 4.16 mmol).

Step 2: In a manner similar to that in Step 2 of Example 1, Compound 28 (301 mg, 65%) was obtained from B-tetralone=thiosemicarbazone (334 mg, 1.53 mmol) prepared above.

$^1$H NMR (270 MHz, DMSO-d$_6$) δ (ppm): 2.12 (s, 3H), 2.15-2.30 (m, 1H), 2.24 (s, 3H), 3.05-3.09 (m, 2H), 3.14 (br d, J=15.8 Hz, 1H), 3.23-3.41 (m, 1H), 4.38 (br d, J=15.8 Hz, 1H), 6.99-7.00 (m, 1H), 7.02-7.25 (m, 3H), 8.42 (br s, 1H)

Example 26

Compound 29

Step 1: In a manner similar to that in Step 1 of Example 1, 1-indanone=thiosemicarbazone (1.54 g, 94%) was obtained from 1-indanone (1.06 g, 8.00 mmol) and thiosemicarbazide (740 mg, 8.12 mmol).

$^1$H NMR (270 MHz, DMSO-d$_6$) δ (ppm): 2.85-2.89 (m, 2H), 3.03-3.08 (m, 2H), 7.28-7.38 (m, 3H), 7.87 (br d, J=7.6 Hz, 1H), 7.92 (br s, 1H), 8.17 (br s, 1H), 10.2 (br s, 1H)

Step 2: In a manner similar to that in Step 2 of Example 1, Compound 29 (184 mg, 44%) was obtained from 1-indanone=thiosemicarbazone (300 mg, 1.46 mmol) prepared above.

$^1$H NMR (270 MHz, CDCl$_3$) δ (ppm): 2.17 (s, 3H), 2.24 (s, 3H), 2.58-2.65 (m, 1H), 2.96-3.07 (m, 1H), 3.13-3.21 (m, 2H), 7.15-7.27 (m, 3H), 7.32-7.37 (m, 1H), 9.60 (br s, 1H)

Example 27

Compound 30

Step 1: In a manner similar to that in Step 1 of Example 1, cyclohexanone=thiosemicarbazone (479 mg, 70%) was obtained from cyclohexanone (393 mg, 4.00 mmol) and thiosemicarbazide (364 mg, 3.99 mmol).

$^1$H NMR (270 MHz, DMSO-d$_6$) δ (ppm): 1.55 (br s, 6H), 2.19-2.23 (m, 2H), 2.38 (br s, 2H), 7.50 (br s, 1H), 7.93 (br s, 1H), 10.13 (br s, 1H)

Step 2: In a manner similar to that in Step 2 of Example 1, Compound 30 (214 mg, 72%) was obtained from cyclohexanone=thiosemicarbazone (200 mg, 1.17 mmol) prepared above.

$^1$H NMR (300 MHz, CDCl$_3$) δ (ppm): 1.25-1.53 (m, 3H), 1.58-1.68 (m, 1H), 1.81-1.86 (m, 2H), 2.03-2.08 (m, 2H), 2.16 (s, 3H), 2.17 (s, 3H), 2.90-3.01 (m, 2H), 7.95 (br s, 1H)

Example 28

Compound 31

In a manner similar to that in Step 1 and 2 of Example 1, Compound 31 (214 mg, 20%) was obtained from 2-norbornanone (452 mg, 4.10 mmol) and thiosemicarbazide (377 mg, 4.14 mmol).

$^1$H NMR (270 MHz, CDCl$_3$) δ (ppm): 1.32-1.67 (m, 5H), 1.76-1.89 (m, 2H), 2.18 (s, 3H), 2.19 (br s, 1H), 2.21 (s, 3H), 2.26 (br s, 1H), 3.60 (br d, J=13.9 Hz, 1H), 8.20 (br s, 1H)

Example 29

Compound 32

In a manner similar to that in Step 1 and 2 of Example 1, Compound 32 (214 mg, 32%) was obtained from 1'-acetonaphthone (344 mg, 2.02 mmol) and thiosemicarbazide (190 mg, 2.08 mmol).

$^1$H NMR (270 MHz, CDCl$_3$) δ (ppm): 2.06 (s, 3H), 2.07 (s, 3H), 2.33 (s, 3H), 7.45-7.65 (m, 4H), 7.89-7.99 (m, 3H), 11.50 (br s, 1H)

Example 30

Compound 33

Step 1: In a manner similar to that in Step 1 of Example 1, 2'-acetonaphthone=thiosemicarbazone (448 mg, 92%) was obtained from 2'-acetonaphthone (342 mg, 2.10 mmol) and thiosemicarbazide (189 mg, 2.07 mmol).

$^1$H NMR (270 MHz, DMSO-d$_6$) δ (ppm): 2.42 (s, 3H), 7.53 (m, 2H), 7.86-8.05 (m, 4H), 8.28-8.34 (m, 3H), 10.28 (br s, 1H)

Step 2: In a manner similar to that in Step 2 of Example 1, Compound 33 (302 mg, 90%) was obtained from 2'-acetonaphthone=thiosemicarbazone (250 mg, 1.03 mmol) prepared above.

$^1$H NMR (270 MHz, DMSO-d$_6$) δ (ppm): 2.02 (s, 3H), 2.22 (s, 3H), 2.38 (s, 3H), 7.51-7.55 (m, 3H), 7.85-7.95 (m, 4H), 11.68 (br s, 1H)

Example 31

Compound 34

Step 1: In a manner similar to that in Step 1 of Example 1, 1-(2-pyridyl)ethanone=thiosemicarbazone (694 mg, 88%) was obtained from 2-acetylpyridine (485 mg, 4.00 mmol) and thiosemicarbazide (369 mg, 4.05 mmol).

$^1$H NMR (270 MHz, DMSO-$d_6$) δ (ppm): 2.38 (8, 3H), 7.37 (br t, J=6.3 Hz, 1H), 7.78 (br t, J=7.2 Hz, 1H), 8.13 (br s, 1H), 8.40 (br s, 1H), 8.41 (br d, J=8.2 Hz, 1H), 8.56 (br d, J=6.6 Hz, 1H), 10.31 (br s, 1H)

Step 2: In a manner similar to that in Step 2 of Example 1, Compound 34 (160 mg, 37%) was obtained from 1-(2-pyridyl)ethanone=thiosemicarbazone (304 mg, 1.56 mmol) prepared above.

$^1$H NMR (270 MHz, CDCl$_3$) δ (ppm): 2.09 (s, 3H), 2.26 (s, 3H), 2.42 (s, 3H), 7.17 (br t, J=6.9 Hz, 1H), 7.38 (br d, J=8.2 Hz, 1H), 7.68 (br t, J=7.7 Hz, 1H), 8.44 (br s, 1H), 8.58 (br d, J=6.3 Hz, 1H)

Example 32

Compound 35

Step 1: In a manner similar to that in Step 1 of Example 1, 1-(3-pyridyl)ethanone=thiosemicarbazone (722 mg, 93%) was obtained from 3-acetylpyridine (484 mg, 4.00 mmol) and thiosemicarbazide (388 mg, 4.00 mmol).

$^1$H NMR (270 MHz, DMSO-$d_6$) δ (ppm): 2.32 (s, 3H), 7.32-7.42 (m, 1H), 8.07 (br s, 1H), 8.29-8.34 (m, 2H), 8.54-8.57 (m, 1H), 9.09 (br s, 1H), 10.32 (br s, 1H)

Step 2: In a manner similar to that in Step 2 of Example 1, Compound 35 (213 mg, 72%) was obtained from 1-(3-pyridyl)ethanone=thiosemicarbazone (205 mg, 1.05 mmol) prepared above.

$^1$H NMR (270 MHz, CDCl$_3$) δ (ppm): 2.14 (s, 3H), 2.21 (s, 3H), 2.39 (s, 3H), 7.31 (br dd, J=5.4, 7.9 Hz, 1H), 7.75 (br d, J=7.9 Hz, 1H), 8.52 (br d, J=5.4 Hz, 1H), 8.72 (br s, 1H), 9.08 (br s, 1H)

Example 33

Compound 36

Step 1: In a manner similar to that in Step 1 of Example 1, 1-(4-pyridyl)ethanone=thiosemicarbazone (722 mg, 95%) was obtained from 4-acetylpyridine (507 mg, 4.19 mmol) and thiosemicarbazide (408 mg, 4.46 mmol).

Step 2: In a manner similar to that in Step 2 of Example 1, Compound 36 (389 mg, 85%) was obtained from 1-(4-pyridyl)ethanone=thiosemicarbazone (318 mg, 1.64 mmol) prepared above.

$^1$H NMR (270 MHz, CDCl$_3$) δ (ppm): 2.16 (s, 3H), 2.25 (s, 3H), 2.35 (s, 3H), 7.30 (d, J=6.3 Hz, 2H), 8.46 (br s, 1H), 8.60 (d, J=6.3 Hz, 2H)

Example 34

Compound 37

Step 1: In a manner similar to that in Step 1 of Example 1, 1-pyrazinylethanone=thiosemicarbazone (714 mg, 92%) was obtained from acetylpyrazine (489 mg, 4.00 mmol) and thiosemicarbazide (366 mg, 4.00 mmol).

Step 2: In a manner similar to that in Step 2 of Example 1, Compound 37 (489 mg, 85%) was obtained from 1-pyrazinylethanone=thiosemicarbazone (400 mg, 2.05 mmol) prepared above.

$^1$H NMR (270 MHz, CDCl$_3$) δ (ppm): 2.16 (s, 3H), 2.26 (s, 3H), 2.42 (s, 3H), 8.06 (br s, 1H), 8.46 (d, J=2.7 Hz, 1H), 8.52 (dd, J=1.7, 2.7 Hz, 1H), 8.71 (d, J=1.7 Hz, 1H)

Example 35

Compound 38

Step 1: In a manner similar to that in Step 1 of Example 1, 1-(2-pyrrolyl)ethanone=thiosemicarbazone (408 mg, 55%) was obtained from 2-acetylpyrrole (437 mg, 4.00 mmol) and thiosemicarbazide (374 mg, 4.09 mmol).

Step 2: In a manner similar to that in Step 2 of Example 1, Compound 38 (504 mg, 95%) was obtained from 1-(2-pyrrolyl)ethanone=thiosemicarbazone (314 mg, 1.72 mmol) prepared above.

$^1$H NMR (270 MHz, CDCl$_3$) δ (ppm): 2.12 (s, 3H), 2.21 (s, 3H), 2.38 (s, 3H), 2.55 (s, 3H), 6.17-6.22 (m, 2H), 7.11 (br s, 1H), 8.13 (br s, 1H)

Example 36

Compound 39

Step 1: In a manner similar to that in Step 1 of Example 1, 1-(2-furyl)ethanone=thiosemicarbazone (441 mg, 60%) was obtained from 2-acetylfuran (444 mg, 4.00 mmol) and thiosemicarbazide (368 mg, 4.03 mmol).

Step 2: In a manner similar to that in Step 2 of Example 1, Compound 39 (217 mg, 83%) was obtained from 1-(2-furyl)ethanone=thiosemicarbazone (180 mg, 0.982 mmol) prepared above.

$^1$H NMR (270 MHz, CDCl$_3$) δ (ppm): 2.13 (s, 3H), 2.22 (s, 3H), 2.30 (s, 3H), 6.31 (m, 2H), 7.36 (br s, 1H), 8.43 (br s, 1H)

Example 37

Compound 40

Step 1: In a manner similar to that in Step 1 of Example 1, 1-(2-thienyl)ethanone=thiosemicarbazone (636 mg, 78%) was obtained from 2-acetylthiophene (521 mg, 4.13 mmol) and thiosemicarbazide (376 mg, 4.11 mmol).

Step 2: In a manner similar to that in Step 2 of Example 1, Compound 40 (549 mg, 78%) was obtained from 1-(2-thienyl)ethanone=thiosemicarbazone (498 mg, 2.50 mmol) prepared above.

$^1$H NMR (300 MHz, CDCl$_3$) δ (ppm): 2.07 (s, 3H), 2.24 (s, 3H), 2.42 (s, 3H), 6.89 (br t, J=7.2 Hz, 1H), 7.06 (dd, J=6.9, 7.2 Hz 1H), 7.24 (br d, J=6.9 Hz, 1H), 8.81 (br s, 1H)

Example 38

Compound 41

In a manner similar to that in Example 8, Compound 41 (148 mg, 52%) was obtained in from Compound 40 (260 mg, 0.918 mmol) prepared in Example 37.

$^1$H NMR (270 MHz, CDCl$_3$) δ (ppm): 1.36 (t, J=7.0 Hz, 31H), 2.25 (s, 3H), 2.30 (s, 3H), 2.43 (s, 3H), 3.92 (br q, J=7.0 Hz, 2H), 6.91 (br t, J=5.2 Hz, 1H), 7.06 (br d, J=5.2 Hz, 1H), 7.24 (br d, J=5.2 Hz, 1H)

Example 39

Compound 42

Step 1: In a manner similar to that in Step 1 of Example 1, 1-(3-methyl-2-thienyl)ethanone=thiosemicarbazone (410 mg, 48%) was obtained from 2-acetyl-3-methylthiophene (561 mg, 4.00 mmol) and thiosemicarbazide (374 mg, 4.09 mmol).

Step 2: In a manner similar to that in Step 2 of Example 1, Compound 42 (335 mg, 93%) was obtained from 1-(3-methyl-2-thienyl)ethanone=thiosemicarbazone (260 mg, 1.22 mmol) prepared above.

$^1$H NMR (270 MHz, CDCl$_3$) δ (ppm): 2.02 (s, 3H), 2.19 (s, 3H), 2.24 (s, 3H), 2.38 (s, 3H) 6.78 (d, J=5.0 Hz, 1H), 7.07 (d, J=5.0 Hz, 1H), 9.37 (br s, 1H)

Example 40

Compound 43

Step 1: In a manner similar to that in Step 1 of Example 1, 1-(benzo[b]thiophen-2-yl)ethanone=thiosemicarbazone (990 mg, 99%) was obtained from 1-(benzo[b]thiophen-2-yl)ethanone (705 mg, 4.00 mmol) and thiosemicarbazide (370 mg, 4.05 mmol).

$^1$H NMR (270 MHz, DMSO-d$_6$) δ (ppm): 2.40 (s, 3H), 7.36-7.41 (m, 2H), 7.45 (br s, 1H), 7.81-7.90 (m, 3H), 8.42 (br s, 1H), 10.56 (br s, 1H)

Step 2: In a manner similar to that in Step 2 of Example 1, Compound 43 (599 mg, 90%) was obtained from 1-(benzo[b]thiophen-2-yl)ethanone=thiosemicarbazone (500 mg, 2.01 mmol) prepared above.

$^1$H NMR (270 MHz, DMSO-d$_6$) δ (ppm): 2.04 (s, 3H), 2.17 (s, 3H), 2.38 (s, 3H), 7.31-7.40 (m, 3H), 7.79 (br d, J=7.6 Hz, 1H), 7.89 (br d, J=7.8 Hz, 1H), 11.75 (br s, 1H)

Example 41

Compound 44

Step 1: In a manner similar to that in Step 1 of Example 1, 1-(3-thienyl)ethanone=thiosemicarbazone (839 mg, 98%) was obtained from 3-acetylthiophene (520 mg, 4.12 mmol) and thiosemicarbazide (366 mg, 4.00 mmol).

$^1$H NMR (270 MHz, DMSO-d$_6$) δ (ppm): 2.27 (s, 3H), 7.52 (br d, J=5.3 Hz, 1H), 7.83 (br d, J=5.3 Hz, 1H), 7.96 (br s, 1H), 8.22 (br s, 1H), 10.08 (br s, 1H)

Step 2: In a manner similar to that in Step 2 of Example 1, Compound 44 (540 mg, 83%) was obtained from 1-(3-thienyl)ethanone=thiosemicarbazone (458 mg, 2.30 mmol) prepared above.

$^1$H NMR (270 MHz, DMSO-d$_6$) δ (ppm): 2.02 (s, 3H), 2.15 (s, 3H), 2.25 (s, 3H), 7.05 (br d, J=6.0 Hz, 1H), 7.37 (br s, 1H), 7.47 (br d, J=6.0 Hz, 1H)

Example 42

Compound 45

Step 1: In a manner similar to that in Step 1 of Example 1, 1-(2-thiazolyl)ethanone=thiosemicarbazone (711 mg, 90%) was obtained from 2-acetylthiazole (379 mg, 4.15 mmol) and thiosemicarbazide (366 mg, 4.00 mmol).

$^1$H NMR (270 MHz, DMSO-d$_6$) δ (ppm): 2.42 (s, 3H), 7.67 (br s, 1H), 7.79 (br d, J=4.3 Hz, 1H), 7.87 (br d, J=4.3 Hz, 1H), 8.51 (br s, 1H), 10.65 (br s, 1H)

Step 2: In a manner similar to that in Step 2 of Example 1, Compound 45 (374 mg, 45%) was obtained from 1-(2-thiazolyl)ethanone=thiosemicarbazone (374 mg, 1.87 mmol) prepared above.

$^1$H NMR (270 MHz, DMSO-d$_6$) δ (ppm): 2.03 (s, 3H), 2.18 (s, 3H), 2.31 (s, 3H), 7.74-7.79 (m, 2H), 11.70 (br s, 1H)

Example 43

Compound 46

In a manner similar to that in Step 1 and 2 of Example 1, Compound 46 (141 mg, 10%) was obtained from 2'-methylacetophenone (627 mg, 4.67 mmol) and thiosemicarbazide (374 mg, 4.09 mmol).

$^1$H NMR (270 MHz, CDCl$_3$) δ (ppm): 1.99 (br s, 1H), 2.21 (s, 3H), 2.33 (s, 3H), 2.38 (s, 3H), 7.15-7.20 (m, 3H), 7.38 (m, 1H), 8.90 (br s, 1H)

Example 44

Compound 47

Step 1: In a manner similar to that in Step 1 of Example 1, 3'-methylacetophenone=thiosemicarbazone (791 mg, 89%) was obtained from 3'-methylacetophenone (540 mg, 4.02 mmol) and thiosemicarbazide (369 mg, 4.04 mmol).

Step 2: In a manner similar to that in Step 2 of Example 1, Compound 47 (316 mg, 79%) was obtained from 3'-methylacetophenone=thiosemicarbazone (300 mg, 1.36 mmol) prepared above.

$^1$H NMR (270 MHz, CDCl$_3$) δ (ppm): 2.15 (s, 3H), 2.23 (s, 3H), 2.34 (s, 3H), 2.37 (s, 3H), 7.01-7.09 (m, 1H), 7.19-7.30 (m, 3H), 7.90 (br s, 1H)

Example 45

Compound 48

Step 1: In a manner similar to that in Step 1 of Example 1, 4'-methylacetophenone=thiosemicarbazone (767 mg, 93%) was obtained from 4'-methylacetophenone (536 mg, 3.99 mmol) and thiosemicarbazide (382 mg, 4.19 mmol).

$^1$H NMR (270 MHz, DMSO-d$_6$) δ (ppm): 2.27 (s, 3H), 2.32 (s, 3H), 7.18 (d, J=7.9 Hz, 2H), 7.82 (d, J=7.9 Hz, 2H), 7.88 (br s, 1H), 8.23 (br s, 1H), 10.15 (br s, 1H)

Step 2: In a manner similar to that in Step 2 of Example 1, Compound 48 (224 mg, 80%) was obtained from 4'-methylacetophenone=thiosemicarbazone (200 mg, 0.965 mmol) prepared above.

$^1$H NMR (270 MHz, DMSO-d$_6$) δ (ppm): 2.06 (s, 3H), 2.24 (s, 3H), 2.31 (s, 3H), 2.36 (s, 3H), 7.13 (d, J=8.3 Hz, 2H), 7.31 (d, J=8.3 Hz, 2H), 8.40 (br s, 1H)

Example 46

Compound 49

Step 1: In a manner similar to that in Step 1 of Example 1, 2'-ethylpropiophenone=thiosemicarbazone (672 mg, 71%) was obtained from 2'-ethylpropiophenone (649 mg, 4.00 mmol) and thiosemicarbazide (378 mg, 4.14 mmol).

Step 2: In a manner similar to that in Step 2 of Example 1, Compound 49 (759 mg, 88%) was obtained from 2'-ethylpropiophenone=thiosemicarbazone (300 mg, 1.27 mmol) prepared above.

$^1$H NMR (270 MHz, CDCl$_3$) δ (ppm): 1.13 (t, J=6.9 Hz, 3H), 1.24 (t, J=7.3 Hz, 3H), 1.96 (s, 3H), 2.20 (m, 1H), 2.24 (s, 3H), 2.71 (m, 2H), 3.14 (m, 1H), 7.13 (br t, J=7.1 Hz, 1H), 7.21-7.26 (m, 2H), 7.51 (br d, J=7.9 Hz, 1H), 8.87 (br s, 1H)

Example 47

Compound 50

Step 1: In a manner similar to that in Step 1 of Example 1, 2'-methoxyacetophenone=thiosemicarbazone (891 mg, 92%) was obtained from 2'-methoxyacetophenone (601 mg, 4.00 mmol) and thiosemicarbazide (366 mg, 4.00 mmol).

Step 2: In a manner similar to that in Step 2 of Example 1, Compound 50 (64.0 mg, 93%) was obtained from 2'-methoxyacetophenone=thiosemicarbazone (50.0 mg, 0.224 mmol) prepared above.

$^1$H NMR (270 MHz, CDCl$_3$) δ (ppm): 2.08 (s, 3H), 2.29 (s, 3H), 2.45 (s, 3H), 3.87 (s, 3H), 6.90 (br t, J=7.3 Hz, 1H), 6.91 (br d, J=7.3 Hz, 1H), 7.06 (br d, J=7.3 Hz, 1H), 7.27 (br t, J=7.3 Hz, 1H), 8.31 (br s, 1H)

Example 48

Compound 51

Step 1: In a manner similar to that in Step 1 of Example 1, 3'-methoxyacetophenone=thiosemicarbazone (713 mg, 58%) was obtained from 3'-methoxyacetophenone (601 mg, 4.00 mmol) and thiosemicarbazide (377 mg, 4.12 mmol).

$^1$H NMR (270 MHz, DMSO-d$_6$) δ (ppm): 2.29 (s, 3H), 3.80 (s, 3H), 6.96 (br d, J=7.9 Hz, 1H), 7.30 (br t, J=7.9 Hz, 1H), 7.44 (br s, 1H), 7.46 (br d, J=7.9 Hz, 1H), 7.94 (br s, 1H), 8.28 (br s, 1H), 10.18 (br s, 1H)

Step 2: In a manner similar to that in Step 2 of Example 1, Compound 51 (419 mg, 71%) was obtained from 3'-methoxyacetophenone=thiosemicarbazone (500 mg, 2.24 mmol) prepared above.

$^1$H NMR (270 MHz, CDCl$_3$) δ (ppm): 2.10 (s, 3H), 2.30 (s, 3H), 2.34 (s, 3H), 3.78 (s, 3H), 6.78 (br d, J=7.9 Hz, 1H), 6.94 (br s, 1H), 7.01 (br d, J=7.9 Hz, 1H), 7.25 (br t, J=7.9 Hz, 1H), 9.48 (br s, 1H)

Example 49

Compound 52

Step 1: In a manner similar to that in Step 1 of Example 1, 4'-methoxyacetophenone=thiosemicarbazone (448 mg, 83%) was obtained from 4'-methoxyacetophenone (362 mg, 2.41 mmol) and thiosemicarbazide (225 mg, 2.46 mmol).

Step 2: In a manner similar to that in Step 2 of Example 1, Compound 52 (248 mg, 90%) was obtained from 4'-methoxyacetophenone=thiosemicarbazone (200 mg, 0.896 mmol) prepared above.

$^1$H NMR (270 MHz, CDCl$_3$) δ (ppm): 2.06 (s, 3H), 2.24 (s, 3H), 2.35 (s, 3H), 3.78 (s, 3H), 6.84 (d, J=8.6 Hz, 2H), 7.36 (d, J=8.6 Hz, 2H), 8.56 (br s, 1H)

Example 50

Compound 53

Step 1: In a manner similar to that in Step 1 of Example 1, 2'-fluoroacetophenone=thiosemicarbazone (704 mg, 83%) was obtained from 2'-fluoroacetophenone (558 mg, 4.04 mmol) and thiosemicarbazide (385 mg, 4.12 mmol).

$^1$H NMR (270 MHz, DMSO-d$_6$) δ (ppm): 2.29 (s, 3H), 7.19-7.28 (m, 2H), 7.40-7.48 (m, 1H), 7.74-7.80 (m, 2H), 8.30 (br s, 1H), 10.34 (br s, 1H)

Step 2: In a manner similar to that in Step 2 of Example 1, Compound 53 (199 mg, 71%) was obtained from 2'-fluoroacetophenone=thiosemicarbazone (200 mg, 0.948 mmol) prepared above.

$^1$H NMR (270 MHz, CDCl$_3$) δ (ppm): 2.05 (s, 3H), 2.26 (s, 3H), 2.40 (s, 3H), 7.01-7.12 (m, 2H), 7.23-7.31 (m, 2H), 8.68 (br s, 1H)

Example 51

Compound 54

Step 1: In a manner similar to that in Step 1 of Example 1, 3'-fluoroacetophenone=thiosemicarbazone (772 mg, 92%) was obtained from 3'-fluoroacetophenone (553 mg, 4.00 mmol) and thiosemicarbazide (372 mg, 4.07 mmol).

$^1$H NMR (270 MHz, DMSO-d$_6$) δ (ppm): 2.29 (s, 3H), 7.17-7.24 (m, 1H), 7.38-7.46 (m, 1H), 7.69 (br d, J=8.9 Hz, 1H), 7.88 (br d, J=11.2 Hz, 1H), 8.09 (br s, 1H), 8.31 (br s, 1H), 10.24 (br s, 1H)

Step 2: In a manner similar to that in Step 2 of Example 1, Compound 54 (242 mg, 74%) was obtained from 3'-fluoroacetophenone=thiosemicarbazone (233 mg, 1.10 mmol) prepared above.

$^1$H NMR (270 MHz, CDCl$_3$) δ (ppm): 2.08 (s, 3H), 2.26 (s, 3H), 2.35 (s, 3H), 6.92-6.99 (m, 1H), 7.07-7.13 (m, 1H), 7.18-7.22 (m, 1H), 7.28-7.34 (m, 1H), 8.54 (br s, 1H)

Example 52

Compound 55

Step 1: In a manner similar to that in Step 1 of Example 1, 4'-fluoroacetophenone=thiosemicarbazone (769 mg, 91%) was obtained from 4'-fluoroacetophenone (553 mg, 4.00 mmol) and thiosemicarbazide (376 mg, 4.11 mmol).

Step 2: In a manner similar to that in Step 2 of Example 1, Compound 55 (251 mg, 86%) was obtained from 4'-fluoroacetophenone=thiosemicarbazone (208 mg, 0.986 mmol) prepared above.

$^1$H NMR (270 MHz, CDCl$_3$) δ (ppm): 2.14 (s, 3H), 2.22 (s, 3H), 2.36 (s, 3H), 6.98-7.05 (m, 2H), 7.38-7.44 (m, 2H), 8.09 (br s, 1H)

Example 53

Compound 56

Step 1: In a manner similar to that in Step 1 of Example 1, 2'-chloroacetophenone=thiosemicarbazone (362 mg, 58%) was obtained from 2'-chloroacetophenone (344 mg, 2.23 mmol) and thiosemicarbazide (194 mg, 2.12 mmol).

Step 2: In a manner similar to that in Step 2 of Example 1, Compound 56 (347 mg, 97%) was obtained from 2'-chloroacetophenone=thiosemicarbazone (200 mg, 1.14 mmol) prepared above.

¹H NMR (270 MHz, CDCl₃) δ (ppm): 1.98 (s, 3H), 2.23 (s, 3H), 2.38 (s, 3H), 7.22-7.27 (m, 2H), 7.37-7.45 (m, 2H), 9.05 (br s, 1H)

Example 54

Compound 57

In a manner similar to that in Example 8, Compound 57 (347 mg, 97%) was obtained from Compound 56 (200 mg, 1.14 mmol) prepared in Example 53.

¹H NMR (270 MHz, CDCl₃) δ (ppm): 1.35 (t, J=6.9 Hz, 3H), 2.25 (s, 3H), 2.30 (s, 3H), 2.40 (s, 3H), 3.91-3.93 (br s, 2H), 7.22-7.28 (m, 2H), 7.38-7.42 (m, 2H)

Example 55

Compound 58

Step 1: In a manner similar to that in Step 1 of Example 1, 3'-chloroacetophenone=thiosemicarbazone (211 mg, 45%) was obtained from 3'-chloroacetophenone (319 mg, 2.06 mmol) and thiosemicarbazide (188 mg, 2.06 mmol).

Step 2: In a manner similar to that in Step 2 of Example 1, Compound 58 (347 mg, 97%) was obtained from 3'-chloroacetophenone=thiosemicarbazone (200 mg, 1.14 mmol) prepared above.

¹H NMR (270 MHz, CDCl₃) δ (ppm): 2.01 (s, 3H), 2.19 (s, 3H), 2.25 (s, 3H), 7.29-7.41 (m, 4H), 11.68 (br s, 1H)

Example 56

Compound 59

Step 1: In a manner similar to that in Step 1 of Example 1, 4'-chloroacetophenone=thiosemicarbazone (362 mg, 58%) was obtained from 4'-chloroacetophenone (344 mg, 2.23 mmol) and thiosemicarbazide (194 mg, 2.06 mmol).

Step 2: In a manner similar to that in Step 2 of Example 1, Compound 59 (193 mg, 86%) was obtained from 4'-chloroacetophenone=thiosemicarbazone (164 mg, 0.720 mmol) prepared above.

¹H NMR (270 MHz, CDCl₃) δ (ppm): 2.11 (s, 3H), 2.23 (s, 3H), 2.24 (s, 3H), 7.30 (d, J=8.6 Hz, 2H), 7.36 (d, J=8.6 Hz, 2H), 8.34 (br s, 1H)

Example 57

Compound 60

Step 1: In a manner similar to that in Step 1 of Example 1, 2'-bromoacetophenone=thiosemicarbazone (392 mg, 69%) was obtained from 2'-bromoacetophenone (415 mg, 2.08 mmol) and thiosemicarbazide (190 mg, 2.08 mmol).

¹H NMR (270 MHz, DMSO-d₆) δ (ppm): 2.28 (s, 3H), 7.29-7.76 (m, 5H), 8.25 (br s, 1H), 10.35 (br s, 1H)

Step 2: In a manner similar to that in Step 2 of Example 1, Compound 60 (328 mg, 99%) was obtained from 2'-bromoacetophenone=thiosemicarbazone (254 mg, 0.933 mmol) prepared above.

¹H NMR (270 MHz, CDCl₃) δ (ppm): 2.01 (s, 3H), 2.23 (s, 3H), 2.38 (s, 3H), 7.13 (br t, J=7.6 Hz, 1H), 7.30 (br t, J=7.6 Hz, 1H), 7.47 (br d, J=7.6 Hz, 1H), 7.62 (br s, J=7.6 Hz, 1H), 8.86 (br s, 1H)

Example 58

Compound 61

Step 1: In a manner similar to that in Step 1 of Example 1, 2'-hydroxyacetophenone=thiosemicarbazone (649 mg, 78%) was obtained from 2'-hydroxyacetophenone (544 mg, 4.00 mmol) and thiosemicarbazide (377 mg, 4.12 mmol).

¹H NMR (270 MHz, DMSO-d₆) δ (ppm): 2.31 (s, 3H), 6.85 (br t, J=7.0 Hz, 1H), 6.88 (br d, J=7.0 Hz, 1H), 7.25 (br t, J=7.0 Hz, 1H), 7.50 (br s, 1H), 7.53 (br d, J=7.0 Hz, 1H), 7.81 (br s, 1H), 8.10 (br s, 1H), 10.35 (br s, 1H)

Step 2: In a manner similar to that in Step 2 of Example 1, Compound 61 (322 mg, 70%) was obtained from 2'-hydroxyacetophenone=thiosemicarbazone (233 mg, 1.10 mmol) prepared above.

¹H NMR (270 MHz, DMSO-d₆) δ (ppm): 2.04 (s, 3H), 2.06 (s, 3H), 2.23 (s, 3H), 2.24 (s, 3H), 7.12 (br d, J=7.6 Hz, 1H), 7.23 (br t, J=7.6 Hz, 1H), 7.35 (br t, J=7.6 Hz, 1H), 7.39 (br d, J=7.6 Hz, 1H), 10.20 (br s, 1H)

Example 59

Compound 62

Step 1: In a manner similar to that in Step 1 of Example 1, 3'-hydroxyacetophenone=thiosemicarbazone (654 mg, 78%) was obtained from 3'-hydroxyacetophenone (546 mg, 4.01 mmol) and thiosemicarbazide (379 mg, 4.15 mmol).

Step 2: In a manner similar to that in Step 2 of Example 1, Compound 62 (351 mg, 84%) was obtained from 3'-hydroxyacetophenone=thiosemicarbazone (262 mg, 1.25 mmol) prepared above.

¹H NMR (270 MHz, DMSO-d₆) δ (ppm): 1.96 (s, 3H), 2.27 (s, 3H), 2.28 (s, 3H), 2.34 (s, 3H), 7.07 (br d, J=8.4 Hz, 1H), 7.15 (br s, 1H), 7.32 (br d, J=8.4 Hz, 1H), 7.33 (br t, J=8.4 Hz, 1H), 9.24 (br s, 1H)

Example 60

Compound 63

Step 1: In a manner similar to that in Step 1 of Example 1, 3'-hydroxybenzaldehyde=thiosemicarbazone (732 mg, 88%) was obtained from 3'-hydroxybenzaldehyde (488 mg, 4.00 mmol) and thiosemicarbazide (378 mg, 4.15 mmol).

¹H NMR (270 MHz, DMSO-d₆) δ (ppm): 6.80 (m, 1H), 7.13 (br s, 1H), 7.19 (m, 2H), 7.87 (br s, 1H), 7.96 (s, 1H), 8.14 (br s, 1H), 9.56 (br s, 1H), 11.35 (br s, 1H)

Step 2: In a manner similar to that in Step 2 of Example 1, Compound 63 (322 mg, 70%) was obtained from 3'-hydroxybenzaldehyde=thiosemicarbazone (300 mg, 1.43 mmol) prepared above.

¹H NMR (270 MHz, DMSO-d₆) δ (ppm): 2.18 (s, 3H), 2.25 (s, 3H), 2.28 (s, 3H), 6.86 (s, 1H), 7.04 (br d, J=7.4 Hz, 1H), 7.05 (s, 1H), 7.19 (br d, J=7.4 Hz, 1H), 7.31 (br t, J=7.4 Hz, 1H), 8.16 (br s, 1H)

Example 61

Compound 64

Step 1: In a manner similar to that in Step 1 of Example 1, 4'-hydroxyacetophenone=thiosemicarbazone (830 mg, 99%)

was obtained from 4'-hydroxyacetophenone (544 mg, 4.00 mmol) and thiosemicarbazide (387 mg, 4.25 mmol).

$^1$H NMR (270 MHz, DMSO-d$_6$) δ (ppm): 2.23 (s, 3H), 6.75 (d, J=8.5 Hz, 2H), 7.76 (d, J=8.5 Hz, 2H), 7.78 (br s, 1H), 8.14 (br s, 1H), 9.75 (s, 1H), 10.05 (s, 1H)

Step 2: In a manner similar to that in Step 2 of Example 1, Compound 64 (199 mg, 61%) was obtained from 4'-hydroxyacetophenone=thiosemicarbazone (202 mg, 0.965 mmol) prepared above.

$^1$H NMR (270 MHz, CDCl$_3$) δ (ppm): 2.15 (s, 3H), 2.22 (s, 3H), 2.23 (s, 3H), 2.29 (s, 3H), 7.07 (br d, J=8.6 Hz, 2H), 7.43 (br d, J=8.6 Hz, 2H), 7.99 (br s, 1H)

Example 62

Compound 65

Step 1: In a manner similar to that in Step 1 of Example 1, 2'-nitroacetophenone=thiosemicarbazone (785 mg, 81%) was obtained from 2'-nitroacetophenone (673 mg, 4.08 mmol) and thiosemicarbazide (365 mg, 3.99 mmol).

$^1$H NMR (270 MHz, DMSO-d$_6$) δ (ppm): 2.27 (s, 3H), 7.32 (br s, 1H), 7.60-7.68 (m, 1H), 7.72-7.79 (m, 2H), 7.96 (br d, J=7.9 Hz, 1H), 8.31 (br s, 1H), 10.52 (br s, 1H)

Step 2: In a manner similar to that in Step 2 of Example 1, Compound 65 (548 mg, 94%) was obtained from 2'-nitroacetophenone=thiosemicarbazone (431 mg, 1.81 mmol) prepared above.

$^1$H NMR (270 MHz, CDCl$_3$) δ (ppm): 2.04 (s, 3H), 2.07 (s, 3H), 2.23 (s, 3H), 7.49-7.71 (m, 4H), 11.73 (br s, 1H)

Example 63

Compound 66

Step 1: In a manner similar to that in Step 1 of Example 1, 3'-nitroacetophenone=thiosemicarbazone (910 mg, 75%) was obtained from 3'-nitroacetophenone (661 mg, 4.00 mmol) and thiosemicarbazide (370 mg, 4.05 mmol).

$^1$H NMR (270 MHz, DMSO-d$_6$) δ (ppm): 2.37 (s, 3H), 7.67 (br t, J=7.9 Hz, 1H), 8.16 (br s, 1H), 8.23 (br d, J=7.9 Hz, 1H), 8.40 (br s, 1H), 8.43 (br s, J=7.9 Hz, 1H), 8.61 (br s, 1H), 10.40 (br s, 1H)

Step 2: In a manner similar to that in Step 2 of Example 1, Compound 66 (409 mg, 60%) was obtained from 3'-nitroacetophenone=thiosemicarbazone (506 mg, 2.12 mmol) prepared above.

$^1$H NMR (270 MHz, CDCl$_3$) δ (ppm): 2.15 (s, 3H), 2.25 (s, 3H), 2.40 (s, 3H), 7.53 (br t, J=8.3 Hz, 1H), 7.73 (br d, J=8.3 Hz, 1H), 8.15 (br d, J=8.3 Hz, 1H), 8.30 (br s, 2H)

Example 64

Compound 67

Step 1: In a manner similar to that in Step 1 of Example 1, 4'-nitroacetophenone=thiosemicarbazone (475 mg, 94%) was obtained from 4'-nitroacetophenone (350 mg, 2.12 mmol) and thiosemicarbazide (195 mg, 2.13 mmol).

Step 2: In a manner similar to that in Step 2 of Example 1, Compound 67 (216 mg, 40%) was obtained from 4'-nitroacetophenone=thiosemicarbazone (397 mg, 1.67 mmol) prepared above.

$^1$H NMR (270 MHz, CDCl$_3$) δ (ppm): 2.15 (s, 3H), 2.24 (s, 3H), 2.38 (s, 3H), 7.59 (d, J=8.6 Hz, 2H), 8.20 (d, J=8.6 Hz, 2H), 8.30 (br s, 1H)

Example 65

Compound 68

Compound 61 (118 mg, 0.352 mmol) prepared in Example 58 was dissolved in methanol (5 mL), and to the solution was added potassium carbonate (200 mg, 1.48 mmol) and the mixture was stirred at room temperature for 10 minutes. The reaction mixture was filtered, and the filtrate was concentrated under reduced pressure. After the residue was dissolved in ethyl acetate, to the solution was added water and 1 mol/L hydrochloric acid, and the mixture was subjected to separation. The organic layer was washed with saturated aqueous sodium chloride and dried over anhydrous sodium sulfate, and then the solvent was evaporated under reduced pressure. The resulting yellow oil was dissolved in methanol (3 mL). To the solution was added diisopropyl ether (10 mL), and the deposited crystals were collected by filtration and dried to obtain Compound 68 (96.9 mg, 94%).

$^1$H NMR (270 MHz, DMSO-d$_6$) δ (ppm): 1.98 (s, 3H), 2.23 (s, 3H), 2.35 (s, 3H), 6.72 (br t, J=7.6 Hz, 1H), 6.83 (br d, J=7.6 Hz, 1H), 6.88 (br d, J=7.6 Hz, 1H), 7.10 (br t, J=7.6 Hz, 1H), 9.95 (br s, 1H), 11.45 (br s, 1H)

Example 66

Compound 69

In a manner similar to that in Example 65, Compound 69 (101 mg, 82%) was obtained from Compound 62 (140 mg, 0.417 mmol) prepared in Example 59.

$^1$H NMR (270 MHz, DMSO-d$_6$) δ (ppm): 2.01 (s, 3H), 2.18 (s, 3H), 2.23 (s, 3H), 6.66 (br t, J=7.9 Hz, 1H), 6.69 (br s, 1H), 6.76 (br d, J=7.9 Hz, 1H), 7.13 (br t, J=7.9 Hz, 1H), 9.46 (br s, 1H), 11.60 (br s, 1H)

Example 67

Compound 70

In a manner similar to that in Example 65, Compound 70 (88 mg, 91%) was obtained from Compound 64 (11.0 mg, 0.328 mmol) prepared in Example 61.

$^1$H NMR (270 MHz, CDCl$_3$) δ (ppm): 2.00 (s, 3H), 2.16 (s, 3H), 2.23 (s, 3H), 6.71 (d, J=8.6 Hz, 2H), 7.15 (d, J=8.6 Hz, 2H), 9.48 (br s, 1H), 11.6 (br s, 1H)

Example 68

Compound 71

Step 1: In a manner similar to that in Step 1 of Example 1, 3'-cyanoacetophenone=thiosemicarbazone (863 mg, 99%) was obtained from 3-acetylbenzonitrile (581 mg, 4.00 mmol) and thiosemicarbazide (370 mg, 4.05 mmol).

Step 2: In a manner similar to that in Step 2 of Example 1, Compound 71 (274 mg, 68%) was obtained from 3'-cyanoacetophenone=thiosemicarbazone (300 mg, 1.34 mmol) prepared above.

$^1$H NMR (270 MHz, CDCl$_3$) δ (ppm): 2.08 (s, 3H), 2.26 (s, 3H), 2.36 (s, 3H), 7.46 (m, 1H), 7.56 (m, 1H), 7.68 (m, 1H), 7.71 (br s, 1H), 8.73 (br s, 1H)

Example 69

Compound 72

Step 1: In a manner similar to that in Step 1 of Example 1, 4'-cyanoacetophenone=thiosemicarbazone (430 mg, 98%)

was obtained from 4-acetylbenzonitrile (290 mg, 2.0 mmol) and thiosemicarbazide (185 mg, 2.02 mmol).

$^1$H NMR (270 MHz, DMSO-$d_6$) δ (ppm): 2.30 (s, 3H), 7.82 (d, J=8.4 Hz, 2H), 8.12 (br s, 1H), 8.14 (d, J=8.4 Hz, 2H), 8.40 (br s, 1H), 10.51 (br s, 1H)

Step 2: In a manner similar to that in Step 2 of Example 1, Compound 72 (494 mg, 94%) was obtained from 4'-cyanoacetophenone=thiosemicarbazone (380 mg, 1.74 mmol).

$^1$H NMR (270 MHz, DMSO-$d_6$) δ (ppm): 2.01 (s, 3H), 2.18 (s, 3H), 2.31 (s, 3H), 7.54 (d, J=11.7 Hz, 2H), 7.81 (d, J=11.7 Hz, 2H), 11.73 (br s, 1H)

Example 70

Compound 73

Step 1: In a manner similar to that in Step 1 of Example 1, 3'-trifluoromethylacetophenone=thiosemicarbazone (888 mg, 63%) was obtained from 3'-trifluoromethylacetophenone (765 mg, 4.07 mmol) and thiosemicarbazide (370 mg, 4.05 mmol).

Step 2: In a manner similar to that in Step 2 of Example 1, Compound 73 (270 mg, 68%) was obtained from 3'-trifluoromethylacetophenone=thiosemicarbazone (300 mg, 1.15 mmol) prepared above.

$^1$H NMR (270 MHz, CDCl$_3$) δ (ppm): 2.01 (s, 3H), 2.27 (s, 3H), 2.37 (s, 3H), 7.43 (br t, J=7.6 Hz, 1H), 7.52 (br d, J=7.6 Hz, 1H), 7.63 (br d, J=7.6 Hz, 1H), 7.65 (br s, 1H), 8.89 (br s, 1H)

Example 71

Compound 74

Step 1: In a manner similar to that in Step 1 of Example 1, 2'-carboxyacetophenone=thiosemicarbazone (489 mg, 52%) was obtained from 2-acetylbenzoic acid (381 mg, 4.17 mmol) and thiosemicarbazide (381 mg, 4.17 mmol).

Step 2: In a manner similar to that in Step 2 of Example 1, Compound 74 (313 mg, 64%) was obtained from 2'-carboxyacetophenone=thiosemicarbazone (363 mg, 1.53 mmol) prepared above.

$^1$H NMR (270 MHz, CDCl$_3$) δ (ppm): 2.04 (s, 3H), 2.29 (s, 3H), 2.38 (s, 3H), 3.20-3.30 (br s, 1H), 7.88-8.15 (m, 3H), 8.32-8.33 (br m, 1H)

Example 72

Compound 75

Step 1: In a manner similar to that in Step 1 of Example 1, 2',6'-dimethoxyacetophenone=thiosemicarbazone (747 mg, 83%) was obtained from 2',6'-dimethoxyacetophenone (606 mg, 3.98 mmol) and thiosemicarbazide (374 mg, 4.09 mmol).

$^1$H NMR (270 MHz, DMSO-$d_6$) δ (ppm): 2.09 (s, 3H), 3.77 (s, 6H), 6.80 (d, J=8.2 Hz, 2H), 7.44 (t, J=8.2 Hz, 1H), 7.83 (br s, 1H), 8.04 (br s, 1H), 8.31 (br s, 1H)

Step 2: In a manner similar to that in Step 2 of Example 1, Compound 75 (441 mg, 89%) was obtained from 2',6'-dimethoxyacetophenone=thiosemicarbazone (363 mg, 1.61 mmol) prepared above.

$^1$H NMR (270 MHz, CDCl$_3$) δ (ppm): 2.02 (s, 3H), 2.21 (s, 3H), 2.51 (s, 3H), 3.78 (s, 6H), 6.53 (d, J=8.5 Hz, 2H), 7.15 (t, J=8.5 Hz, 1H), 8.70 (br s, 1H)

Example 73

Compound 76

Step 1: In a manner similar to that in Step 1 of Example 1, 3',5'-dihydroxyacetophenone=thiosemicarbazone (707 mg, 78%) was obtained from 3',5'-dihydroxyacetophenone (613 mg, 4.03 mmol) and thiosemicarbazide (376 mg, 4.11 mmol).

$^1$H NMR (270 MHz, DMSO-$d_6$) δ (ppm): 2.20 (s, 3H), 6.25 (br s, 1H), 6.69 (br s, 2H), 7.64 (br s, 1H), 8.26 (br s, 1H), 9.29 (br s, 2H), 10.19 (br s, 1H)

Step 2: In a manner similar to that in Step 2 of Example 1, Compound 76 (591 mg, 69%) was obtained from 3',5'-dihydroxyacetophenone=thiosemicarbazone (622 mg, 2.76 mmol) prepared above.

$^1$H NMR (270 MHz, CDCl$_3$) δ (ppm): 2.01 (s, 3H), 2.17 (s, 3H), 2.18 (s, 3H), 6.10 (br s, 1H), 6.16 (br s, 2H), 9.27 (br s, 2H), 11.59 (br s, 1H)

Example 74

Compound 77

Step 1: In a manner similar to that in Step 1 of Example 1, 3',4'-dihydroxyacetophenone=thiosemicarbazone (747 mg, 83%) was obtained from 3',4'-dihydroxyacetophenone (606 mg, 3.98 mmol) and thiosemicarbazide (374 mg, 4.09 mmol).

$^1$H NMR (270 MHz, DMSO-$d_6$) δ (ppm): 2.20 (s, 3H), 6.72 (br d, J=8.3 Hz, 1H), 7.18 (br d, J=8.3 Hz, 1H), 7.29 (br s, 1H), 7.65 (br s, 1H), 8.18 (br s, 2H), 9.09 (br s, 2H), 10.09 (br s, 1H)

Step 2: In a manner similar to that in Step 2 of Example 1, Compound 77 (441 mg, 89%) was obtained from 3',4'-dihydroxyacetophenone=thiosemicarbazone (363 mg, 1.61 mmol) prepared above.

$^1$H NMR (270 MHz, CDCl$_3$) δ (ppm): 2.01 (s, 3H), 2.06 (s, 3H), 2.20 (s, 3H), 6.62 (br t, J=7.6 Hz, 1H), 6.66 (br d, J=8.2 Hz, 1H), 6.71 (br s, 1H), 8.93 (s, 1H), 8.97 (s, 1H), 11.56 (br s, 1H)

Example 75

Compound 78

Step 1: In a manner similar to that in Step 1 of Example 1, 2',4'-dimethylacetophenone=thiosemicarbazone (110 mg, 12%) was obtained from 2',4'-dimethylacetophenone (598 mg, 4.04 mmol) and thiosemicarbazide (366 mg, 4.00 mmol).

Step 2: In a manner similar to that in Step 2 of Example 1, Compound 78 (107 mg, 77%) was obtained from 2',4'-dimethylacetophenone=thiosemicarbazone (100 mg, 0.452 mmol) prepared above.

$^1$H NMR (270 MHz, CDCl$_3$) δ (ppm): 2.16 (s, 3H), 2.21 (s, 3H), 2.35 (s, 3H), 6.92 (d, J=7.9 Hz, 1H), 7.07 (d, J=7.9 Hz, 1H), 8.22 (br s, 1H)

Example 76

Compound 79

Step 1: To a solution of hydrazine monohydrate (1.00 mL, 20.6 mmol) in acetonitrile (5.00 mL) was added allyl isothiocyanate (2.00 mL, 20.4 mmol), and the mixture was stirred at 60° C. for 30 minutes. To the reaction mixture was added diethyl ether (50 mL), and the deposited solid was collected by filtration. The collected solid was dried to obtain 4-allylthiosemicarbazide (1.22 g, 46%).

¹H NMR (270 MHz, DMSO-d₆) δ (ppm): 4.11 (t, J=5.3 Hz, 2H), 4.47 (br s, 2H), 5.03 (d, J=12.3 Hz, 1H), 5.08 (d, J=19.1 Hz, 1H), 5.86 (m, 1H), 7.88 (br s, 1H), 8.70 (br s, 1H)

Step 2: In a manner similar to that in Step 1 of Example 1, acetophenone=4-allylthiosemicarbazone (1.74 g, 80%) was obtained from acetophenone (1.09 mL, 9.34 mmol) and 4-allylthiosemicarbazide (1.22 g, 9.31 mmol) prepared above.

¹H NMR (270 MHz, DMSO-d₆) δ (ppm): 2.31 (s, 3H), 4.25 (t, J=5.8 Hz, 2H), 5.10 (d, J=10.5 Hz, 1H), 5.18 (d, J=17.5 Hz, 1H), 5.91 (m, 1H), 7.37-7.42 (m, 3H), 7.91-7.94 (m, 2H), 8.61 (t, J=6.0 Hz, 1H), 10.3 (br s, 1H)

Step 3: Acetophenone=4-allylthiosemicarbazone (30 mg, 0.11 mmol) prepared above was dissolved in chloroform (0.5 mL), and to the solution was added acetyl chloride (0.17 mL, 2.32 mmol) and pyridine (0.190 mL, 2.31 mmol), and the solution was stirred at room temperature for 5 hours. To the reaction mixture was added 2 mol/L aqueous sodium hydroxide, then the mixture was extracted with ethyl acetate. The organic layer was washed with saturated aqueous ammonium chloride and saturated aqueous sodium chloride, and then dried over anhydrous sodium sulfate, and the solvent was evaporated. The residue was purified by silica gel column chromatography (ethyl acetate/n-hexane=1/2) to obtain Compound 79 (25 mg, 89%).

¹H NMR (270 MHz, CDCl₃) δ (ppm): 2.26 (s, 3H), 2.27 (s, 3H), 2.36 (s, 3H), 4.47-4.53 (m, 2H), 5.24 (d, J=17.3 Hz, 1H), 5.29 (d, J=10.5 Hz, 1H), 5.91 (m, 1H), 7.20-7.45 (m, 5H)

FAB-MS (m/z): 318 (M⁺+1)

Example 77

Compounds 80 and 81

Step 1: In a manner similar to that in Step 3 of Example 76, Compound 80 (42 mg, 5%) was obtained from acetophenone=4-allylthiosemicarbazone (694 mg, 2.97 mmol) prepared in Step 2 of Example 76, isobutyryl chloride (0.63 mL, 5.97 mmol) and pyridine (0.43 mL, 5.26, mmol).

¹H NMR (270 MHz, CDCl₃) δ (ppm): 1.10 (d, J=6.8 Hz, 3H), 1.13 (d, J=6.9 Hz, 3H), 2.39 (s, 3H), 3.25 (quin., J=7.0 Hz, 1H), 3.84-4.00 (m, 3H), 5.19 (d, J=10.2 Hz, 1H), 5.26 (d, J=17.2 Hz, 1H), 5.93 (m, 1H), 7.20-7.49 (m, 5H)

Step 2: In a manner similar to that in Example 15, Compound 81 (527 mg, 74%) was obtained from Compound 80 (623 mg, 2.05 mmol) prepared above, acetyl chloride (0.59 mL, 8.30 mmol) and pyridine (0.77 mL, 8.28 mmol).

¹H NMR (270 MHz, CDCl₃) δ (ppm): 1.10 (d, J=6.9 Hz, 3H), 1.12 (d, J=6.9 Hz, 3H), 2.27 (s, 3H), 2.34 (s, 3H), 3.21 (quin., J=6.9 Hz, 1H), 4.51 (br s, 2H), 5.25 (d, J=17.2 Hz, 1H), 5.30 (d, J=10.7 Hz, 1H), 5.93 (m, 1H), 7.20-7.42 (m, 5H)

AP-MS (m/z): 346 (M⁺+1)

Example 78

Compound 82

In a manner similar to that in Step 3 of Example 76, Compound 82 (269 mg, 47%) was obtained from acetophenone=thiosemicarbazone (306 mg, 1.59 mmol) prepared in Step 1 of Example 1, pivaloyl chloride (0.40 mL, 3.21 mmol) and pyridine (0.26 mL, 3.22 mmol).

¹H NMR (270 MHz, CDCl₃) δ (ppm): 1.29 (s, 9H), 1.30 (s, 9H), 2.35 (s, 3H), 7.20-7.46 (m, 5H), 7.90 (m, 1H)

AP-MS (m/z): 360 (M⁺−1)

Example 79

Compounds 83 and 84

Step 1: In a manner similar to that in Example 12, Compound 83 (537 mg, 67%) was obtained from Compound 21 (1.00 g, 2.88 mmol) prepared in Example 18.

¹H NMR (270 MHz, CDCl₃) δ (ppm): 1.12 (d, J=6.9 Hz, 3H), 1.14 (d, J=6.9 Hz, 3H), 2.39 (s, 3H), 2.91 (d, J=4.9 Hz, 3H), 3.30 (m, 1H), 3.90 (br, 1H), 7.20-7.43 (m, 5H)

Step 2: In a manner similar to that in Example 15, Compound 84 (233 mg, 38%) was obtained from Compound 83 (536 mg, 1.93 mmol) prepared above, acetyl chloride (0.28 mL, 3.87 mmol) and pyridine (0.32 mL, 3.90 mmol).

¹H NMR (270 MHz, CDCl₃) δ (ppm): 1.12 (d, J=6.9 Hz, 3H), 1.14 (d, J=6.9 Hz, 3H), 2.28 (s, 3H), 2.34 (s, 3H), 3.28 (quin., J=6.9 Hz, 1H), 3.46 (br s, 3H), 7.20-7.43 (m, 5H)

FAB-MS (m/z): 320 (M⁺+1)

Elemental analysis (C₁₆H₂₁N₃O₂S): Found (%) C; 60.16, H; 6.63, N; 13.15, Calcd. (%) C, 60.27; H, 6.73; N, 13.20;

Example 80

Compound 85

In a manner similar to that in Step 2 of Example 1, Compound 85 (176 mg, 20%) was obtained from acetophenone=thiosemicarbazone (517 mg, 2.68 mmol) prepared in Step 1 of Example 1 and isobutyric anhydride (2.22 mL, 13.4 mmol).

¹H NMR (270 MHz, CDCl₃) δ ppm): 1.09 (d, J=2.6 Hz, 3H), 1.12 (d, J=2.6 Hz, 3H), 1.21 (d, J=2.6 Hz, 3H), 1.23 (d, J=2.6 Hz, 3H), 2.37 (s, 3H), 2.50 (quin., J=6.9 Hz, 1H), 3.20 (quin., J=6.9 Hz, 1H), 7.20-7.48 (m, 5H), 7.98 (br s, 1H)

AP-MS (m/z): 334 (M⁺+1)

Elemental analysis (C₁₇H₂₈N₈O₂S): Found (%) C; 61.23, H; 6.95, N; 12.60, Calcd. (%) C, 61.22; H, 6.93; N, 12.63;

Example 81

Compounds 86 and 87

Step 1: In a manner similar to that in Example 11, Compound 86 (588 mg, 43%) was obtained from acetophenone=thiosemicarbazone (1.01 g, 5.22 mmol) prepared in Step 1 of Example 1, isobutyric anhydride (1.73 mL, 10.4 mmol) and pyridine (0.84 mL, 10.4 mmol).

¹H NMR (270 MHz, CDCl₃) δ (ppm): 1.09 (d, J=6.9 Hz, 3H), 1.11 (d, J=6.9 Hz, 3H), 2.40 (s, 3H), 3.21 (quin., J=6.9 Hz, 1H), 4.12 (br s, 2H), 7.20-7.40 (m, 5H)

Step 2: In a manner similar to that in Example 15, Compound 87 (47 mg, 16%) was obtained from Compound 86 (256 mg, 0.97 mmol) prepared above and acetic anhydride (0.46 mL, 4.88 mmol).

¹H NMR (270 MHz, CDCl₃) δ (ppm): 1.19 (d, J=6.9 Hz, 3H), 1.20 (d, J=6.9 Hz, 3H), 2.25 (s, 3H), 2.38 (s, 3H), 2.47 (quin., J=6.9 Hz, 1H), 7.20-7.50 (m, 5H)

Example 82

Compound 88

In a manner similar to that in Example 15, Compound 88 (53 mg, 8%) was obtained from Compound 14 (502 mg, 2.14 mmol) prepared in Example 11 and isobutyric anhydride (1.77 mL, 10.7 mmol).

¹H NMR (270 MHz, CDCl₃) δ (ppm): 1.20 (d, J=6.9 Hz, 3H), 1.22 (d, J=6.9 Hz, 3H), 2.24 (s, 3H), 2.38 (s, 3H), 2.48 (quin., J=6.9 Hz, 1H), 7.20-7.46 (m, 5H), 8.08 (br s, 1H)

AP-MS (m/z): 306 (M⁺+1)

Example 83

Compound 89

In a manner similar to that in Example 15, Compound 89 (274 mg, 64%) was obtained from Compound 14 (303 mg, 1.29 mmol) prepared in Example 11, cyclopentanecarbonyl chloride (0.32 mL, 2.59 mmol) and pyridine (0.21 mL, 2.60 mmol).

¹H NMR (270 MHz, CDCl₃) δ (ppm): 1.50-1.95 (m, 8H), 2.24 (s, 3H), 2.38 (s, 3H), 2.65 (quin., J=7.9 Hz, 1H), 7.20-7.45 (m, 5H), 8.04 (br s, 1H)

AP-MS (m/z): 330 (M⁺−1)

Elemental analysis (C₁₇H₂₁N₃O₂S.0.4H₂O): Found (%) C, 60.30; H, 6.49; N, 12.41; Calcd. (%) C, 60.45; H, 6.49; N, 12.05;

Example 84

Compounds 90 and 91

Step 1: In a manner similar to that in Example 11, Compound 90 (123 mg, 13%) was obtained from acetophenone=thiosemicarbazone (507 mg, 2.63 mmol) prepared in Step 1 of Example 1, isovaleric anhydride (1.05 mL, 5.30 mmol) and pyridine (0.43 mL, 5.26 mmol).

¹H NMR (270 MHz, CDCl₃) δ (ppm): 0.82-1.00 (m, 6H), 2.12 (quin., J=6.6 Hz, 1H), 2.38 (s, 3H), 2.45 (d, J=7.7 Hz, 2H), 4.34 (br, 2H), 7.20-7.48 (m, 5H)

Step 2: In a manner similar to that in Example 15, Compound 91 (128 mg, 98%) was obtained from Compound 91 (105 mg, 0.38 mmol) prepared above, isobutyryl chloride (0.08 mL, 0.76 mmol) and pyridine (0.06 mL, 0.80 mmol).

¹H NMR (270 MHz, CDCl₃) δ (ppm): 0.92 (d, J=6.6 Hz, 1H), 0.93 (d, J=6.6 Hz, 1H), 1.18 (d, J=3.3 Hz, 1H), 1.21 (d, J=3.3 Hz, 1H), 2.13 (quin., J=6.6 Hz, 1H), 2.38 (s, 3H), 2.39-2.56 (m, 4H), 7.20-7.48 (m, 5H), 8.15 (br s, 1H)

Example 85

Compound 92

Step 1: To a solution of acetophenone (4.00 mL, 34.3 mmol) in ethanol (15 mL) was added hydrazine monohydrate (6.67 mL, 138 mmol), and the mixture was heated under reflux for 4 hours. After cooling, to the mixture was added water, and the mixture was extracted with ethyl acetate. The organic layer was washed with saturated aqueous sodium chloride, and then dried over anhydrous sodium sulfate, and the solvent was evaporated. The residue was purified by silica gel column chromatography (ethyl acetate/n-hexane=1/2) to obtain acetophenone=hydrazone (5.39 g, ~100%).

¹H NMR (300 MHz, CDCl₃) δ (ppm): 2.00 (s, 3H), 5.34 (br s, 2H), 7.22-7.60 (m, 5H)

¹³C NMR (300 MHz, CDCl₃) δ (ppm): 11.3, 125.1, 127.7, 127.9, 139.1, 146.7

Step 2: To a solution of ammonium thiocyanate (3.40 g, 44.6 mmol) in acetone (20 mL) was added acetyl chloride (2.80 mL, 37.1 mmol), and the mixture was stirred at 70° C. for 10 minutes. To the reaction mixture was added acetophenone=hydrazone (5.36 g, 40.0 mmol) prepared above, and the mixture was heated under reflux for 20 minutes. After the reaction mixture was cooled, saturated aqueous ammonium chloride was added to the mixture, and the mixture was extracted with chloroform. The organic layer was washed with saturated aqueous sodium chloride, and then dried over anhydrous sodium sulfate, and the solvent was evaporated. The residue was purified by silica gel column chromatography (ethyl acetate/n-hexane=1/2) to obtain acetophenone=4-acetylthiosemicarbazone (148 mg, 2%).

¹H NMR (300 MHz, DMSO-d₆) δ (ppm): 2.15 (s, 3H), 2.28 (s, 3H), 7.47-7.51 (m, 3H), 7.56-7.59 (m, 2H), 11.6 (br s, 1H), 13.6 (br s, 1H)

Step 3: In a manner similar to that in Step 3 of Example 76, Compound 92 (36 mg, 88%) was obtained from acetophenone=4-acetylthiosemicarbazone (30 mg, 0.13 mmol) prepared above, pivaloyl chloride (32 μL, 0.26 mmol) and pyridine (20 μL, 0.26 mmol).

¹H NMR (300 MHz, CDCl₃) δ (ppm): 1.27 (s, 9H), 2.25 (s, 3H), 2.38 (s, 3H), 7.23-7.46 (m, 6H), 8.13 (br s, 1H)

¹³C NMR (300 MHz, CDCl₃) δ (ppm): 24.0, 27.2, 39.4, 80.5, 125.1, 128.0, 128.6, 143.0, 143.1, 169.0, 176.7

AP-MS (m/z): 318 (M⁺+1)

Example 86

Compound 93

In a manner similar to that in Step 2 of Example 1, Compound 93 (123 mg, 45%) was obtained from Compound 14 (201 mg, 0.853 mmol) prepared in Example 11 and pivaloyl chloride (0.21 mL, 1.71 mmol).

¹H NMR (270 MHz, CDCl₃) δ (ppm): 1.26 (s, 9H), 2.24 (s, 3H), 2.38 (s, 3H), 7.20-7.51 (m, 5H), 8.10 (br s, 1H)

AP-MS (m/z): 319 (M⁺+1)

Example 87

Compound 94

Step 1: In a manner similar to that in Step 1 of Example 1, propiophenone=thiosemicarbazone (759 mg, 88%) was obtained from propiophenone (382 mg, 4.18 mmol) and thiosemicarbazide (541 mg, 3.92 mmol).

Step 2: In a manner similar to that in Step 3 of Example 76, Compound 94 (270 mg, 58%) was obtained from propiophenone=thiosemicarbazone (256 mg, 1.24 mmol) prepared above, pivaloyl chloride (597 μL, 4.84 mmol) and pyridine (391 μL, 4.84 mmol).

¹H NMR (270 MHz, CDCl₃) δ (ppm): 1.15 (dd, J=7.1, 7.3 Hz, 3H), 1.29 (s, 9H), 1.34 (s, 9H), 2.29 (qd, J=7.3, 14.6 Hz, 1H), 3.10 (qd, J=7.1, 14.6 Hz, 1H), 7.21-7.40 (m, 5H), 8.31 (br s, 1H)

AP-MS (m/z): 377 (M⁺+1)

Example 88

Compound 95

Step 1: 2-Aminoacetophenone hydrochloride (6.10 g, 35.5 mmol) was dissolved in dichloromethane (60 mL), and to the solution was added triethylamine (7.56 g, 74.9 mmol). The solution was cooled to 0° C., and to the solution was added methanesulfonyl chloride (2.84 mL, 36.5 mmol). The solution was stirred at the same temperature for 5 minutes, and then at room temperature for 2 hours. To the reaction mixture was added water and 1 mol/L hydrochloric acid, and the mixture was extracted with chloroform. After the organic layer was dried over anhydrous sodium sulfate, the solvent was evaporated under reduced pressure. The residue was suspended in chloroform (5 mL) and the suspension was stirred, and then, the resulted crystals were collected by filtration to obtain 2-(methylsulfonylamino)acetophenone (4.58 g, 57%).

Step 2: In a manner similar to that in Step 1 of Example 1, 2-(methylsulfonylamino)acetophenone=thiosemicarbazone (3.08 g, 51%) was obtained from 2-(methylsulfonylamino) acetophenone (4.58 g, 20.2 mmol) prepared above and thiosemicarbazide (1.84 g, 20.2 mmol).

Step 3: In a manner similar to that in Step 3 of Example 76, Compound 95 (1.81 g, 91%) was obtained from 2-(methylsulfonylamino)acetophenone=thiosemicarbazone (1.31 g, 4.36 mmol) prepared above, pivaloyl chloride (2.10 g, 17.4 mmol) and pyridine (1.38 g, 17.4 mmol).

$^1$H NMR (270 MHz, CDCl$_3$) δ (ppm): 1.30 (s, 9H), 1.36 (s, 9H), 2.97 (s, 3H), 3.98 (dd, J=5.3, 13.8 Hz, 1H), 4.64 (dd, J=8.5, 13.8 Hz, 1H), 5.10 (br dd, J=5.3, 8.5 Hz, 1H), 7.25-7.39 (m, 5H), 7.93 (br s, 1H)

AP-MS (m/z): 453 (M$^+$−1)

Example 89

Compound 96

Step 1: In a manner similar to that in Step 1 of Example 1, 2-methylsulfonylamino)acetophenone=4-methylthiosemicarbazone (122 mg) was obtained from 2-(methylsulfonylamino)acetophenone (209 mg, 0.98 mmol) prepared in Step 1 of Example 88 and 4-methylthiosemicarbazide (106 mg, 1.00 mmol).

Step 2: In a manner similar to that in Step 3 of Example 76, Compound 96 (68 mg, 15%) was obtained from 2-(methylsulfonylamino)acetophenone=4-methylthiosemicarbazone (122 mg, 0.41 mmol) obtained above, pivaloyl chloride (128 µL, 1.04 mmol) and pyridine (80 µL, 1.04 mmol).

$^1$H NMR (300 MHz, DMSO-d$_6$) δ (ppm): 1.27 (s, 3H), 1.28 (s, 3H), 2.95 (s, 3H), 3.53 (s, 3H), 3.94 (dd, J=13.9, 6.4 Hz, 1H), 4.27 (dd, J=13.9, 7.9 Hz, 1H), 7.11 (t, J=7.2 Hz, 1H), 7.21-7.38 (m, 5H)

AP-MS (m/z): 467 (M$^+$−1)

Example 90

Compound 97

Step 1: In a manner similar to that in Step 1 of Example 88, 2-(ethylsulfonylamino)acetophenone (367 mg, 39%) was obtained from 2-aminoacetophenone hydrochloride (714 mg, 4.16 mmol), triethylamine (1.45 mL, 10.4 mmol) and ethanesulfonyl chloride (0.434 mL, 4.58 mmol).

Step 2: In a manner similar to that in Step 1 of Example 1, 2-(ethylsulfonylamino)acetophenone=thiosemicarbazone (327 mg, 43%) was obtained from 2-(ethylsulfonylamino) acetophenone (367 mg, 1.61 mmol) prepared above and thiosemicarbazide (147 mg, 1.61 mmol).

Step 3: In a manner similar to that in Step 2 of Example 1, Compound 97 (39 mg, 25%) was obtained from 2-(ethylsulfonylamino)acetophenone=thiosemicarbazone (99 mg, 0.330 mmol), pivaloyl chloride (162 µL, 1.32 mmol) and pyridine (130 µL, 1.58 mmol).

$^1$H NMR (270 MHz, CDCl$_3$) δ (ppm): 1.26 (s, 9H), 1.28 (t, J=7.8 Hz, 3H), 1.29 (8, 9H), 3.09 (m, 2H), 3.97 (dd, J=5.1, 13.5 Hz, 1H), 4.60 (dd, J=8.1, 13.5 Hz, 1H), 4.99 (br dd, J=5.1, 8.1 Hz, 1H), 7.25-7.38 (br s, 5H), 7.93 (br s, 1H)

Example 91

Compound 98

Step 1: In a manner similar to that in Step 1 of Example 1, 2-methoxyacetophenone=thiosemicarbazone (367 mg, 62%) was obtained from 2-methoxyacetophenone (288 mg, 1.92 mmol) and thiosemicarbazide (179 mg, 1.96 mmol).

Step 2: In a manner similar to that in Step 2 of Example 1, Compound 98 (132 mg, 59%) was obtained from 2-methoxyacetophenone=thiosemicarbazone (128 mg, 0.573 mmol) prepared above, pivaloyl chloride (211 µL, 1.72 mmol) and pyridine (152 µL, 1.88 mmol).

$^1$H NMR (270 MHz, CDCl$_3$) δ (ppm): 1.28 (s, 9H), 1.32 (s, 9H), 3.51 (s, 3H), 4.36 (d, J=9.6 Hz, 1H), 4.48 (d, J=9.6 Hz, 1H), 7.24-7.38 (m, 5H), 7.88 (s, 1H)

AP-MS (m/z): 392 (M$^+$+1)

Example 92

Compound 99

Step 1: Methane sulfonamide (0.476 g, 5.00 mmol) was dissolved in N,N-dimethylformamide (10 mL), and to the solution was added 60% sodium hydride (0.275 g, 5.00 mmol) and the mixture was stirred in a water bath for 20 minutes. To the reaction mixture was added 3-chloropropiophenone (843 mg, 5.00 mol). The mixture was stirred in a water bath for one hour, and further stirred at room temperature for 15 hours. To the reaction mixture was added water, and the mixture was extracted with ethyl acetate. The organic layer was washed with saturated aqueous sodium chloride and dried over anhydrous sodium sulfate, and then the solvent was evaporated under reduced pressure. The residue was purified by silica gel column chromatography (chloroform/methanol=20/1) to obtain 3-(methylsulfonylamino)propiophenone (240 mg, 21%).

Step 2: In a manner similar to that in Step 1 of Example 1, 3-(methylsulfonylamino) propiophenone=thiosemicarbazone (219 mg, 45%) was obtained from 3-(methylsulfonylamino)propiophenone (388 mg, 1.71 mmol) prepared above and thiosemicarbazide (156 mg, 1.71 mmol).

Step 3: In a manner similar to that in Step 2 of Example 1, Compound 99 (218 mg, 86%) was obtained from 3-(methylsulfonylamino)propiophenone=thiosemicarbazone (200 mg, 0.696 mmol) obtained above, pivaloyl chloride (342 µL, 2.78 mmol) and pyridine (219 µL, 2.78 mmol).

$^1$H NMR (300 MHz, CDCl$_3$) δ (ppm): 1.30 (s, 9H), 1.34 (s, 9H), 2.56-2.65 (m, 1H), 2.94 (s, 3H), 3.21-3.44 (m, 2H), 3.58-3.70 (m, 1H), 4.45 (br s, 1H), 7.28-7.37 (m, 5H), 7.97 (br s, 1H)

AP-MS (m/z): 467 (M$^-$−1)

Example 93

Compound 100

In a manner similar to that in Step 3 of Example 76, an oily compound was obtained from 3-(methylsulfonylamino) propiophenone=thiosemicarbazone (173 mg, 0.604 mmol) prepared in Step 2 of Example 92, isobutyryl chloride (316 µL 3.02 mmol) and pyridine (292 µL, 3.62 mmol). The oily compound was dissolved in methanol (10 mL). To the solution was added potassium carbonate (1.00 g, 7.24 mmol), and the mixture was vigorously stirred for 1 hour. The reaction mixture was filtered, and the filtrate was concentrated. And then, to the concentrate was added chloroform, water and 1.0 mol/L hydrochloric acid, and the solution was extracted with chloroform. The organic layer was washed with saturated aqueous sodium chloride, and dried over anhydrous sodium sulfate. The solvent was evaporated under reduced pressure, and the residue was purified by preparative thin layer chromatography (chloroform/methanol=20/1) to obtain Compound 100 (111 mg, 41%).

$^1$H NMR (270 MHz, DMSO-$d_6$) δ (ppm): 0.99-1.07 (m, 12H), 2.55-2.66 (m, 2H), 2.80-3.00 (m, 1H), 2.89 (s, 3H), 3.05-3.17 (m, 1H), 3.24-3.38 (m, 2H), 7.16 (br t, J=5.9 Hz, 1H), 7.24-7.39 (m, 5H), 11.6 (br s, 1H)

Example 94

Compound 101

Step 1: In a manner similar to that in Step 1 of Example 88, 2-(trifluoroacetylamino)acetophenone (4.38 g, 59%) was obtained from 2-aminoacetophenone hydrochloride (5.47 g, 31.9 mmol), triethylamine (11.1 mL, 80.0 mmol) and trifluoroacetic anhydride (4.96 mL, 35.1 mmol).

Step 2: In a manner similar to that in Step 1 of Example 1, 2-(trifluoroacetylamino)acetophenone=thiosemicarbazone was obtained from 2-(trifluoroacetylamino)acetophenone (3.00 g, 13.0 mmol) prepared above and thiosemicarbazide (1.18 g, 13.0 mmol).

Step 3: In a manner similar to that in Step 3 of Example 76, Compound 101 (1.72 g, 28%) was obtained from 2-(trifluoroacetylamino)acetophenone=thiosemicarbazone prepared above, pivaloyl chloride (50 mmol, 6.16 mL) and pyridine (60.0 mmol, 4.85 mL).

$^1$H NMR (270 MHz, CDCl$_3$) δ (ppm): 1.27 (s, 9H), 1.38 (s, 9H), 3.95 (dd, J=3.0, 13.5 Hz, 1H), 4.89 (dd, J=3.7, 13.5 Hz, 1H), 7.15 (br d, J=7.3 Hz, 2H), 7.30-7.40 (m, 3H), 7.92 (br s, 1H), 8.27 (br s, 1H)

AP-MS (m/z): 471 (M$^-$−1)

Example 95

Compound 102

In a manner similar to that in Step 3 of Example 76, Compound 102 (64.6 mg, 39%) was obtained from 2-methylsulfonylamino)acetophenone=thiosemicarbazone (100 mg, 0.333 mmol) prepared in Step 2 of Example 88, isobutyryl chloride (140 µL, 1.33 mmol) and pyridine (108 µL, 1.33 mmol).

$^1$H NMR (270 MHz, CDCl$_3$) δ (ppm): 1.17 (d, J=6.9 Hz, 3H), 1.19 (d, J=6.9 Hz, 3H), 1.25 (d, J=6.9 Hz, 6H), 1.29 (d, J=6.9 Hz, 6H), 3.05 (s, 3H), 3.10-3.30 (m, 3H), 4.01 (dd, J=4.8, 14.2 Hz, 1H), 4.74 (dd, J=7.8, 14.2 Hz, 1H), 5.37 (br s, 1H), 7.26-7.40 (m, 5H)

Example 96

Compound 103

Compound 102 (40.0 mg, 0.0805 mg) prepared in Example 95 was dissolved in methanol (10 mL). To the solution was added potassium carbonate (1.00 g, 7.24 mmol), and the mixture was vigorously stirred for 1 hour. The reaction mixture was filtered, and the filtrate was concentrated. Then, to the residue was added chloroform, 1 mol/L hydrochloric acid and water, and the mixture was extracted with chloroform. The organic layer was washed with saturated aqueous sodium chloride, and dried over anhydrous sodium sulfate. The solvent was evaporated under reduced pressure, and the residue was purified by preparative thin layer chromatography (chloroform/methanol=20/1) to obtain Compound 103 (24.2 mg, 84%).

$^1$H NMR (270 MHz, CDCl$_3$) δ (ppm): 1.13 (d, J=6.9 Hz, 3H), 1.18 (d, J=6.9 Hz, 3H), 1.21 (d, J=6.9 Hz, 3H), 1.23 (d, J=6.9 Hz, 3H), 2.50 (m, 1H), 2.90 (s, 3H), 3.27 (m, 1H), 3.98 (dd, J=5.0, 13.9 Hz, 1H), 4.60 (dd, J=8.2, 13.9 Hz, 1H), 5.35 (br dd, J=5.0, 8.2 Hz, 1H), 7.26-7.40 (m, 5H), 8.02 (br s, 1H)

Example 97

Compound 104

Step 1: In a manner similar to that in Step 1 of Example 1, 3-(dimethylamino)propiophenone=thiosemicarbazone (491 mg, 46%) was obtained from 3-(dimethylamino)propiophenone (910 mg, 4.26 mmol) and thiosemicarbazide (387 mg, 4.25 mmol).

Step 2: In a manner similar to that in Step 3 of Example 76, Compound 104 (116 mg, 33%) was obtained from 3-(dimethylamino)propiophenone=thiosemicarbazone (210 mg, 0.839 mmol) prepared above, pivaloyl chloride (496 µL, 3.78 mmol) and pyridine (326 µL, 3.78 mmol).

$^1$H NMR (270 MHz, CDCl$_3$) δ (ppm): 1.29 (s, 9H), 1.31 (s, 9H), 2.23-2.29 (m, 1H), 2.26 (br s, 3H), 2.27 (br s, 3H), 2.46 (ddd, J=8.8, 4.3, 11.3 Hz, 1H), 2.87 (m, 1H), 3.31 (m, 1H), 7.20-7.36 (m, 5H), 7.90 (br s, 1H)

Example 98

Compound 105

Step 1: In a manner similar to that in Step 2 of Example 1, 3-carbomethoxypropiophenone=thiosemicarbazone (10.6 g, 94%) was obtained from 3-carbomethoxypropiophenone (8.13 g, 42.3 mmol) and thiosemicarbazide (3.86 g, 42.3 mmol).

Step 2: In a manner similar to that in Step 3 of Example 76, Compound 105 (9.70 g, 77%) was obtained from 3-carbomethoxypropiophenone=thiosemicarbazone (7.76 g, 29.2 mmol) prepared above, pivaloyl chloride (14.4 mL, 117 mmol) and pyridine (11.3 mL, 140 mmol).

$^1$H NMR (270 MHz, CDCl$_3$) δ (ppm): 1.29 (s, 9H), 1.32 (s, 9H), 2.37 (m, 1H), 2.67 (m, 1H), 2.79 (m, 1H), 3.42 (m, 1H), 3.70 (s, 3H), 7.22-7.40 (m, 5H), 7.89 (br s, 1H)

Example 99

Compound 106

Sodium hydroxide (2.7 g, 67 mmol) was dissolved in water (23 mL). Subsequently, to the solution was added methanol (30 mL) and the solution was stirred. To the solution was added Compound 105 (9.65 g, 22.3 mmol) prepared in Example 98, and the mixture was stirred at room temperature for 5 hours. To the reaction mixture was added 1 mol/L hydrochloric acid (20 mL) and water (30 mL), and the deposited white crystals were collected by filtration. The resulting crystals were washed with water and diisopropyl ether, and then, dried under reduced pressure to obtain Compound 106 (8.92 g, 96%).

$^1$H NMR (270 MHz, CDCl$_3$) δ (ppm): 1.30 (s, 9H), 1.33 (s, 9H), 2.00-2.51 (br s, 1H), 2.44 (m, 1H), 2.66 (m, 1H), 2.88 (m, 1H), 3.44 (m, 1H), 7.23-7.40 (m, 5H), 7.92 (br s, 1H)

Example 100

Compound 107

Compound 106 (1.21 g, 2.88 mmol) prepared in Example 99 was cooled to 0° C. Oxalyl chloride (5 mL) was added to the compound, and the solution was allowed to react at 0° C. for 1 hour. The solvent was evaporated under reduced pressure, and the residue was dried in vacuo. To the residue was added tetrahydrofuran, and the mixture was stirred at 0° C. Then, to the reaction mixture was added 4 mol/L ammonia-methanol solution (5 mL, 20 mmol), and the mixture was stirred at room temperature for 3 hours. To the reaction mixture was added 1 mol/L hydrochloric acid (20 mL) and water (30 mL), and extracted with chloroform. The organic layer was washed with saturated aqueous sodium chloride, and dried over anhydrous sodium sulfate. After the solvent was evaporated under reduced pressure, to the resulting residue was added diisopropyl ether, and then the deposited white crystals were collected by filtration. The resulting crystals were washed with water and diisopropyl ether, and then dried under reduced pressure to obtain Compound 107 (8.92 g, 96%).

$^1$H NMR (270 MHz, DMSO-$d_6$) δ (ppm): 1.17 (s, 9H), 1.28 (s, 9H), 1.81-2.03 (m, 1H), 2.15-2.30 (m, 1H), 2.49-2.75 (m, 1H), 2.95-3.20 (m, 1H), 6.80 (br s, 1H), 7.20-7.41 (m, 5H), 10.93 (br s, 2H)

Example 101

Compound 108

In a manner similar to that in Example 100, Compound 108 (65 mg, 60%) was obtained from Compound 106 (0.104 g, 0.248 mmol) prepared in Example 99, oxalyl chloride (5 mL), hydroxylamine hydrochloride (0.017 g, 0.245 mmol) and triethylamine (0.062 g, 0.614 mmol).

APCl-MS (m/z): 433 (M$^-$−1)

Example 102

Compound 109

In a manner similar to that in Example 100, Compound 109 (1.08 g, 87%) was obtained from Compound 106 (1.20 g, 2.86 mmol) prepared in Example 99, oxalyl chloride (5 mL) and 4 mol/L methylamine-methanol solution (10 mL, 40 mmol).

AP-MS (m/z): 431 (M$^-$−1)

Example 103

Compound 110

Step 1: In a manner similar to that in Step 1 of Example 1, 3-(dimethylaminocarbonyl)propiophenone=thiosemicarbazone (3.67 g, 79%) was obtained from 3-(dimethylaminocarbonyl)propiophenone (4.00 g, 18.7 mmol) and thiosemicarbazide (1.70 g, 18.7 mmol).

Step 2: In a manner similar to that in Step 3 of Example 76, Compound 110 (1.64 g, 49%) was obtained from 3-(dimethylaminocarbonyl)propiophenone=thiosemicarbazone (2.00 g, 7.99 mmol) prepared above, pivaloyl chloride (3.94 mL, 32.0 mmol) and pyridine (3.11 mL, 38.4 mmol).

AP-MS (m/z): 447 (M$^+$+1)

Example 104

Compound 111

In a manner similar to that in Example 100, Compound 111 (480 mg, 84%) was obtained from Compound 106 (51.8 mg, 0.124 mmol) prepared in Example 99, oxalyl chloride (0.5 mL), ethanolamine (7.58 mg, 0.248 mmol) and triethylamine (18.8 mg, 0.186 mmol).

$^1$H NMR (270 MHz, CDCl$_3$) δ (ppm): 1.29 (s, 9H), 1.33 (s, 9H), 2.16-2.25 (m, 1H), 2.65-2.79 (m, 2H), 3.33-3.44 (m, 3H), 3.72 (m, 2H), 6.18 (br s, 1H), 7.22-7.35 (m, 6H), 8.01 (br s, 1H)

Example 105

Compound 112

In a manner similar to that in Example 100, Compound 112 (400 mg, 68%) was obtained from Compound 106 (51.8 mg, 0.124 mmol) prepared in Example 99, oxalyl chloride (0.5 mL), n-butylamine (18.14 mg, 0.248 mmol) and triethylamine (18.8 mg, 0.186 mmol).

$^1$H NMR (300 MHz, CDCl$_3$) δ (ppm): 0.92 (t, J=7.1 Hz, 3H), 1.25-1.60 (m, 4H), 1.29 (s, 9H), 1.33 (s, 9H), 2.16 (m, 1H), 2.69 (m, 2H), 3.25 (m, 2H), 3.67 (m, 1H), 5.62 (br s, 1H), 7.23-7.34 (m, 5H), 7.94 (br s, 1H)

Example 106

Compound 1132

In a manner similar to that in Example 100, Compound 113 (50 mg, 81%) was obtained from Compound 106 (51.8 mg, 0.124 mmol) prepared in Example 99, oxalyl chloride (0.5 mL), cyclohexylamine (24.6 mg, 0.248 mmol) and triethylamine (18.8 mg, 0.186 mmol).

$^1$H NMR (270 MHz, CDCl$_3$) δ (ppm): 1.05-1.50 (m, 6H), 1.28 (s, 9H), 1.33 (s, 9H), 1.65-1.80 (m, 2H), 1.85-1.95 (m, 2H), 2.14 (m, 1H), 2.65 (m, 2H), 3.37 (m, 1H), 3.38 (m, 1H), 5.50 (br s, 1H), 7.10-7.38 (m, 5H), 7.93 (br s, 1H)

Example 107

Compound 114

Step 1: In a manner similar to that in Step 1 of Example 1, 4-carbomethoxybutyrophenone=thiosemicarbazone (0.700 g, 88%) was obtained from 4-carbomethoxybutyrophenone (0.588 g, 2.85 mmol) and thiosemicarbazide (0.260 g, 2.85 mmol).

Step 2: In a manner similar to that in Step 3 of Example 76, Compound 114 (318 mg, 64%) was obtained from 4-carbomethoxybutyrophenone=thiosemicarbazone prepared above, pivaloyl chloride (0.549 mL, 4.45 mmol) and pyridine (0.431 mL, 5.34 mmol).

$^1$H NMR (300 MHz, CDCl$_3$) δ (ppm): 1.29 (s, 9H), 1.32 (s, 9H), 1.51-1.60 (m, 1H), 2.10-2.30 (m, 2H), 2.44 (m, 2H), 3.03-3.17 (m, 1H), 3.68 (s, 3H), 7.20-7.36 (m, 5H), 7.9.5 (br s, 1H)

Example 108

Compound 115

In a manner similar to that in Example 99, Compound 115 (234 mg, 95%) was obtained from Compound 114 (254 mg, 0.567 mmol) prepared in Example 107, sodium hydroxide (70.0 mg, 1.75 mmol), water (2 mL) and ethanol (4 mL).

$^1$H NMR (270 MHz, CDCl$_3$) δ (ppm): 1.29 (s, 9H), 1.32 (s, 9H), 1.65-1.75 (m, 1H), 2.10-2.35 (m, 2H), 2.50 (m, 2H), 3.10-3.20 (m, 1H), 7.23-7.35 (m, 6H), 7.92 (br s, 1H)

Example 109

Compound 116

In a manner similar to that in Example 100, Compound 116 (0.028 g, 55%) was obtained from Compound 115 (50.0 mg, 0.115 mmol) prepared in Example 108, oxalyl chloride (0.5 mL) and 40% methylamine-methanol solution (5 mL).

$^1$H NMR (270 MHz, CDCl$_3$) δ (ppm): 1.29 (s, 9H), 1.32 (s, 9H), 1.50-1.65 (m, 1H), 2.21-2.35 (m, 4H), 2.80 (d, J=4.8 Hz, 3H), 3.13 (m, 1H), 5.71 (br s, 1H), 7.20-7.35 (m, 5H), 7.97 (br s, 1H)

Example 110

Compound 117

In a manner similar to that in Example 100, Compound 117 (0.024 g, 47%) was obtained from Compound 115 (51.5 mg, 0.119 mmol) prepared in Example 108, oxalyl chloride (0.5 mL) and 4 mol/L ammonia-methanol solution (5 mL).

AP-MS (m/z): 431 (M$^-$−1)

Example 111

Compound 118

In a manner similar to that in Step 3 of Example 76, Compound 118 (302 mg, 26%) was obtained from 2-(methylsulfonylamino)acetophenone=thiosemicarbazone (1.00 g, 3.49 mmol) prepared in Step 2 of Example 88, acetic anhydride (659 μL, 6.98 mmol) and pyridine (565 μL, 6.98 mmol).

$^1$H NMR (270 MHz, CDCl$_3$) δ (ppm): 2.29 (s, 3H), 2.99 (s, 3H), 4.04 (d, J=14.0 Hz, 1H), 4.55 (d, J=14.0 Hz, 1H), 7.30-7.41 (m, 5H)

AP-MS (m/z): 329 (M$^+$+1)

Example 112

Compound 119

Compound 118 (10.6 mg, 0.0323 mmol) prepared in Example 111 was dissolved in tetrahydrofuran (80 mL). To the solution was added dimethylaminopyridine (7.9 mg, 0.0646 mmol) and pyridine (7.8 μL, 0.0969 mmol), and the mixture was cooled to 0° C. To the solution was added pivaloyl chloride (20 μL, 0.162 mmol), and the moisture was stirred at 0° C. for 5 minutes, and further stirred at room temperature for 4 hours. To the reaction mixture was added water and 1 mol/L hydrochloric acid, and extracted with ethyl acetate. The organic layer was dried over anhydrous sodium sulfate, and the solvent was evaporated under reduced pressure. The residue was purified by preparative thin layer chromatography (chloroform/methanol=12/1) to obtain Compound 119 (6.3 mg, 40%).

$^1$H-NMR (270 MHz, CDCl$_3$) δ (ppm): 1.27 (s, 9H), 2.32 (s, 3H), 2.95 (s, 3H), 3.98 (dd, J=5.2, 14.0 Hz, 1H), 4.60 (dd, J=8.1, 13.9 Hz, 1H), 5.40 (m, 1H), 7.29-7.40 (m, 5H), 8.11 (br s, 1H)

Example 113

Compound 120

2-(Methylsulfonylamino)acetophenone=thiosemicarbazone (300 mg, 1.05 mmol) prepared in Step 2 of Example 88 was dissolved in tetrahydrofuran (18 mL). To the solution was added 4-dimethylaminopyridine (641 mg, 5.25 mmol) and pivaloyl chloride (0.13 mL, 1.1 mmol), and the mixture was stirred at room temperature. To the mixture was further added, after 1 hour and after 2 hours each, pivaloyl chloride (0.065 mL, 0.53 mmol), and the mixture was stirred for 3.6 hours in total. To the reaction mixture was added water, and the mixture was extracted with ethyl acetate. The organic layer was washed with saturated aqueous sodium chloride, and then dried over anhydrous sodium sulfate. The solvent was evaporated under reduced pressure, and the residue was purified by preparative thin layer chromatography (chloroform/methanol=20/1) to obtain Compound 120 (88 mg, yield 22%).

$^1$H NMR (270 MHz, CDCl$_3$) δ (ppm): 1.34 (s, 9H), 2.96 (s, 3H), 4.06 (dd, J=6.2, 13.7 Hz, 1H), 4.19 (br s, 2H), 4.58 (dd, J=7.0, 13.7 Hz, 1H), 6.20 (t, J=6.4 Hz, 1H), 7.27-7.55 (m, 5H)

AP-MS (m/z): 371 (M$^+$+1)

Example 114

Compound 121

6-Bromohexanoic acid (469 mg, 2.41 mmol) was dissolved in dichloromethane (15 mL). To the solution was added oxalyl chloride (0.28 mL, 3.2 mmol), and the mixture was stirred at room temperature for 2 hours. The solvent was evaporated from the reaction mixture under reduced pressure, and the resulting residue was dissolved in dichloromethane (15 mL). To the solution was added Compound 120 (297 mg, 0.802 mmol) prepared in Example 113 and pyridine (0.20 mL, 2.4 mmol), and the mixture was stirred at room temperature for 1 hour. After the reaction mixture was concentrated under reduced pressure, water was added to the residue, and the solution was extracted with ethyl acetate. The organic layer was washed with saturated aqueous sodium chloride, and then dried over anhydrous sodium sulfate. The solvent was evaporated under reduced pressure, and the residue was purified by preparative thin layer chromatography (chloroform/methanol=30/1) to obtain Compound 121 (315 mg, yield 72%).

$^1$H NMR (270 MHz, CDCl$_3$) δ (ppm): 1.32 (s, 9H), 1.50 (m, 2H), 1.67 (m, 2H), 1.86 (q, J=6.7 Hz, 2H), 2.34 (t, J=7.3 Hz, 2H), 2.98 (s, 3H), 3.40 (t, J=6.6 Hz, 2H), 3.99 (dd, J=5.2, 13.6 Hz, 1H), 4.63 (dd, J=8.2, 13.6 Hz, 1H), 5.24 (dd, J=5.5, 7.9 Hz, 1H), 7.26-7.38 (m, 5H), 8.40 (br s, 1H)

AP-MS (m/z): 547 (M$^+$+1)

Example 115

Compound 122

Compound 121 (315 mg, 0.575 mmol) prepared in Example 114 was dissolved in N,N-diethylformamide (9.5 mL). To the solution was added sodium azide (187 mg, 2.88 mmol), and the mixture was stirred at 80° C. for 2 hours. To the reaction mixture was added water and the mixture was extracted with ethyl acetate. The organic layer was washed with saturated aqueous sodium chloride, and then dried over anhydrous sodium sulfate. The solvent was evaporated under reduced pressure, and the residue was purified by preparative thin layer chromatography (hexane/ethyl acetate=1/2) to obtain Compound 122 (211 mg, yield 72%).

$^1$H NMR (270 MHz, CDCl$_3$) δ (ppm): 1.32 (s, 9H), 1.42 (m, 2H), 1.55-1.74 (m, 4H), 2.35 (t, J=7.3 Hz, 2H), 2.97 (s, 3H), 3.28 (t, J=6.7 Hz, 2H), 4.13 (dd, J=7.2, 14.3 Hz, 1H), 4.63 (dd, J=8.3, 13.5 Hz, 1H), 5.21 (dd, J=5.2, 8.0 Hz, 1H), 7.26-7.38 (m, 5H), 8.37 (s, 1H)

AP-MS (m/z): 510 (M$^+$+1)

Example 116

Compound 123

Compound 122 (23.6 mg, 0.0463 mmol) prepared in Example 115 was dissolved in tetrahydrofuran (1.0 mL). To the solution was added triphenylphosphine (36.4 mg, 0.139 mmol), and the mixture was stirred at room temperature for 25 minutes. To the reaction mixture was added water, and the mixture was extracted with ethyl acetate. The organic layer was washed with saturated aqueous sodium chloride, and then dried over anhydrous sodium sulfate. The solvent was evaporated under reduced pressure, and the residue was purified by preparative thin layer chromatography (chloroform/methanol/ammonia=5/0.8 10.2) to obtain Compound 123 (7.1 mg, yield 32%).

$^1$H-NMR (270 MHz, CDCl$_3$) δ (ppm): 1.31 (s, 9H), 1.47 (m, 2H), 1.57 (m, 2H), 1.70 (m, 2H), 2.39 (m, 2H), 2.82 (m, 2H), 2.97 (s, 3H), 3.95 (d, J=13.7 Hz, 1H), 4.14 (br s, 3H), 4.65 (d, J=13.5 Hz, 1H), 7.24-7.35 (m, 5H)

AP-MS (m/z): 484 (M$^+$+1)

Example 117

Compound 124

Compound 123 (5.0 mg, 0.010 mmol) prepared in Example 116 was dissolved in dichloromethane (0.4 mL). To the solution was added pyridine (0.0025 mL, 0.031 mmol) and acetyl chloride (0.0015 mL, 0.021 mmol), and the mixture was stirred at room temperature for 0.8 hour. To the reaction mixture was added water and the mixture was extracted with ethyl acetate. The organic layer was washed with saturated aqueous sodium chloride, and then dried over anhydrous sodium sulfate. The solvent was evaporated under reduced pressure, and the residue was purified by preparative thin layer chromatography (chloroform/methanol=20/1) to obtain Compound 124 (3.9 mg, yield 72%).

$^1$H NMR (270 MHz, CDCl$_3$) δ (ppm): 1.32 (s, 9H), 1.37 (m, 2H), 1.53 (m, 2H), 1.69 (m, 2H), 1.98 (s, 3H), 2.39 (t, J=7.4 Hz, 2H), 2.97 (s, 3H), 3.24 (m, 2H), 3.98 (dd, J=5.2, 13.6 Hz, 1H), 4.64 (dd, J=8.2, 13.5 Hz, 1H), 5.22 (dd, J=5.4, 8.2 Hz, 1H), 5.68 (m, 1H), 7.24-7.38 (m, 5H), 9.08 (s, 1H)

FAB-MS (m/z): 526 (M$^+$+1)

Example 118

Compound 125

Step 1: In a manner similar to that in Step 1 of Example 1, 3'-hydroxyacetophenone=4-ethylthiosemicarbazone (342 mg, 70%) was obtained from 3'-hydroxyacetophenone (279 mg, 2.05 mmol) and 4-ethylthiosemicarbazide (242 mg, 2.03 mmol).

Step 2: In a manner similar to that in Step 2 of Example 1, Compound 125 (90 mg, 60%) was obtained from 3'-hydroxyacetophenone=4-ethylthiosemicarbazone (200 mg, 0.843 mmol) prepared above, acetic anhydride (260 mg, 2.53 mmol) and pyridine (108 μL, 1.34 mmol).

$^1$H NMR (270 MHz, CDCl$_3$) δ (ppm): 2.02 (s, 3H), 2.20 (s, 3H), 2.28 (s, 3H), 2.30 (t, J=8.4 Hz, 3H), 2.36 (s, 3H), 3.30-3.47 (br s, 2H), 7.20-7.40 (m, 5H)

Example 119

Compound 126

In a manner similar to that in Example 65, Compound 126 (81 mg, 49%) was obtained from Compound 125 (187 mg, 0.515 mg) prepared in Example 118, methanol (10 mL) and potassium carbonate (1.00 g, 7.24 mmol).

$^1$H NMR (270 MHz, DMSO-d$_6$) δ (ppm): 2.01 (s, 3H), 2.18 (s, 3H), 2.23 (s, 3H), 2.29 (t, J=8.4 Hz, 3H), 3.40 (br s, 2H), 6.65-6.80 (m, 3H), 7.13 (m, 1H), 11.6 (br s, 1H)

Example 120

Compound 127

Compound 69 (50.5 mg, 0.172 mmol) prepared in Example 66 was dissolved in dichloromethane (0.5 mL). To the solution was added triethylamine (17.4 mg, 0.172 mmol) and ethyl isocyanate (13.6 μL, 0.172 mmol), and the mixture was stirred at room temperature for 12 hours. To the reaction mixture was added 1 mol/L hydrochloric acid and water, and the mixture was subjected to separation. The organic layer was washed with saturated aqueous sodium chloride and dried over anhydrous sodium sulfate. The solvent was evaporated under reduced pressure, and the residue was purified by preparative thin layer chromatography (chloroform/methanol/water=90/10/1) to obtain Compound 127 (53.3 mg, 85%).

$^1$H NMR (270 MHz, CDCl$_3$) δ (ppm): 1.21 (t, J=7.0 Hz, 3H), 2.09 (s, 3H), 2.22 (s, 3H), 2.35 (s, 3H), 3.31 (m, 2H), 5.03 (br s, 1H), 7.06 (br d, J=8.4 Hz, 1H), 7.24-7.35 (m, 3H), 8.41 (br s, 1H)

Example 121

Compound 128

In a manner similar to that in Step 3 of Example 76, Compound 128 (500 mg, 63%) was obtained from 3'-hydroxyacetophenone=thiosemicarbazone (398 mg, 1.90 mmol) prepared in Step 1 of Example 59, isobutyryl chloride (1.56 mL, 7.60 mmol) and pyridine (721 mg, 9.12 mmol).

$^1$H NMR (270 MHz, CDCl$_3$) δ (ppm): 1.09 (d, J=6.8 Hz, 3H), 1.10 (d, J=6.8 Hz, 3H), 1.21 (d, J=6.8 Hz, 3H), 1.22 (d, J=6.8 Hz, 3H), 1.29 (d, J=7.3 Hz, 6H), 2.34 (s, 3H), 2.51 (m, 1H), 2.78 (m, 1H), 3.18 (m, 1H), 7.00 (br d, J=7.3 Hz, 1H), 7.13 (br s, 1H), 7.25-7.33 (m, 2H), 7.93 (br s, 1H)

Example 122

Compound 129

In a manner similar to that in Example 65, Compound 129 (298 mg, 85%) was obtained from Compound 128 (420 mg, 1.00 mmol) prepared in Example 121 and potassium carbonate (1.00 g, 7.24 mmol).

$^1$H NMR (270 MHz, CDCl$_3$) δ (ppm): 1.11 (d, J=7.0 Hz, 3H), 1.12 (d, J=7.0 Hz, 3H), 1.22 (d, J=7.0 Hz, 3H), 1.23 (d, J=7.0 Hz, 3H), 2.23 (s, 3H), 2.51 (m, 1H), 3.20 (m, 1H), 5.60

(br s, 1H), 6.63 (br d, J=7.3 Hz, 1H), 6.85 (br s, 1H), 6.94 (br d, J=7.9 Hz, 1H), 7.15 (br t, J=7.9 Hz, 1H), 8.00 (br s, 1H)

Example 123

Compound 130

In a manner similar to that in Step 3 of Example 76, Compound 130 (389 mg, 88%) was obtained from 2'-chloroacetophenone=thiosemicarbazone (253 mg, 1.11 mmol) prepared in Step 1 of Example 53, pivaloyl chloride (546 µL, 4.44 mmol) and pyridine (389 µL, 4.80 mmol).

$^1$H NMR (270 MHz, CDCl$_3$) δ (ppm): 1.29 (s, 9H), 1.30 (s, 9H), 2.35 (s, 3H), 7.20-7.27 (m, 2H), 7.35-7.43 (m, 2H), 7.95 (br s, 1H)

Example 124

Compound 131

In a manner similar to that in Step 3 of Example 76, Compound 131 (389 mg, 86%) was obtained from 2'-chloroacetophenone=thiosemicarbazone (400 mg, 1.89 mmol) prepared in Step 1 of Example 53, isobutyryl chloride (594 µL, 5.67 mmol) and pyridine (538 mg, 6.80 mmol).

$^1$H NMR (270 MHz, CDCl$_3$) δ (ppm): 1.10 (d, J=6.6 Hz, 3H), 1.12 (d, J=6.6 Hz, 3H), 1.23 (d, J=6.9 Hz, 2H), 1.25 (d, J=6.9 Hz, 3H), 2.39 (s, 3H), 2.52 (m, 1H), 3.18 (m, 1H), 7.22-7.28 (m, 2H), 7.37-7.45 (m, 2H), 7.96 (br s, 1H)

Example 125

Compound 132

Step 1: In a manner similar to that in Step 1 of Example 1, 1-(5-bromo-2-thienyl)ethanone=thiosemicarbazone (7.33 mg, 86%) was obtained from 1-(5-bromo-2-thienyl)ethanone (630 mg, 3.07 mmol) and thiosemicarbazide (281 mg, 3.07 mmol).

Step 2: In a manner similar to that in Step 2 of Example 1, Compound 132 (158 mg, 58%) was obtained from 1-5-bromo-2-thienyl)ethanone=thiosemicarbazone (2.11 mg, 0.758 mmol) prepared above and acetic anhydride (10 mL).

$^1$H NMR (270 MHz, CDCl$_3$) δ (ppm): 2.15 (s, 3H), 2.19 (s, 3H), 2.36 (s, 3H), 6.84 (br s, 1H), 6.86 (br s, 1H), 8.29 (br s, 1H)

Example 126

Compound 133

Step 1: In a manner similar to that in Step 1 of Example 1, 1-(3-bromo-2-thienyl)ethanone=thiosemicarbazone was obtained from 1-(3-bromo-2-thienyl)ethanone (108 mg, 0.388 mmol) and thiosemicarbazide (36.5 mg, 0.399 mmol).

Step 2: In a manner similar to that in Step 2 of Example 1, Compound 133 (139 mg, 99%) was obtained from 1-(3-bromo-2-thienyl)ethanone=thiosemicarbazone prepared above and acetic anhydride (10 mL).

$^1$H NMR (270 MHz, CDCl$_3$) δ (ppm): 2.04 (s, 3H), 2.14 (s, 3H), 2.23 (s, 3H), 2.41 (s, 3H), 6.96 (br s, 1H), 7.17 (br s, 1H), 9.08 (br s, 1H)

Example 127

Compound 134

Step 1: In a manner similar to that in Step 1 of Example 1, 1-(3-chloro-2-thienyl)ethanone=thiosemicarbazone was obtained from 1-(3-chloro-2-thienyl)ethanone (137 mg, 0.853 mmol) and thiosemicarbazide (78 mg, 0.853 mmol).

Step 2: In a manner similar to that in Step 2 of Example 1, Compound 134 (158 mg, 58%) was obtained from 1-(3-chloro-2-thienyl)ethanone=thiosemicarbazone prepared above and acetic anhydride (10 mL).

$^1$H NMR (270 MHz, CDCl$_3$) δ (ppm): 2.14 (s, 3H), 2.21 (s, 3H), 2.43 (s, 3H), 6.89 (d, J=5.3 Hz, 1H), 7.18 (d, J=5.3 Hz, 1H), 8.28 (br s, 1H)

Example 128

Compound 135

Step 1: In a manner similar to that in Step 1 of Example 1, 1-(3-chloro-2-thienyl)ethanone=thiosemicarbazone (96.1 mg, 71%) was obtained from 1-(3-chloro-2-thienyl)ethanone (92.9 mg, 0.578 mmol) and thiosemicarbazide (52.9 mg, 0.578 mmol).

Step 2: In a manner similar to that in Step 3 of Example 76, Compound 134 (90 mg, 60%) was obtained from 1-(3-chloro-2-thienyl)ethanone=thiosemicarbazone (86.9 mg, 0.372 mmol) prepared above, pivaloyl chloride (138 µL, 1.12 mmol) and pyridine (108 µL, 1.34 mmol).

$^1$H NMR (270 MHz, CDCl$_3$) δ (ppm): 1.33 (s, 9H), 1.35 (s, 9H), 2.43 (s, 3H), 6.90 (d, J=6.3 Hz, 1H), 7.20 (d, J=6.3 Hz, 1H), 7.97 (br s, 1H)

Example 129

Compound 136

Compound 14 (41 mg, 0.17 mmol) prepared in Example 11 was dissolved in acetonitrile (0.5 mL). To the solution was added di-tert-butyl dicarbonate (0.114 mg, 0.522 mmol) and DMAP (43 mg, 0.35 mmol), and the mixture was stirred at room temperature for 1 hour. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform/methanol=20/1) to obtain Compound 136 (24 mg, 41%).

$^1$H NMR (270 MHz, CDCl$_3$) δ (ppm): 1.47 (s, 9H), 2.21 (s, 3H), 2.40 (s, 3H), 7.14-7.48 (m, 6H)

AP-MS (m/z): 334 (M$^-$−1)

Example 130

Compound 137

Compound 14 (74 mg, 0.31 mmol) prepared in Example 11 was dissolved in N,N-dimethylformamide (2 mL). To the solution was added 60% sodium hydride (50 mg, 1.3 mmol) and dimethylcarbamoyl chloride (0.116 mL, 1.26 mmol), and the mixture was stirred at room temperature for 1 hour. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform/methanol=40/1, then ethyl acetate/n-hexane=3/1) to obtain Compound 137 (44 mg, 46%).

$^1$H NMR (270 MHz, CDCl$_3$) δ (ppm): 2.23 (s, 3H), 2.37 (s, 3H), 3.00 (s, 6H), 7.20-7.45 (m, 5H)

AP-MS (m/z): 307 (M$^+$+1)

Example 131

Compound 138

Step 1: Copper (II) bromide (130 mg, 0.583 mmol) was dissolved in acetonitrile (5.4 mL). To the solution was added tert-butyl nitrite (0.093 mL, 0.78 mmol) under ice cooling. After being stirred for 10 minutes, to the mixture was added Compound 14 (180 mg, 0.486 mmol) prepared in Example 11, and the mixture was stirred for 1 hour with gradually raising the temperature up to room temperature. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by silica gel column chromatography (ethyl acetate/n-hexane=1/18) to obtain 3-acetyl-5-bromo-2-methyl-2-phenyl-1,3,4-thiadialine (145 mg, 84%).

Step 2: 3-Acetyl-5-bromo-2-methyl-2-phenyl-1,3,4-thiadialine (50 mg, 0.17 mmol) prepared above was dissolved in dichloromethane (0.5 mL). To the solution was added piperidine (0.033 mL, 0.33 mmol), and the mixture was stirred at room temperature for 20 minutes. To the reaction mixture was further added piperidine (0.165 mL, 1.67 mmol), and the mixture was stirred at the same temperature for 5.5 hours. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform) to obtain Compound 138 (12 mg, 24%).

$^1$H NMR (270 MHz, CDCl$_3$) δ (ppm): 1.60 (m, 6H), 2.25 (s, 3H), 2.40 (s, 3H), 3.24 (m, 4H), 7.20-7.39 (m, 3H), 7.45 (m, 2H)

AP-MS (m/z): 304 (M$^+$+1)

Example 132

Compound 139

In a manner similar to that in Step 2 of Example 131, Compound 139 (38 mg, 59%) was obtained from 3-acetyl-5-bromo-2-methyl-2-phenyl-1,3,4-thiadiallyn (61 mg, 0.20 mmol) prepared in Step 1 of Example 131 and 4-methylpiperidine (0.483 mL, 4.08 mmol).

$^1$H NMR (270 MHz, CDCl$_3$) δ (ppm): 0.96 (d, J=6.4 Hz, 3H), 1.25 (m, 2H), 1.44-1.71 (m, 3H), 2.25 (s, 3H), 2.40 (s, 3H), 2.88 (m, 2H), 3.61 (m, 2H), 7.20-7.49 (m, 3H), 7.46 (m, 2H)

AP-MS (m/z): 318 (M$^+$+1)

Example 133

Compound 140

Compound 118 (50 mg, 0.15 mmol) prepared in Example 111 was dissolved in dichloromethane (2 mL). To the solution was added pyridine (0.031 mL, 0.38 mmol) and hexanoyl chloride (0.053 mL, 0.38 mmol), and the mixture was stirred at room temperature for 2.5 hours. To the reaction mixture was further added pyridine (0.012 mL, 0.15 mmol) and hexanoyl chloride (0.021 mL, 0.15 mmol), and the mixture was stirred at the same temperature for 1 hour. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform/methanol=15/1) to obtain Compound 140 (52 mg, 80%).

$^1$H NMR (270 MHz, CDCl$_3$) δ (ppm): 0.96 (t, J=6.6 Hz, 3H), 1.22-1.41 (m, 4H), 1.64 (m, 2H), 2.31 (s, 3H), 2.32 (t, J=7.5 Hz, 2H), 2.96 (s, 3H), 3.98 (dd, J=5.4, 13.9 Hz, 1H), 4.60 (dd, J=8.1, 13.9 Hz, 1H), 5.38 (dd, J=5.4, 8.1 Hz, 1H), 7.20-7.44 (m, 5H), 8.02 (s, 1H)

AP-MS (m/z): 427 (M$^+$+1)

Example 134

Compound 141

In a manner similar to that in Example 133, Compound 141 (22 mg, 18%) was obtained from Compound 118 (100 mg, 0.305 mmol) prepared in Example 111, pyridine (0.062 mL, 0.78 mmol) and crotonoyl chloride (0.075 mL, 0.78 mmol).

$^1$H NMR (270 MHz, CDCl$_3$) δ (ppm): 1.91 (dd, J=1.7, 7.0 Hz, 3H), 2.32 (s, 3H), 2.97 (s, 3H), 3.99 (dd, J=5.6, 13.9 Hz, 1H), 4.61 (dd, J=7.6, 13.9 Hz, 1H), 5.51 (dd, J=5.6, 7.6 Hz, 1H), 5.86 (dd, J=1.7, 15.2 Hz, 1H), 7.03 (dd, J=7.0, 15.2 Hz, 1H), 7.22-7.41 (m, 5H), 8.49 (s, 1H)

AP-MS (m/z): 397 (M$^+$+1)

Example 135

Compound 142

In a manner similar to that in Example 133, Compound 142 (42 mg, 70%) was obtained from Compound 118 (50 mg, 0.15 mmol) prepared in Example 111, pyridine (0.062 mL, 0.76 mmol) and cyclopropanecarbonyl chloride (0.070 mL, 0.76 mmol).

$^1$H NMR (270 MHz, CD$_3$OD) δ (ppm): 0.87-0.98 (m, 4H), 1.77 (m, 1H), 2.28 (s, 3H), 3.01 (s, 3H), 3.97 (d, J=14.0 Hz, 1H), 4.55 (d, J=14.0 Hz, 1H), 7.22-7.42 (m, 5H)

AP-MS (m/z): 397 (M$^+$+1)

Example 136

Compound 143

In a manner similar to that in Example 133, Compound 143 (24 mg, 22%) was obtained from Compound 118 (80 mg, 0.24 mmol) prepared in Example 111, pyridine (0.069 mL, 0.85 mmol) and 2-acetoxyisobutyryl chloride (0.12 mL, 0.85 mmol).

$^1$H NMR (270 MHz, CDCl$_3$) δ (ppm): 1.65 (s, 3H), 1.67 (s, 3H), 2.15 (s, 3H), 2.32 (8, 3H), 2.97 (s, 3H), 3.99 (dd, J=5.5, 14.0 Hz, 1H), 4.61 (dd, J=8.1, 14.0 Hz, 1H), 5.39 (dd, J=5.5, 8.1 Hz, 1H), 7.29-7.46 (m, 5H), 8.53 (s, 1H)

AP-MS (m/z): 457 (M$^+$+1)

Example 137

Compound 144

Compound 143 (21 mg, 0.045 mmol) prepared in Example 136 was dissolved in a mixed solvent of methanol (1.6 mL) and water (0.8 mL). To the solution was added lithium hydroxide (11 mg, 0.45 mmol), and the mixture was stirred at room temperature for 3.5 hours. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform/methanol=9/1) to obtain Compound 144 (11 mg, 56%).

$^1$H NMR (270 MHz, CDCl$_3$) δ (ppm): 1.44 (s, 3H), 1.48 (s, 3H), 2.32 (s, 3H), 2.85 (br s, 1H), 2.97 (s, 3H), 3.98 (dd, J=5.6, 13.9 Hz, 1H), 4.63 (dd, J=7.8, 13.9 Hz, 1H), 5.53 (dd, J=5.6, 7.8 Hz, 1H), 7.25-7.42 (m, 5H), 9.36 (s, 1H)

AP-MS (m/z): 415 (M$^+$+1)

Example 138

Compound 145

In a manner similar to that in Example 133, Compound 145 (53 mg, 86%) was obtained from Compound 118 (50 mg, 0.15 mmol) prepared in Example 111, pyridine (0.031 mL, 0.38 mmol) and methoxyacetyl chloride (0.035 mL, 0.38 mmol).

$^1$H NMR (270 MHz, CDCl$_3$) δ (ppm): 2.32 (s, 3H), 2.96 (s, 3H), 3.49 (s, 3H), 4.00 (s, 2H), 4.00 (dd, J=5.8, 13.9 Hz, 1H), 4.61 (dd, J=7.8, 13.9 Hz, 1H), 5.46 (dd, J=5.8, 7.8 Hz, 1H), 7.25-7.44 (m, 5H), 8.94 (s, 1H)

AP-MS (m/z): 401 (M$^+$+1)

Example 139

Compound 146

In a manner similar to that in Example 133, Compound 146 (105 mg, 85%) was obtained from Compound 118 (100 mg, 0.305 mmol) prepared in Example 111, pyridine (0.062 mL, 0.76 mmol) and chloroacetyl chloride (0.061 mL, 0.76 mmol).

$^1$H NMR (270 MHz, CDCl$_3$) δ (ppm): 2.34 (s, 3H), 2.97 (s, 3H), 4.02 (dd, J=5.6, 14.0 Hz, 1H), 4.11 (d, J=15.9 Hz, 1H), 4.18 (d, J=15.9 Hz, 1H), 4.62 (dd, J=7.8, 14.0 Hz, 1H), 5.28 (dd, J=5.6, 7.8 Hz, 1H), 7.22-7.43 (m, 5H), 8.87 (s, 1H)

AP-MS (m/z): 405 (M$^+$+1)

Example 140

Compound 147

Compound 146 (50 mg, 0.12 mmol) prepared in Example 139 was dissolved in methanol (1 mL). To the solution was added 50% aqueous dimethylamine (0.033 mL), and the mixture was stirred at room temperature for 1 hour. To the reaction mixture was further added 50% aqueous dimethylamine (0.033 mL), and the mixture was stirred at the same temperature for 1.5 hours. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform/acetone=1/1) to obtain Compound 147 (20 mg, 39%).

$^1$H NMR (270 MHz, CDCl$_3$) δ (ppm): 2.34 (s, 3H), 2.38 (s, 6H), 2.96 (s, 3H), 3.06 (d, J=17.3 Hz, 1H), 3.10 (d, J=17.3 Hz, 1H), 4.00 (d, J=13.9 Hz, 1H), 4.61 (d, J=13.9 Hz, 1H), 5.36 (br, 1H), 7.25-7.41 (m, 5H)

AP-MS (m/z): 414 (M$^+$+1)

Example 141

Compound 148

In a manner similar to that in Example 133, Compound 148 (304 mg, 74%) was obtained from Compound 118 (297 mg, 0.903 mmol) prepared in Example 111, pyridine (0.183 mL, 2.26 mmol) and methyl 4-(chloroformyl)butyrate (0.312 mL, 2.26 mmol).

$^1$H NMR (270 MHz, CDCl$_3$) δ (ppm): 2.00 (m, 2H), 2.32-2.56 (m, 4H), 2.34 (s, 3H), 2.99 (s, 3H), 3.71 (s, 3H), 4.01 (dd, J=5.4, 13.9 Hz, 1H), 4.63 (dd, J=7.9, 13.9 Hz, 1H), 5.45 (m, 1H), 7.21-7.49 (m, 5H), 8.54 (s, 1H)

AP-MS (m/z): 457 (M$^+$+1)

Example 142

Compound 149

In a manner similar to that in Example 137, after Compound 148 (262 mg, 0.573 mmol) prepared in Example 141 was treated with lithium hydroxide monohydrate (206 mg, 4.91 mmol), to the reaction mixture was added ice and 0.5 mol/L hydrochloric acid, and the mixture was extracted with a mixed solvent of chloroform and methanol. After the extract was concentrated, the residue was purified by silica gel column chromatography (chloroform/methanol 43/7) to obtain Compound 149 (222 mg, 88%).

$^1$H NMR (270 MHz, CD$_3$OD) δ (ppm): 1.89 (m, 2H), 2.28 (s, 3H), 2.33 (t, J=7.3 Hz, 2H), 2.43 (t, J=7.5 Hz, 2H), 3.01 (s, 3H), 3.99 (d, J=14.0 Hz, 1H), 4.56 (d, J=14.0 Hz, 1H), 7.20-7.45 (m, 5H)

AP-MS (m/z): 441 (M$^-$−1)

Example 143

Compound 150

Compound 149 (83 mg, 0.19 mmol) prepared in Example 142 was dissolved in 1,2-dichloroethane (3.2 mL). To the solution was added thionyl chloride (3.2 mL), and the mixture was stirred at 60° C. for 2.5 hours. The reaction mixture was concentrated under reduced pressure, and then the residue was purified by preparative thin layer chromatography (chloroform/methanol=20/1) to obtain Compound 150 (61 mg, 76%).

$^1$H NMR (270 MHz, CDCl$_3$) δ (ppm): 2.09 (m, 2H), 2.29 (s, 3H), 2.80 (t, J=6.5 Hz, 4H), 3.05 (s, 3H), 3.95 (dd, J=3.7, 13.9 Hz, 1H), 4.82 (dd, J=9.6, 13.9 Hz, 1H), 5.70 (dd, J=3.7, 9.6 Hz, 1H), 7.29-7.47 (m, 3H), 7.58 (m, 2H)

AP-MS (m/z): 425 (M$^+$+1)

Example 144

Compound 151

In a manner similar to that in Example 133, Compound 151 (113 mg, 78%) was obtained from Compound 118 (100 mg, 0.305 mmol) prepared in Example 111, pyridine (0.062 mL, 0.76 mmol) and 4-bromobutyryl chloride (0.088 mL, 0.76 mmol).

$^1$H NMR (270 MHz, CDCl$_3$) δ (ppm): 2.20 (m, 2H), 2.31 (s, 3H), 2.55 (t, J=6.9 Hz, 2H), 2.96 (s, 3H), 3.47 (t, J=6.2 Hz, 2H), 3.99 (dd, J=5.5, 13.9 Hz, 1H), 4.61 (dd, J=7.9, 13.9 Hz, 1H), 5.37 (dd, J=5.5, 7.9 Hz, 1H), 7.23-7.42 (m, 5H), 8.18 (s, 1H)

AP-MS (m/z): 476 (M$^-$−1)

Example 145

Compound 152

Compound 151 (70 mg, 0.15 mmol) prepared in Example 144 was dissolved in N,N-dimethylformamide (1.8 mL). To the solution was added 60% sodium hydride (9 mg, 0.2 mmol), and the mixture was stirred at room temperature for 2 hours. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by preparative thin layer chromatography (chloroform/methanol=9/1) to obtain Compound 152 (51 mg, 88%).

$^1$H NMR (270 MHz, CDCl$_3$) δ (ppm): 2.20 (m, 2H), 2.35 (s, 3H), 2.57 (m, 2H), 2.95 (s, 3H), 3.93 (m, 2H), 3.99 (dd, J=5.5, 13.9 Hz, 1H), 4.61 (dd, J=8.1, 13.9 Hz, 1H), 5.33 (dd, J=5.5, 8.1 Hz, 1H), 7.25-7.44 (m, 5H)

AP-MS (m/z): 397 (M$^+$+1)

Example 146

Compound 153

In a manner similar to that in Example 133, Compound 153 (120 mg, 80%) was obtained from Compound 118 (100 mg, 0.305 mmol) prepared in Example 111, pyridine (0.087 mL, 1.1 mmol) and 5-bromovaleryl chloride (0.143 mL, 1.07 mmol).

$^1$H NMR (270 MHz, CDCl$_3$) δ (ppm): 1.75-1.98 (m, 4H), 2.31 (s, 3H), 2.36 (t, J=7.0 Hz, 2H), 2.96 (s, 3H), 3.40 (t, J=6.2 Hz, 2H), 3.99 (dd, J=5.5, 13.9 Hz, 1H), 4.61 (dd, J=7.9, 13.9 Hz, 1H), 5.40 (dd, J=5.5, 7.9 Hz, 1H), 7.23-7.42 (m, 5H), 8.22 (s, 1H)

AP-MS (m/z): 491, 493 (M$^+$+1)

Example 147

Compound 154

In a manner similar to that in Example 145, Compound 154 (36 mg, 72%) was obtained from Compound 153 (60 mg, 0.12 mmol) prepared in Example 146 and 60% sodium hydride (7 mg, 0.2 mmol).

$^1$H NMR (270 MHz, CDCl$_3$) δ (ppm): 1.81-2.02 (m, 4H), 2.36 (s, 3H), 2.54 (m, 2H), 2.94 (s, 3H), 3.85 (m, 2H), 3.95 (dd, J=4.8, 13.8 Hz, 1H), 4.56 (dd, J=8.4, 13.8 Hz, 1H), 5.41 (dd, J=4.8, 8.4 Hz, 1H), 7.25-7.41 (m, 5H)

AP-MS (m/z): 411 (M$^+$+1)

Example 148

Compound 155

In a manner similar to that in Example 133, Compound 155 (122 mg, 80%) was obtained from Compound 118 (99 mg, 0.3.0 mmol) prepared in Example 111, pyridine (0.061 mL, 0.75 mmol) and 6-bromohexanoyl chloride (0.115 mL, 0.754 mmol).

$^1$H NMR (270 MHz, CDCl$_3$) δ (ppm): 1.40-1.77 (m, 4H), 1.87 (m, 2H), 2.31 (s, 3H), 2.35 (t, J=7.4 Hz, 2H), 2.96 (s, 3H), 3.40 (t, J=6.6 Hz, 2H), 3.99 (dd, J=5.4, 14.0 Hz, 1H), 4.60 (dd, J=7.9, 14.0 Hz, 1H), 5.36 (dd, J=5.4, 7.9 Hz, 1H), 7.20-7.43 (m, 5H), 8.06 (s, 1H)

AP-MS (m/z): 505, 507 (M$^+$+1)

Example 149

Compound 156

In a manner similar to that in Example 145, Compound 156 (17 mg, 32%) was obtained from Compound 155 (63 mg, 0.12 mmol) prepared in Example 148 and 60% sodium hydride (7 mg, 0.2 mmol).

$^1$H NMR (270 MHz, DMSO-d$_6$) δ (ppm): 1.55-1.78 (m, 6H), 2.19 (s, 3H), 2.68 (m, 2H), 2.95 (s, 3H), 3.87 (dd, J=7.9, 13.7 Hz, 1H), 4.12 (m, 2H), 4.29 (dd, J=5.6, 13.7 Hz, 1H), 7.20-7.41 (m, 6H)

AP-MS (m/z): 425 (M$^+$+1)

Example 150

Compound 157

Compound 99 (1.50 g, 3.21 mmol) prepared in Example 92 was dissolved in methanol (30 mL). To the solution was gradually added sodium borohydride (1.21 g, 32.0 mmol) at 50° C., and the mixture was stirred at the same temperature for 1.5 hours. To the reaction mixture was added water, and the mixture was extracted with ethyl acetate. The organic layer was washed with saturated aqueous sodium chloride, and then dried over anhydrous sodium sulfate, and the solvent was evaporated under reduced pressure. The residue was purified by silica gel column chromatography (chloroform/methanol=20/1) to obtain Compound 157 (0.26 g, 21%).

$^1$H NMR (270 MHz, CDCl$_3$) δ (ppm): 1.31 (s, 9H), 2.62 (m, 1H), 2.94 (s, 3H), 3.22 (m, 1H), 3.41 (m, 1H), 3.61 (m, 1H), 4.21 (s, 2H), 4.79 (m, 1H), 7.19-7.38 (m, 5H)

AP-MS (m/z): 385 (M$^+$+1)

Example 151

Compound 158

In a manner similar to that in Example 133, Compound 158 (114 mg, 85%) was obtained from Compound 157 (97 mg, 0.25 mmol) prepared in Example 150, pyridine (0.051 mL, 0.63 mmol) and 4-bromobutyryl chloride (0.073 mL, 0.63 mmol).

$^1$H NMR (270 MHz, CDCl$_3$) δ (ppm): 1.32 (s, 9H), 2.22 (m, 2H), 2.58 (t, J=7.4 Hz, 2H), 2.65 (m, 1H), 2.97 (s, 3H), 3.27 (m, 1H), 3.39 (m, 1H), 3.49 (t, J=6.2 Hz, 2H), 3.62 (m, 1H), 4.45 (br t, 1H), 7.21-7.39 (m, 5H), 8.00 (s, 1H)

AP-MS (m/z): 533, 535 (M$^+$+1)

Example 152

Compound 159

In a manner similar to that in Example 145, Compound 159 (64 mg, 68%) was obtained from Compound 158 (110 mg, 0.206 mmol) prepared in Example 151 and 60% sodium hydride (12 mg, 0.31 mmol).

$^1$H NMR (270 MHz, CDCl$_3$) δ (ppm): 1.34 (s, 9H), 2.23 (m, 2H), 2.56 (m, 2H), 2.61 (m, 1H), 2.97 (s, 3H), 3.27 (m, 1H), 3.40 (m, 1H), 3.63 (m, 1H), 3.98 (m, 2H), 4.01 (br t, J=3.5 Hz, 1H), 7.20-7.37 (m, 5H)

AP-MS (m/z): 453 (M$^+$+1)

Example 153

Compound 160

Compound 119 (21 mg, 0.052 mmol) prepared in Example 112 was dissolved in a mixed solvent of toluene (1 mL) and tetrahydrofuran (1 mL). To the solution was added 2,4-bis(4-methoxyphenyl)-1,3-dithia-2,4-diphosphethane-2,4-disulfide (Lawesson's reagent) (43 mg, 0.11 mmol), and the mixture was stirred at 90° C. for 5 hours. The reaction mixture was purified by preparative thin layer chromatography (chloroform/methanol=20/1) to obtain Compound 160 (15 mg, 67%).

$^1$H NMR (270 MHz, CDCl$_3$) δ (ppm): 1.30 (s, 9H), 2.76 (s, 3H), 3.08 (s, 3H), 4.08 (dd, J=7.3, 13.8 Hz, 1H), 5.03 (t, J=7.3 Hz, 1H), 5.54 (dd, J=7.3, 13.8 Hz, 1H), 7.26-7.42 (m, 5H), 8.16 (s, 1H)

AP-MS (m/z): 429 (M$^+$+1)

Example 154

Compound 161

In a manner similar to that in Example 100, Compound 161 (70 mg, 37%) was obtained from Compound 106 (0.165 g, 0.393 mmol) prepared in Example 99, oxalyl chloride (2 mL), 2-methylamino)ethanol (295 mg, 3.93 mmol) and triethylamine (476 mg, 4.72 mmol).

AP-MS (m/z): 475 (M$^-$−1)

Example 155

Compound 162

In a manner similar to that in Example 100, Compound 162 (135 mg, 68%) was obtained from Compound 106 (0.165 g, 0.393 mmol) prepared in Example 99, oxalyl chloride (2 mL) and diethanolamine (413 mg, 3.93 mmol).

AP-MS (m/z): 507 (M$^+$+1)

Example 156

Compounds 163 and 164

In a manner similar to that in Example 100, Compound 163 (6.2 mg, 5%) and Compound 164 (36.1 mg, 31%) were obtained from Compound 106 (0.099 g, 0.237 mmol) prepared in Example 99, oxalyl chloride (1.25 mL) and 3-amino-1,2-propanediol (92 µL, 1.19 mmol).

Compound 163

AP-MS (m/z): 493 (M$^+$+1)

Compound 164

AP-MS (m/z): 493 (M$^+$+1)

Example 157

Compound 165

In a manner similar to that in Example 100, Compound 165 (37 mg, 33%) was obtained from Compound 115 (0.102 g, 0.236 mmol) prepared in Example 108, oxalyl chloride (1.25 mL) and 2-aminoethanol (144 mg, 2.36 mmol).

AP-MS (m/z): 477 (M$^+$+1)

Example 158

Compound 166

Compound 105 (0.200 g, 0.461 mmol) prepared in Example 98 was dissolved in tetrahydrofuran (2 mL). To the solution was added lithium aluminium hydride (30 mg, 0.791 mmol) at 0° C., and the mixture was stirred at room temperature for 2 hours. To the reaction mixture was added water and 30% aqueous sodium hydroxide. The insoluble precipitate was removed by filtration, and the filtrate was concentrated under reduced pressure. The residue was purified by preparative thin layer chromatography (chloroform/methanol=9/1) to obtain Compound 166 (64.0 mg, 34%).

$^1$H NMR (270 MHz, CDCl$_3$) δ (ppm): 1.29 (s, 9H), 1.32 (s, 9H), 1.65 (m, 1H), 2.08 (m, 1H), 2.33 (m, 1H), 3.16 (m, 1H), 3.78 (m, 2H), 7.21-7.38 (m, 5H), 7.95 (br s, 1H)

AP-MS (m/z): 404 (M$^-$−1)

Example 159

Compound 167

Compound 166 (0.0448 g, 0.110 mmol) prepared in Example 158 was dissolved in N,N-dimethylacetamide (0.5 mL). To the solution was added sulfamoyl chloride (51.1 mg, 0.442 mmol) at 0° C. with stirring, and the mixture was stirred at 0° C. for 20 minutes. After to the reaction mixture was added water, and the mixture was stirred. The deposited solid was collected by filtration, and dried under reduced pressure. The resulting solid was purified by preparative thin layer chromatography (chloroform/methanol=30/1) to obtain Compound 167 (30.2 mg, 57%).

$^1$H NMR (270 MHz, CDCl$_3$) δ (ppm): 1.29 (s, 9H), 1.33 (s, 9H), 1.89 (m, 1H), 2.14 (m, 1H), 2.38 (m, 1H), 3.32 (m, 1H), 4.28 (m, 1H), 4.43 (m, 1H), 5.08 (br s, 1H), 7.29 (m, 5H), 7.93 (br s, 1H)

AP-MS (m/z): 483 (M$^-$−1)

Example 160

Compounds 168 and 169

Step 1: 2-Aminoacetophenone hydrochloride (4.56 g, 26.6 mmol) was dissolved in dichloromethane (250 mL). To the solution was added triethylamine (9.30 mL, 66.7 mmol), and the mixture was stirred at room temperature for 10 minutes. After the reaction mixture was cooled to 0° C., chloromethanesulfonyl chloride (purity 90%, 3.60 mL, 36.3 mmol) was added to the mixture, and the mixture was stirred at the same temperature for 1 hour. To the reaction mixture was added 2 mol/L hydrochloric acid, and the mixture was extracted with chloroform. The organic layer was washed with saturated aqueous sodium chloride, and then dried over anhydrous sodium sulfate, and the solvent was evaporated under reduced pressure. To the residue was added diethyl ether, and the deposited crystals were collected by filtration and dried to obtain 2-(chloromethylsulfonylamino)acetophenone (5.00 g, 76%).

$^1$H NMR (300 MHz, DMSO-d$_6$) δ (ppm): 4.67 (s, 2H), 4.94 (s, 2H), 7.54 (t, J=8.1 Hz, 2H), 7.67 (t, J=7.5 Hz, 1H), 7.97 (d, J=8.1 Hz, 2H), 8.01 (br s, 1H)

AP-MS (m/z): 247 (M$^+$)

Step 2: 2-(Chloromethylsulfonylamino)acetophenone (1.00 g, 4.05 mmol) prepared above and thiosemicarbazide hydrochloride (1.03 g, 8.07 mmol) were dissolved in methanol (60 mL). To the solution was added concentrated hydrochloric acid (1.00 mL), and the mixture was stirred at 60° C. for 2 hours. The reaction mixture was concentrated, and to the residue was added ethyl acetate and saturated aqueous sodium hydrogencarbonate, and the mixture was subjected to separation. The organic layer was washed with saturated aqueous sodium chloride, and then dried over anhydrous sodium sulfate, and the solvent was evaporated under reduced pressure. The residue was purified by silica gel column chromatography (ethyl acetate/n-hexane=1/1 and 2/1) to obtain 2-(chloromethylsulfonylamino)acetophenone=thiosemicarbazone (0.51 g, 40%).

$^1$H NMR (300 MHz, DMSO-$d_6$) δ (ppm): 4.17 (s, 2H), 4.93 (s, 2H), 7.37-7.42 (m, 3H), 7.52-7.56 (m, 2H), 8.13 (br s, 1H), 8.48 (br, 2H), 8.85 (br s, 1H)

AP-MS (m/z): 319 ($M^+$)

Step 3: 2-Chloromethylsulfonylamino)acetophenone=thiosemicarbazone (7.48 g, 23.4 mmol) prepared above was dissolved in chloroform (250 mL). To the solution was added pyridine (11.4 mL, 141 mmol) and pivaloyl chloride (8.70 mL, 70.6 mmol), and the mixture was stirred at room temperature for 30 minutes. To the reaction mixture was added acetic anhydride (4.40 mL, 46.6 mmol), and the mixture was further stirred at room temperature for 15 hours. To the reaction mixture was added 2 mol/L hydrochloric acid, and the mixture was extracted with chloroform. The organic layer was washed with saturated aqueous sodium chloride, and then dried over anhydrous sodium sulfate, and the solvent was evaporated under reduced pressure. The residue was purified by silica gel column chromatography (ethyl acetate/n-hexane=1/1 and 2/1) to obtain Compound 168 (3.56 g, 25%) and Compound 169 (1.77 g, 14%).

Compound 168

$^1$H NMR (300 MHz, DMSO-$d_6$) δ (ppm): 1.16 (s, 9H), 2.23 (s, 3H), 4.00 (dd, J=11.3, 8.0 Hz, 1H), 4.47 (dd, J=11.3, 2.5 Hz, 1H), 4.91 (d, J=12.0 Hz, 1H), 4.97 (d, J=12.0 Hz, 1H), 7.28-7.39 (m, 5H), 8.10 (br s, 1H), 11.2 (br s, 1H)

AP-MS (m/z): 446 ($M^+$)

Compound 169

$^1$H NMR (300 MHz, DMSO-$d_6$) δ (ppm): 2.01 (s, 3H), 2.18 (s, 3H), 3.95 (d, J=14.3 Hz, 1H), 4.45 (d, J=14.3 Hz, 1H), 4.91 (d, J=12.0 Hz, 1H), 4.97 (d, J=12.0 Hz, 1H), 7.25-7.39 (m, 5H), 8.08 (br s, 1H), 11.6 (br s, 1H)

AP-MS (m/z): 404 ($M^+$)

Example 161

Compounds 170 and 171

Step 1: 2-Aminoacetophenone hydrochloride (1.00 g, 5.85 mmol) was dissolved in dichloromethane (50 mL). To the solution was added triethylamine (2.50 mL, 17.9 mmol), and the mixture was stirred at room temperature for 10 minutes. After the reaction mixture was cooled to 0° C., chloroethanesulfonyl chloride (0.92 mL, 8.80 mmol) was added to the mixture, and the mixture was stirred at the same temperature for 15 minutes. To the reaction mixture was added 2 mol/L hydrochloric acid and the mixture was extracted with chloroform. The organic layer was washed with saturated aqueous sodium chloride, and then dried over anhydrousسodium sulfate, and the solvent was evaporated under reduced pressure. To the residue was added a mixed solvent of ethyl acetate and n-hexane for crystallization to obtain 2-(vinylsulfonylamino)acetophenone (0.42 g, 32%).

$^1$H NMR (300 MHz, CDCl$_3$) δ (ppm): 4.54 (d, J=4.5 Hz, 2H), 5.42 (br s, 1H), 5.94 (d, J=9.9 Hz, 1H), 6.28 (d, J=16.5 Hz, 1H), 6.53 (br dd, J=16.2, 9.9 Hz, 1H), 7.52 (t, J=7.5 Hz, 3H), 7.65 (t, J=7.8 Hz, 1H), 7.93 (t, J=5.1 Hz, 1H)

AP-MS (m/z): 225 ($M^+$)

Step 2: 2-(Vinylsulfonylamino)acetophenone (0.32 g, 1.42 mmol) prepared above and thiosemicarbazide hydrochloride (0.27 g, 2.13 mmol) were dissolved in methanol (20 mL). To the solution was added concentrated hydrochloric acid (2 drops), and the mixture was stirred at room temperature for 3 hours. The reaction mixture was concentrated. To the residue was added ethyl acetate and saturated aqueous sodium hydrogencarbonate, and the organic layer was subjected to separation. The organic layer was washed with saturated aqueous sodium chloride, and then dried over anhydrous sodium sulfate, and the solvent was evaporated under reduced pressure. The residue was purified by silica gel column chromatography (ethyl acetate/n-hexane=1/1) to obtain 2-(vinylsulfonylamino)acetophenone=thiosemicarbazone (0.25 g, 58%).

$^1$H NMR (300 MHz, CDCl$_3$) δ (ppm): 4.10 (s, 2H), 5.97 (d, J=9.9 Hz, 1H), 6.25 (d, J=16.8 Hz, 1H), 6.54 (dd, J=16.8, 9.9 Hz, 1H), 7.24-7.27 (m, 2H), 7.42 (br s, 1H), 7.52-7.53 (m, 3H), 7.81 (br s, 1H), 8.70 (m, 1H)

AP-MS (m/z): 297 ($M^+$)

Step 3: 2-(Vinylsulfonylamino)acetophenone=thiosemicarbazone (0.25 g, 0.83 mmol) prepared above was dissolved in acetone (10 mL). To the solution was added pyridine (0.34 mL, 4.17 mmol) and pivaloyl chloride (0.31 mL, 2.50 mmol), and the mixture was stirred at room temperature for 30 minutes. To the reaction mixture was added acetic anhydride (0.16 mL, 1.66 mmol), and the mixture was further stirred for 3 days at room temperature. The reaction mixture was concentrated, and to the residue was added ethyl acetate and 2 mol/L hydrochloric acid, and the mixture was subjected to separation. The organic layer was washed with saturated aqueous sodium chloride, and then dried over anhydrous sodium sulfate, and the solvent was evaporated under reduced pressure. The residue was purified by silica gel column chromatography (ethyl acetate/n-hexane=1/1) to obtain Compound 170 (0.18 g, 52%) and Compound 171 (0.10 g, 26%).

Compound 170

$^1$H NMR (300 MHz, CDCl$_3$) δ (ppm): 1.27 (s, 9H), 2.31 (s, 3H), 3.87 (dd, J=13.4, 5.0 Hz, 1H), 4.45 (dd, J=13.4, 7.9 Hz, 1H), 5.57 (br s, 1H), 5.92 (d, J=9.9 Hz, 1H), 6.25 (d, J=16.5 Hz, 1H), 6.49 (dd, J=16.5, 9.9 Hz, 1H), 7.27-7.34 (m, 5H), 8.22 (br s, 1H)

AP-MS (m/z): 424 ($M^+$)

Compound 171

$^1$H NMR (300 MHz, CDCl$_3$) δ (ppm): 1.29 (s, 9H), 1.33 (s, 9H), 3.85 (dd, J=13.5, 4.8 Hz, 1H), 4.49 (dd, J=13.5, 8.1 Hz, 1H), 5.29 (br s, 1H), 5.93 (br d, J=9.9 Hz, 1H), 6.27 (br d, J=16.5 Hz, 1H), 6.53 (br dd, J=16.4, 9.6 Hz, 1H), 7.27-7.34 (m, 5H), 8.06 (br s, 1H)

AP-MS (m/z): 466 ($M^+$)

Example 162

Compound 172

Compound 170 (0.05 g, 0.11 mmol) prepared in Step 3 of Example 161 was dissolved in acetonitrile (3 mL). To the solution was added morpholine (0.10 mL), and the mixture was stirred at 80° C. for 2 hours. The reaction mixture was concentrated, and the residue was purified by silica gel column chromatography (chloroform/methanol=10/1) to obtain Compound 172 (0.04 g, 77%).

$^1$H NMR (300 MHz, CDCl$_3$) δ (ppm): 1.27 (s, 9H), 2.33 (s, 3H), 2.42-2.45 (m, 4H), 2.78 (dquin, J=16.5, 6.0 Hz, 2H), 3.19 (t, J=6.6 Hz, 2H), 3.65-3.68 (m, 4H), 4.04 (dd, J=14.1, 4.8 Hz, 1H), 4.55 (dd, J=14.1, 7.5 Hz, 1H), 5.73 (br s, 1H), 7.30-7.38 (m, 5H), 8.05 (br s, 1H)

AP-MS (m/z): 511 (M$^+$)

Example 163

Compound 173

In a manner similar to that in Example 162, Compound 173 (0.03 g, 66%) was obtained from Compound 170 (0.05 g, 0.11 mmol) prepared in Step 3 of Example 161 and 70% aqueous ethylamine (0.10 mL).

$^1$H NMR (300 MHz, CDCl$_3$) δ (ppm): 1.10 (t, J=6.9 Hz, 3H), 1.27 (s, 9H), 2.32 (s, 3H), 2.65 (quin, J=7.2 Hz, 2H), 3.05-3.09 (m, 2H), 3.18-3.20 (m, 2H), 4.00 (d, J=13.5 Hz, 1H), 4.55 (d, J=13.8 Hz, 1H), 7.30-7.37 (m, 5H), 8.07 (br s, 1H)

AP-MS (m/z): 470 (M$^+$+1)

Example 164

Compound 174

In a manner similar to that in Example 162, Compound 174 (0.03 g, 67%) was obtained from Compound 170 (0.05 g, 0.11 mmol) prepared in Step 3 of Example 161 and 2 mol/L dimethylamine methanol solution (0.10 mL).

$^1$H NMR (300 MHz, CDCl$_3$) δ (ppm): 1.26 (s, 9H), 2.24 (s, 6H), 2.31 (s, 3H), 2.71-2.81 (m, 2H), 3.12-3.19 (m, 2H), 4.00 (d, J=13.5 Hz, 1H), 4.56 (d, J=13.5 Hz, 1H), 6.00 (br s, 1H), 7.31-7.36 (m, 5H), 8.06 (br s, 1H)

AP-MS (m/z): 469 (M$^+$)

Example 165

Compound 175

In a manner similar to that in Example 162, Compound 175 (0.03 g, 52%) was obtained from Compound 170 (0.05 g, 0.11 mmol) prepared in Step 3 of Example 161 and 2-aminoethanol (0.10 mL).

$^1$H NMR (300 MHz, CDCl$_3$) δ (ppm): 1.26 (s, 9H), 2.35 (s, 3H), 2.65-2.78 (m, 2H), 3.08-3.30 (m, 4H), 3.64 (t, J=5.1 Hz, 2H), 3.98 (d, J=13.5 Hz, 1H), 4.54 (d, J=13.5 Hz, 1H), 7.26-7.38 (m, 5H), 8.25 (br s, 1H)

AP-MS (m/z): 485 (M$^+$)

Example 166

Compound 176

In a manner similar to that in Example 162, Compound 176 (0.01 g, 26%) was obtained from Compound 171 (0.05 g, 0.11 mmol) prepared in Step 3 of Example 161 and 70% aqueous ethylamine (0.10 mL).

$^1$H NMR (300 MHz, CDCl$_3$) δ (ppm): 1.18 (m, 3H), 1.28 (s, 9H), 1.34 (s, 9H), 2.63 (quin, J=7.0 Hz, 2H), 2.73 (br q, J=6.3 Hz, 1H), 2.84 (br q, J=6.2 Hz, 1H), 3.18 (br t, J=6.6 Hz, 2H), 4.02 (d, J=13.2 Hz, 1H), 4.58 (d, J=13.2 Hz, 1H), 5.85 (br s, 1H), 7.27-7.35 (m, 5H), 8.02 (br s, 1H)

AP-MS (m/z): 512 (M$^+$+1)

Example 167

Compound 177

In a manner similar to that in Example 162, Compound 177 (0.02 g, 39%) was obtained from Compound 171 (0.05 g, 0.11 mmol) prepared in Step 3 of Example 161 and 2 mol/L dimethylamine methanol solution (0.10 mL).

$^1$H NMR (300 MHz, CDCl$_3$) δ (ppm): 1.28 (s, 9H), 1.34 (s, 9H), 2.25 (s, 6H), 2.73 (br q, J=6.3 Hz, 1H), 2.84 (br q, J=6.2 Hz, 1H), 3.18 (br t, J=6.6 Hz, 2H), 4.02 (d, J=13.2 Hz, 1H), 4.58 (d, J=13.2 Hz, 1H), 5.85 (br s, 1H), 7.27-7.35 (m, 5H), 8.02 (br s, 1H)

AP-MS (m/z): 512 (M$^+$+1)

Example 168

Compound 178

In a manner similar to that in Example 11, Compound 178 (64.0 mg, 38%) was obtained from carbomethoxypropiophenone=thiosemicarbazone (0.144 g, 0.543 mol) prepared in Step 1 of Example 98, acetic anhydride (77 μL, 0.814 mmol) and pyridine (79 μL, 0.977 mmol).

$^1$H NMR (270 MHz, CDCl$_3$) δ (ppm): 2.13 (s, 3H), 2.20-2.70 (m, 4H), 3.61 (s, 3H), 6.52 (br s, 2H), 7.20-7.35 (m, 5H)

Example 169

Compound 179

In a manner similar to that in Example 15, Compound 179 (24.0 mg, 94%) was obtained from Compound 178 (0.0200 g, 0.0650 mol) prepared in Example 168, pivaloyl chloride (16 μL, 0.130 mmol) and pyridine (15 μL, 0.182 mmol).

$^1$H NMR (270 MHz, CDCl$_3$) δ (ppm): 1.30 (s, 9H), 2.10 (s, 3H), 2.17-2.75 (m, 4H), 3.57 (s, 3H), 7.18-7.32 (m, 5H), 8.02 (br s, 1H)

AP-MS (m/z): 390 (M$^-$−1)

Example 170

Compound 180

Compound 100 (304 mg, 0.0690 mmol) prepared in Example 93 and cerium chloride heptahydrate (257 mg, 0.690 mmol) were dissolved in methanol (800 mL). To the solution was gradually added sodium borohydride (522 mg, 13.8 mmol), and the mixture was stirred at room temperature for 20 minutes. The reaction mixture was concentrated under reduced pressure. To the residue was added 1 mol/L hydrochloric acid (100 mL), and the mixture was extracted with chloroform. The organic layer was dried over anhydrous sodium sulfate, and the solvent was evaporated under reduced pressure. The residue was purified by silica gel column chromatography (chloroform/acetone/ethyl acetate/n-hexane=9/1/1/1) to obtain Compound 180 (217 mg, 85%).

$^1$H NMR (270 MHz, CDCl$_3$) δ (ppm): 1.14 (t, J=7.0 Hz, 6H), 2.68 (m, 1H), 2.98 (s, 3H), 3.27 (m, 2H), 3.44 (m, 1H), 3.63 (m, 1H), 4.18 (br s, 2H), 4.51 (br s, 1H), 7.30 (m, 5H)

AP-MS (m/z): 371 (M$^+$+1)

Example 171

Compound 181

In a manner similar to that in Example 15, Compound 181 (87.3 mg, 71%) was obtained from Compound 180 (100 mg, 0.270 mmol) prepared in Example 170, pyridine (65.4 μL, 0.810 mmol) and pivaloyl chloride (83.4 μL, 0.676 mmol).

AP-MS (m/z): 455 (M$^+$+1)

Example 172

Compound 182

Compound 180 (60.6 mg, 0.170 mmol) obtained in Example 170 was dissolved in dichloromethane. To the solution was added pyridine (63.2 μL, 0.788 mmol) and 5-bromovaleryl chloride (23.0 μL, 0.172 mmol), and the mixture was stirred at room temperature for 5 hours. To the reaction mixture was added 1 mol/L hydrochloric acid and the mixture was extracted with chloroform. The organic layer was dried over anhydrous sodium sulfate, and the solvent was evaporated under reduced pressure. The residue was dissolved in dimethyl sulfoxide (0.3 mL). To the solution was added sodium acetate (58.7 mg), and the mixture was stirred at 100° C. for 5 minutes. To the reaction mixture was added water (20 mL) and 1 mol/L hydrochloric acid (20 mL), and the mixture was extracted with chloroform. And then, the organic layer was dried over anhydrous sodium sulfate, and the solvent was evaporated under reduced pressure. The residue was purified by preparative thin layer chromatography (chloroform/acetone/ethyl acetate/n-hexane=9/1/1/1) to obtain Compound 182 (42.5 mg, 45%).

AP-MS (m/z): 453 (M$^+$+1)

Example 173

Compound 183

Compound 180 (100 mg, 0.270 mmol) prepared in Example 170 and pyridine (31.5 μL, 0.389 mmol) were dissolved in dichloromethane (2 mL). To the solution was added 4-bromobutyryl chloride (37.5 μL, 0.324 mmol) at 0° C., and the mixture was stirred at room temperature for 5 hours. To the reaction mixture was added 1 mol/L hydrochloric acid, and the mixture was extracted with chloroform. The organic layer was dried over anhydrous sodium sulfate, and the solvent was evaporated under reduced pressure. To the residue was added methanol (20 mL) and potassium carbonate (1.0 g), and the mixture was vigorously stirred at room temperature for 20 minutes. To the reaction mixture was added water and 1 mol/L hydrochloric acid, and the mixture was extracted with chloroform. The organic layer was dried over anhydrous sodium sulfate, and the solvent was evaporated. The residue was purified by silica gel column chromatography (chloroform/acetone/ethyl acetate/n-hexane=9/1/1/1) to obtain Compound 183 (27.6 mg, 37%).

$^1$H NMR (270 MHz, CDCl$_3$) δ (ppm): 1.15 (d, J=6.6 Hz, 6H), 2.22 (m, 2H), 2.55-2.67 (m, 3H), 2.94 (s, 3H), 3.31-3.47 (m, 3H), 3.61 (m, 1H), 3.91-3.98 (m, 2H), 5.0 (br s, 1H), 7.20-7.35 (m, 5H)

AP-MS (m/z): 437 (M$^-$−1)

Example 174

Compound 184

In a manner similar to that in Example 173, Compound 180 (84.1 mg, 0.227 mmol) prepared in Example 170 was treated with pyridine (88.0 μL, 1.09 mmol) and 5-bromovaleryl chloride (121 μL, 0.908 mmol), and then treated with methanol and potassium carbonate (1.0 g) to obtain Compound 184 (89.1 mg, 81%).

AP-MS (m/z): 485 (M$^+$+1)

Example 175

Compound 185

In a manner similar to that in Step 3 of Example 92, Compound 185 (16.7 g, 85%) was obtained from 3-(methylsulfonylamino)propiophenone=thiosemicarbazone (14.4 g, 47.9 mmol), propionyl chloride (16.7 mL, 192 mmol) and pyridine (18.6 mL, 230 mmol).

$^1$H NMR (270 MHz, CDCl$_3$) δ (ppm): 1.12 (t, J=7.5 Hz, 3H), 1.19 (t, J=7.3 Hz, 3H), 2.37 (m, 2H), 2.63 (m, 3H), 2.96 (s, 31H), 3.35 (m, 2H), 3.58 (m, 1H), 4.55 (br s, 1H), 7.20-7.35 (m, 5H), 8.01 (br s, 1H)

Example 176

Compound 186

In a manner similar to that in Example 170, Compound 186 (11.7 g, 81%) was obtained from Compound 185 (16.7 g, 40.5 mmol) prepared in Example 175, cerium chloride heptahydrate (15.1 g, 40.5 mol) and sodium borohydride (12.8 g, 338 mol).

$^1$H NMR (270 MHz, CDCl$_3$) δ (ppm): 1.13 (t, J=8.7 Hz, 3H), 2.61-2.71 (m, 3H), 2.97 (s, 3H), 3.27-3.47 (m, 2H), 3.60-3.67 (m, 1H), 4.21 (br s, 2H), 4.65 (br s, 1H), 7.26-7.36 (m, 5H)

Example 177

Compound 187

In a manner similar to that in Example 15, Compound 187 (90.3 mg, 76%) was obtained from Compound 186 (96.0 mg, 0.269 mmol) prepared in Example 176, pyridine (65.4 μL, 0.810 mmol) and pivaloyl chloride (83.4 μL, 0.676 mmol).

$^1$H NMR (270 MHz, CDCl$_3$) δ (ppm): 1.13 (t, J=6.0 Hz, 3H), 1.28 (s, 9H), 2.66 (m, 3H), 2.97 (s, 3H), 3.35 (m, 2H), 3.61 (m, 1H), 4.58 (br s, 1H), 7.32 (m, 5H), 8.08 (br s, 1H)

AP-MS (m/z): 441 (M$^+$+1)

Example 178

Compound 188

In a manner similar to that in Example 172, Compound 188 (42.5 mg, 45%) was obtained from Compound 186 (100 mg, 0.221 mmol) prepared in Example 176, pyridine (85 μL, 1.05 mmol), 4-bromobutyryl chloride (110 μL, 0.949 mmol) and potassium carbonate (1.0 g).

$^1$H NMR (270 MHz, CDCl$_3$) δ (ppm): 1.14 (t, J=7.5 Hz, 3H), 2.19 (m, 2H), 2.50-2.81 (m, 5H), 2.96 (s, 3H), 3.35 (m, 2H), 3.59 (m, 1H), 3.93 (m, 2H), 4.52 (br s, 1H), 7.20-7.34 (m, AP-MS (m/z): 424 (M$^-$−1)

Example 179

Compound 189

In a manner similar to that in Example 172, Compound 189 (27.6 mg, 37%) was obtained from Compound 186 (60.6 mg, 0.170 mmol) prepared in Example 176, pyridine (63.2 μL, 0.788 mmol), 5-bromovaleryl chloride (110 μL, 0.949 mmol) and potassium carbonate (1.0 g).

$^1$H NMR (270 MHz, CDCl$_3$) δ (ppm): 1.14 (t, J=7.5 Hz, 3H), 1.79-1.99 (m, 4H), 2.54-2.75 (m, 5H), 2.96 (s. 3H), 3.19-3.27 (m, 2H), 3.57-3.68 (m, 1H), 3.83-3.95 (m, 2H), 4.36 (br s, 1H), 7.20-7.37 (m, 5H)

AP-MS (m/z): 439 (M$^+$+1)

Example 180

Compound 190

In a manner similar to that in of Example 170, Compound 190 (86.5 mg, 0.248 mmol) was obtained from Compound 105 (1.01 g, 2.33 mmol) prepared in Example 98 and sodium borohydride (2.20 g, 58.2 mmol).

$^1$H NMR (270 MHz, CDCl$_3$) δ (ppm): 1.30 (s, 9H), 2.37-2.46 (m, 1H), 2.63-2.86 (m, 2H), 3.41-3.51 (m, 1H), 3.71 (s, 3H), 4.09 (br s, 2H), 7.22-7.43 (m, 5H)

Example 181

Compound 191

Compound 191 (89.5 mg, 29%) was obtained in the same manner as that in Example 133 from Compound 190 (86.5 mg, 0.248 mmol) obtained in Example 180 and 4-bromobutyryl chloride (57 µL, 0.495 mmol).

AP-MS (m/z): 496 (M$^-$−1)

Example 182

Compound 192

Compound 191 (89.5 mg, 0.18 mmol) prepared in Example 181 was dissolved in N,N-dimethylformamide (2.0 mL). To the solution was added 60% sodium hydride (14 mg, 0.359 mmol), and the mixture was stirred at room temperature for 1 hour. To the reaction mixture was added acetic acid and water, and the mixture was extracted with ethyl acetate. The organic layer was washed with saturated saline, and then dried over anhydrous sodium sulfate, and the solvent was evaporated under reduced pressure. The residue was purified by silica gel column chromatography (ethyl acetate/n-hexane=2/1) to obtain Compound 192 (30.2 mg, 40%).

$^1$H NMR (270 MHz, CDCl$_3$) δ (ppm): 1.36 (s, 9H), 2.17-2.42 (m, 3H), 2.53-2.84 (m, 4H), 3.38-3.50 (s, 1H), 3.72 (s, 3H), 3.97 (m, 2H), 7.22-7.39 (m, 5H)

Example 183

Compound 193

In a manner similar to that in Example 99, Compound 193 (21.7 mg, 74%) was obtained from Compound 192 (30.2 mg, 0.723 mmol) prepared in Example 182 and sodium hydroxide (8.7 mg, 0.217 mmol).

AP-MS (m/z): 402 (M$^-$−1)

Example 184

Compound 194

In a manner similar to that in Example 100, Compound 194 (7.3 mg, 30%) was obtained from Compound 193 (21.7 mg, 0.054 mmol) prepared in Example 183, oxalyl chloride (0.25 ml) and 2-aminoethanol (16 µL, 26.9 mmol).

$^1$H NMR (270 MHz, CDCl$_3$) δ (ppm): 1.34 (s, 9H), 2.17-2.28 (m, 3H), 2.54-2.82 (m, 2H), 3.34-3.46 (m, 3H), 3.72 (dd, J=4.0, 6.0 Hz, 2H), 3.96 (br q, J=7.0 Hz, 2H), 7.32-7.34 (m, 5H)

Example 185

Compound 195

Step 1: In a manner similar to that in Step 1 of Example 1, 2-acetoxy-1-indanone=thiosemicarbazone (3.23 g, 57%) was obtained from 2-acetoxy-1-indanone (4.1 g, 21.6 mmol) and thiosemicarbazide hydrochloride (3.0 g, 23.7 mmol).

Step 2: In a manner similar to that in Step 2 of Example 1, 3-acetyl-5-aminospiro[1,3,4-thiadiazolin-2,1'-indan]-2'-yl acetate (187.4 mg, 48%) was obtained from 2-acetoxy-1-indanone=thiosemicarbazone (335.5 mg, 1.27 mmol) prepared above, pyridine (13 mL) and acetic anhydride (136 µL, 1.53 mmol).

Step 3: 3-Acetyl-5-aminospiro[1,3,4-thiadiazolin-2,1'-indan]-2'-yl acetate (163.8 mg) prepared above was dissolved in dichloromethane (2.0 mL). To the solution was added pyridine (520 µL, 6.44 mmol) and pivaloyl chloride (661 µL, 5.36 mmol), and the mixture was stirred at room temperature for 24 hours. To the reaction mixture was added water and chloroform, and the mixture was extracted with chloroform. The organic layer was washed with saturated aqueous sodium chloride, and then dried over anhydrous sodium sulfate, and the solvent was evaporated under reduced pressure. The residue was purified by silica gel column chromatography (chloroform/ethyl acetate=3/2) to obtain Compound 195 (118.0 mg, 57%) as a diastereoisomer mixture.

AP-MS (m/z): 390 (M$^+$+1)

Example 186

Compound 196

Compound 195 (90.3 mg, 0.233 mmol) prepared in Example 185 was dissolved in methanol solution of 10% ammonia (4.8 mL), and the solution was allowed to stand at room temperature for 6 hours. The reaction mixture was concentrated, and then the residue was purified by silica gel column chromatography (chloroform/ethyl acetate=3/2) to obtain Compound 196 (16.6 mg, 20%) as a diastereoisomer mixture.

FAB-MS (m/z): 348 (M$^+$+1)

Example 187

Compound 197

Step 1: In a manner similar to that in Step 1 of Example 1, 4-acetoxy-1-indanone=thiosemicarbazone (2.78 g, 80%) was obtained from 4-acetoxy-1-indanone (2.51 g, 13.2 mmol) and thiosemicarbazide hydrochloride (1.85 g, 14.5 mmol).

Step 2: In a manner similar to that in Example 11, Compound 197 (193.9 mg, 39%) was obtained from 4-acetoxy-1-indanone=thiosemicarbazone (364.5 mg, 1.38 mmol) prepared above, acetic anhydride (123 µL, 1.38 mmol) and pyridine (112 µL, 1.38 mmol).

$^1$H NMR (300 MHz, CDCl$_3$) δ (ppm): 2.18 (s, 3H), 2.30 (s, 3H), 2.59-2.68 (m, 1H), 2.76-2.86 (m, 1H), 3.09-3.30 (m, 2H), 4.17 (br s, 2H), 6.99 (dd, J=7.7, 1.5 Hz, 1H), 7.31 (m, 2H)

Example 188

Compound 198

In a manner similar to that in Example 15, Compound 198 (136 mg, 98%) was obtained from Compound 197 (108.8 mg, 0.356 mmol) prepared in Example 187, pyridine (346 µL, 4.28 mmol) and pivaloyl chloride (439 µL, 3.56 mmol).

$^1$H NMR (270 MHz, CDCl$_3$) δ (ppm): 1.34 (s, 9H), 2.18 (s, 3H), 2.29 (s, 3H), 2.56-2.63 (m, 1H), 2.79-2.92 (m, 1H), 3.08-3.22 (m, 2H), 6.98-7.03 (m, 1H), 7.28-7.31 (m, 2H), 8.08 (br s, 1H)

Example 189

Compound 199

In a manner similar to that in Example 186, Compound 199 (70.0 mg, 94%) was obtained from Compound 198 (83.1 mg, 0.214 mmol) prepared in Example 188 and methanol solution of 10% ammonia (4.2 mL).

$^1$H NMR (300 MHz, CDCl$_3$) δ (ppm): 1.34 (s, 9H), 2.21 (s, 3H), 2.58-2.67 (m, 1H), 2.81-2.91 (m, 1H), 3.07-3.27 (m, 2H), 5.25 (br s, 1H), 6.62 (d, J=7.7 Hz, 1H), 6.94 (d, J=7.7 Hz, 1H), 7.10 (t, J=7.7 Hz, 1H), 7.99 (br s, 1H)

Example 190

Tablets

Tablets comprising the following composition are obtained according to the conventional method.

| | |
|---|---|
| Compound 1 | 5 mg |
| Lactose | 60 mg |
| Potato starch | 30 mg |
| Polyvinyl alcohol | 2 mg |
| Magnesium stearate | 1 mg |
| Tar dye | trace |

INDUSTRIAL APPLICABILITY

The present invention provides a thiadiazoline derivative or a pharmacologically acceptable salt thereof which is useful for therapeutic treatment of a human malignant tumor, for example, breast cancer, gastric cancer, ovarian cancer, colon cancer, lung cancer, brain tumor, laryngeal cancer, hematological cancer, urinary or genital tumor including bladder cancer and prostatic cancer, renal cancer, skin carcinoma, hepatic carcinoma, pancreatic cancer, or uterine cancer, or the like. In addition, the present invention provides an antitumor agent comprising a thiadiazoline derivative or a pharmacologically acceptable salt thereof as an active ingredient.

What is claimed is:

1. A method for the therapeutic treatment of a malignant tumor selected from the group consisting of breast cancer, ovarian cancer, lung cancer, prostatic cancer, renal cancer, skin carcinoma, hepatic carcinoma, and pancreatic cancer, in a human in need thereof comprising administering to the human a therapeutically effective amount of a compound represented by formula (99), (181), (188), (176), or (177),

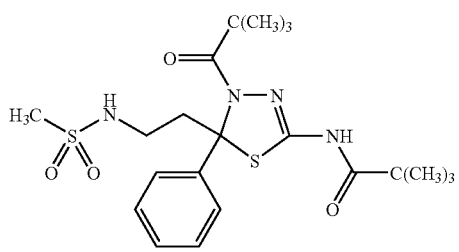

(99)

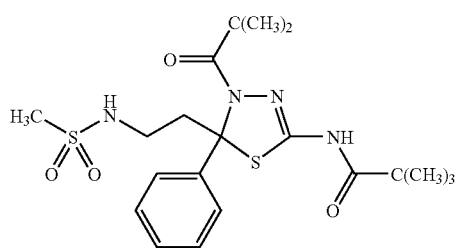

(181)

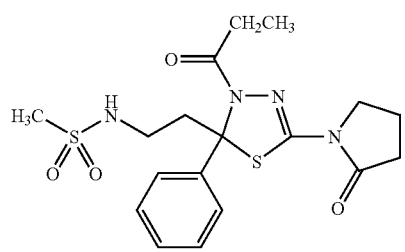

(188)

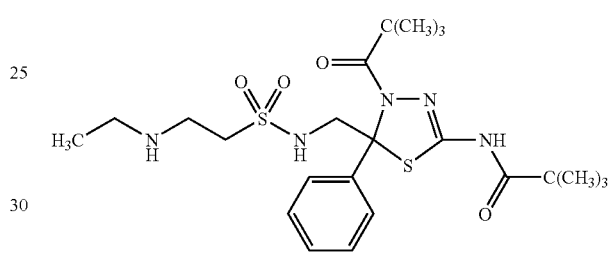

(176)

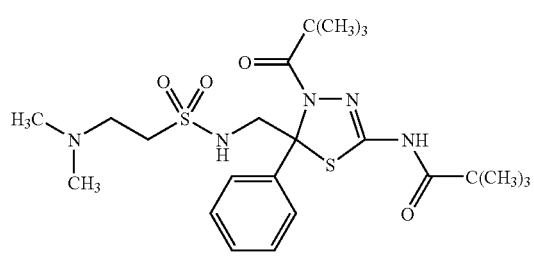

(177)

or a pharmacologically acceptable salt thereof.

2. The method according to claim 1, wherein the malignant tumor is breast cancer, ovarian cancer, lung cancer, or prostatic cancer.

3. The method according to claim 1, wherein the malignant tumor is ovarian cancer.

4. The method according to claim 1, wherein the malignant tumor is breast cancer.

5. The method according to claim 1, wherein the malignant tumor is lung cancer.

6. The method according to claim 1, wherein the malignant tumor is prostatic cancer.

7. A method for the therapeutic treatment of a malignant tumor selected from the group consisting of breast cancer, ovarian cancer, lung cancer, prostatic cancer, renal cancer, skin carcinoma, hepatic carcinoma, and pancreatic cancer, in a human in need thereof comprising administering to the human a therapeutically effective amount of a compound represented by formula (176), (176)

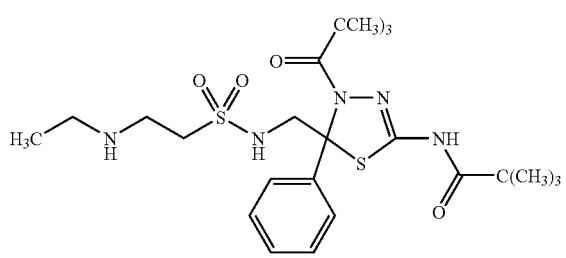

or a pharmacologically acceptable salt thereof.

8. The method according to claim 7, wherein the malignant tumor is breast cancer, ovarian cancer, lung cancer, or prostatic cancer.

9. The method according to claim 7, wherein the malignant tumor is ovarian cancer.

10. The method according to claim 7, wherein the malignant tumor is breast cancer.

11. The method according to claim 7, wherein the malignant tumor is lung cancer.

12. The method according to claim 7, wherein the malignant tumor is prostatic cancer.

* * * * *

UNITED STATES PATENT AND TRADEMARK OFFICE
CERTIFICATE OF CORRECTION

PATENT NO.         : 7,759,371 B2                          Page 1 of 1
APPLICATION NO.    : 12/098736
DATED              : July 20, 2010
INVENTOR(S)        : C. Murakata et al.

It is certified that error appears in the above-identified patent and that said Letters Patent is hereby corrected as shown below:

On the title page, item [73] Assignees, change "Kyowa Hakko Kinn Co., Ltd." to --Kyowa Hakko Kirin Co., Ltd.--.

On the title page, item [56] on page 2, under Foreign Patent Documents, change "WO 0 217 519   4/1987" to --EP 0 217 519   4/1987--.

In the printed patent, in the claims (Claim 1, line 25), Column 94, line 3, second formula in Claim 1, change

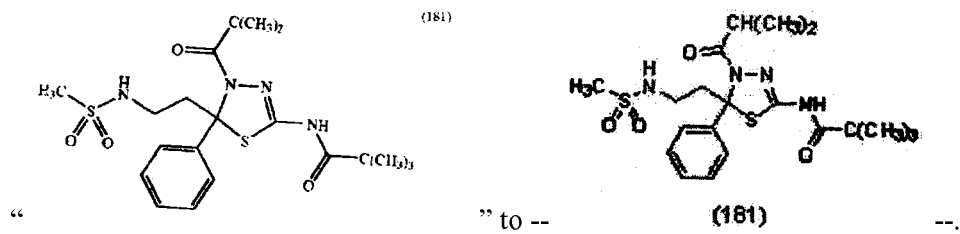

Signed and Sealed this
Twenty-ninth Day of March, 2011

David J. Kappos
*Director of the United States Patent and Trademark Office*